US009907911B2

(12) United States Patent
Constantineau et al.

(10) Patent No.: US 9,907,911 B2
(45) Date of Patent: Mar. 6, 2018

(54) PORTABLE DRUG MIXING AND DELIVERY DEVICE AND ASSOCIATED METHODS

(71) Applicant: WINDGAP MEDICAL, INC, Somerville, MA (US)

(72) Inventors: Cole Constantineau, Cambridge, MA (US); Christopher J. Stepanian, Somerville, MA (US); Adam R. Standley, Cambridge, MA (US); Michel Bruehwiler, Newton, MA (US); Brent Buchine, Austin, TX (US); Jeffrey Thomas Chagnon, Somerville, MA (US); Robert Brik, Cambridge, MA (US)

(73) Assignee: Windgap Medical, Inc., Somerville, MA (US)

( * ) Notice: Subject to any disclaimer, the term of this patent is extended or adjusted under 35 U.S.C. 154(b) by 0 days.

(21) Appl. No.: 15/034,967

(22) PCT Filed: Aug. 18, 2015

(86) PCT No.: PCT/US2015/045761
§ 371 (c)(1),
(2) Date: Aug. 1, 2016

(87) PCT Pub. No.: WO2016/028814
PCT Pub. Date: Feb. 25, 2016

(65) Prior Publication Data
US 2017/0100541 A1 Apr. 13, 2017

Related U.S. Application Data

(60) Provisional application No. 62/038,386, filed on Aug. 18, 2014, provisional application No. 62/126,011, (Continued)

(51) Int. Cl.
*A61M 5/20* (2006.01)
*A61M 5/00* (2006.01)
(Continued)

(52) U.S. Cl.
CPC ............ *A61M 5/2066* (2013.01); *A61M 5/00* (2013.01); *A61M 5/19* (2013.01); *A61M 5/2033* (2013.01);
(Continued)

(58) Field of Classification Search
CPC .. A61M 2005/2006; A61M 2005/2013; A61M 2005/202; A61M 2005/206;
(Continued)

(56) References Cited

U.S. PATENT DOCUMENTS 3,680,558 A   8/1972 Kapelowitz
3,946,732 A   3/1976 Hurscham
(Continued)

FOREIGN PATENT DOCUMENTS

EP   961612 B1   4/2009
FR   274810      6/1997
(Continued)

*Primary Examiner* — Imani Hayman
(74) *Attorney, Agent, or Firm* — Ascentage Patent Law, LLC; Travis Lee Johnson; David S. Einfeldt

(57) ABSTRACT

A portable auto-injector configured to store a dry medication separately from a liquid component, wherein removal of a cap opens a rotary valve allowing for the initiation of a mixing step prior to injection. An extendable needle guard is provided over the delivery assembly which prevents premature injection as well as inadvertent sticks or other cross contamination of a needle. The needle guard can also form part of a secondary trigger mechanism which injects the reconstituted drug after the mixing stage is complete.

1 Claim, 40 Drawing Sheets

Related U.S. Application Data filed on Feb. 27, 2015, provisional application No. 62/204,940, filed on Aug. 13, 2015, provisional application No. 62/061,664, filed on Oct. 8, 2014, provisional application No. 62/120,792, filed on Feb. 25, 2015.

(51) Int. Cl.

| | | |
|---|---|---|
| *A61M 5/28* | (2006.01) | |
| *A61M 5/315* | (2006.01) | |
| *A61M 5/32* | (2006.01) | |
| *A61M 5/19* | (2006.01) | |
| *A61M 5/31* | (2006.01) | |
| *A61M 5/24* | (2006.01) | |

(52) U.S. Cl.
CPC .......... *A61M 5/2053* (2013.01); *A61M 5/288* (2013.01); *A61M 5/31596* (2013.01); *A61M 5/321* (2013.01); *A61M 5/326* (2013.01); *A61M 5/3232* (2013.01); *A61M 5/3234* (2013.01); *A61M 5/3243* (2013.01); *A61M 5/3245* (2013.01); *A61M 5/3271* (2013.01); *A61M 5/3293* (2013.01); *A61M 2005/202* (2013.01); *A61M 2005/2006* (2013.01); *A61M 2005/206* (2013.01); *A61M 2005/2013* (2013.01); *A61M 2005/2073* (2013.01); *A61M 2005/2474* (2013.01); *A61M 2005/3128* (2013.01); *A61M 2005/3132* (2013.01); *A61M 2005/3247* (2013.01); *A61M 2005/3267* (2013.01)

(58) Field of Classification Search
CPC .. A61M 2005/2073; A61M 2005/2474; A61M 2005/3128; A61M 2005/3132; A61M 2005/3247; A61M 2005/3267; A61M 5/00; A61M 5/19; A61M 5/2033; A61M 5/2053; A61M 5/2066; A61M 5/288; A61M 5/31596; A61M 5/321; A61M 5/3232; A61M 5/3234; A61M 5/3243; A61M 5/3245; A61M 5/326; A61M 5/3271; A61M 5/3293
See application file for complete search history.

(56) References Cited

U.S. PATENT DOCUMENTS

| | | | |
|---|---|---|---|
| 4,031,892 | A | 6/1977 | Hurschman |
| 4,060,082 | A | 11/1977 | Lindberg et al. |
| 4,529,403 | A | 7/1985 | Kamstra |
| 4,643,721 | A | 2/1987 | Brunet |
| 4,755,169 | A | 7/1988 | Samoff et al. |
| 5,360,410 | A | 11/1994 | Wacks |
| 5,569,193 | A | 10/1996 | Hofstetter et al. |
| 5,704,918 | A | 1/1998 | Higashikawa |
| 5,899,881 | A | 5/1999 | Grimard et al. |
| 6,149,628 | A | 11/2000 | Szapiro et al. |
| 6,309,372 | B1 | 10/2001 | Fischer et al. |
| 6,641,561 | B1 | 11/2003 | Hill et al. |
| 6,656,150 | B2 | 12/2003 | Hill et al. |
| 6,770,052 | B2 | 8/2004 | Hill et al. |
| 6,793,646 | B1 | 9/2004 | Giambattista et al. |
| 6,852,103 | B2 | 2/2005 | Fowles et al. |
| 6,953,445 | B2 | 10/2005 | Wilmot et al. |
| 7,449,012 | B2 | 11/2008 | Young et al. |
| 7,544,189 | B2 | 6/2009 | Griffiths |
| 7,556,614 | B2 | 7/2009 | Griffiths et al. |
| 7,608,055 | B2 | 10/2009 | Griffiths et al. |
| 7,612,887 | B2 | 11/2009 | Choi et al. |
| 7,621,887 | B2 | 11/2009 | Griffiths et al. |
| 7,678,073 | B2 | 3/2010 | Griffiths et al. |
| 7,749,190 | B2 | 7/2010 | Griffiths et al. |
| 7,757,370 | B2 | 7/2010 | Griffiths |
| 7,776,015 | B2 | 8/2010 | Sadowski et al. |
| 7,947,742 | B2 | 5/2011 | Batycky et al. |
| 8,057,427 | B2 | 11/2011 | Griffiths et al. |
| 8,092,420 | B2 | 1/2012 | Bendek et al. |
| 8,123,719 | B2 | 2/2012 | Edwards et al. |
| 8,177,758 | B2 | 5/2012 | Brooks, Jr. et al. |
| 8,187,220 | B2 | 5/2012 | Griffiths et al. |
| 8,251,947 | B2 | 8/2012 | Kramer et al. |
| 8,496,619 | B2 | 7/2013 | Kramer et al. |
| 8,506,526 | B2 | 8/2013 | Griffiths et al. |
| 8,568,367 | B2 | 10/2013 | Griffiths et al. |
| 8,613,720 | B2 | 12/2013 | Bendek et al. |
| 8,632,504 | B2 | 1/2014 | Young |
| RE44,847 | E | 4/2014 | Sadowski et al. |
| 8,696,618 | B2 | 4/2014 | Kramer et al. |
| 8,814,834 | B2 | 8/2014 | Sund et al. |
| 8,870,827 | B2 | 10/2014 | Young et al. |
| 8,945,053 | B2 | 2/2015 | Vogt et al. |
| 9,364,610 | B2 | 6/2016 | KraMer et al. |
| 9,364,611 | B2 | 6/2016 | KraMer et al. |
| 2002/0046563 | A1 | 2/2002 | Hill et al. |
| 2002/0042592 | A1 | 4/2002 | Wilmot et al. |
| 2002/0049406 | A1 | 4/2002 | Hill et al. |
| 2002/0049407 | A1 | 4/2002 | Hill et al. |
| 2005/0074498 | A1 | 4/2005 | Tarara et al. |
| 2005/0148933 | A1 | 7/2005 | Raven et al. |
| 2005/0177100 | A1 | 8/2005 | Harper et al. |
| 2006/0079834 | A1 | 4/2006 | Tennican et al. |
| 2007/0116729 | A1 | 5/2007 | Nageswara |
| 2007/0202163 | A1 | 8/2007 | Rawas-Qalaji et al. |
| 2007/0293582 | A1 | 12/2007 | Hill |
| 2008/0103490 | A1 | 5/2008 | Edwards et al. |
| 2008/0281271 | A1 | 11/2008 | Griffiths et al. |
| 2009/0171311 | A1 | 7/2009 | Genosar et al. |
| 2010/0228190 | A1 | 9/2010 | Griffiths et al. |
| 2010/0318035 | A1 | 12/2010 | Edwards et al. |
| 2011/0092906 | A1 | 4/2011 | Bottger et al. |
| 2011/0092917 | A1 | 4/2011 | Wei et al. |
| 2011/0237681 | A1 | 9/2011 | Patycky et al. |
| 2012/0016296 | A1 | 1/2012 | Charles |
| 2012/0130318 | A1 | 5/2012 | Young |
| 2012/0179137 | A1 | 7/2012 | Bartlett et al. |
| 2012/0302989 | A1 | 11/2012 | Kramer |
| 2013/0018310 | A1 | 1/2013 | Boyd |
| 2013/0023822 | A1 | 1/2013 | Edwards et al. |
| 2013/0060232 | A1 | 3/2013 | Adlon et al. |
| 2013/0018313 | A1 | 7/2013 | Kramer |
| 2013/0178823 | A1 | 7/2013 | Buchine |
| 2013/0274707 | A1 | 10/2013 | Wilmont et al. |
| 2013/0289791 | A1 | 10/2013 | Kerrigan et al. |
| 2013/0317477 | A1 | 11/2013 | Edwards et al. |
| 2013/0331788 | A1 | 12/2013 | Kramer et al. |
| 2014/0088512 | A1 | 3/2014 | Quinn |
| 2014/0276385 | A1 | 9/2014 | Buchine et al. |
| 2014/0276430 | A1 | 9/2014 | Baker et al. |
| 2014/0336589 | A1 | 11/2014 | Sund et al. |
| 2015/0011975 | A1 | 1/2015 | Anderson et al. |
| 2015/0174323 | A1 | 6/2015 | Edwards et al. |
| 2015/0367073 | A1 | 12/2015 | Standley et al. |
| 2015/0374925 | A1 | 12/2015 | Standley et al. |
| 2016/0220764 | A1 | 8/2016 | Durvasula et al. |

FOREIGN PATENT DOCUMENTS

| | | |
|---|---|---|
| WO | WO9208506 A1 | 5/1992 |
| WO | WO2008114035 A1 | 9/2008 |
| WO | WO2008154092 A1 | 12/2008 |
| WO | WO2005032523 A2 | 1/2009 |
| WO | WO2009118754 A2 | 10/2009 |
| WO | WO2010068415 A1 | 6/2010 |
| WO | WO2011060541 A1 | 5/2011 |
| WO | WO2011109340 A1 | 9/2011 |
| WO | WO2012090168 A1 | 5/2012 |
| WO | WO2012099898 A2 | 7/2012 |
| WO | WO2013063707 A1 | 5/2013 |
| WO | WO2014026694 | 2/2014 |

(56) References Cited

FOREIGN PATENT DOCUMENTS

| WO | WO20140605633 | 4/2014 |
| WO | WO201466731 | 5/2014 |
| WO | WO14205463 | 12/2014 |

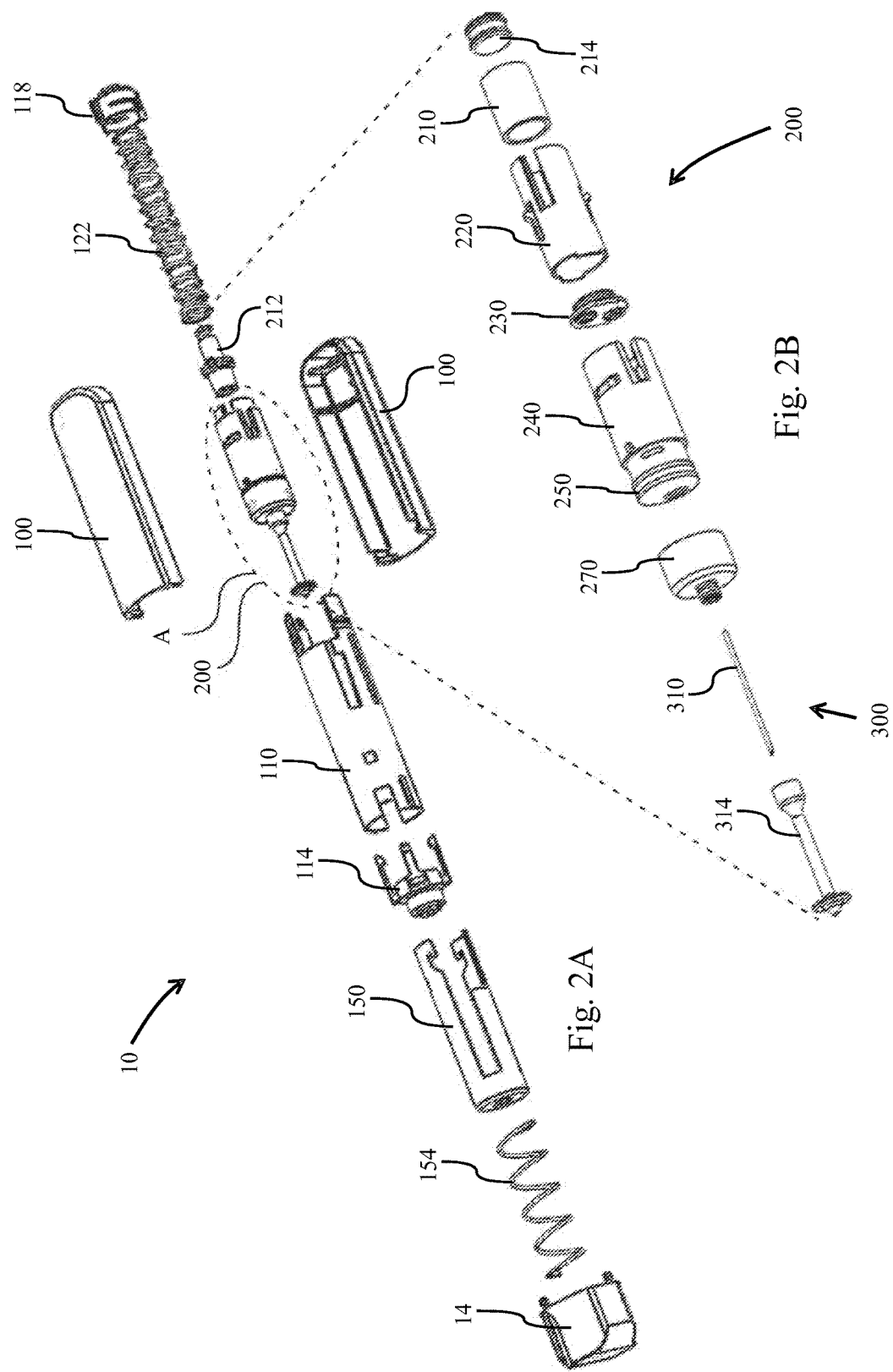

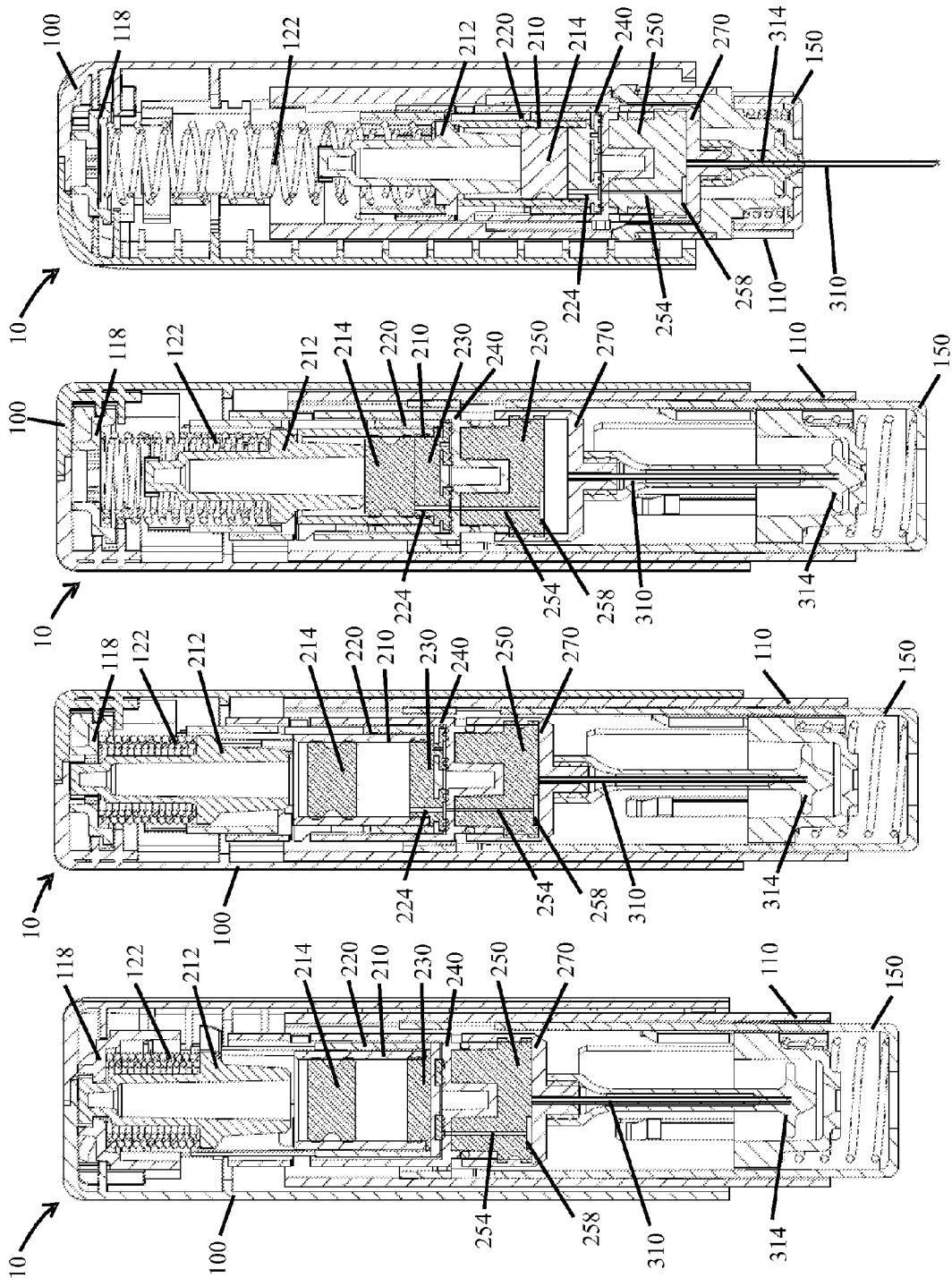

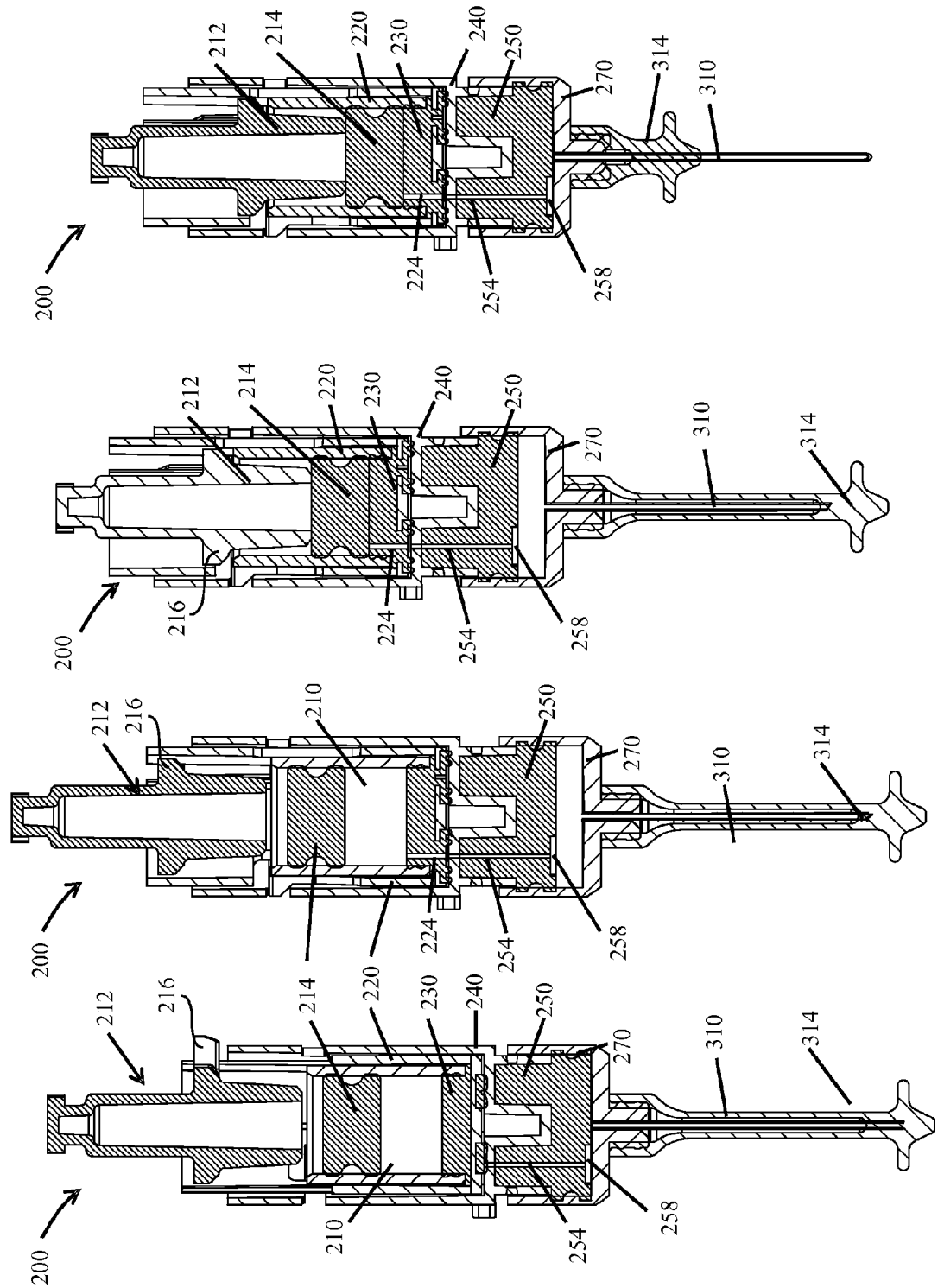

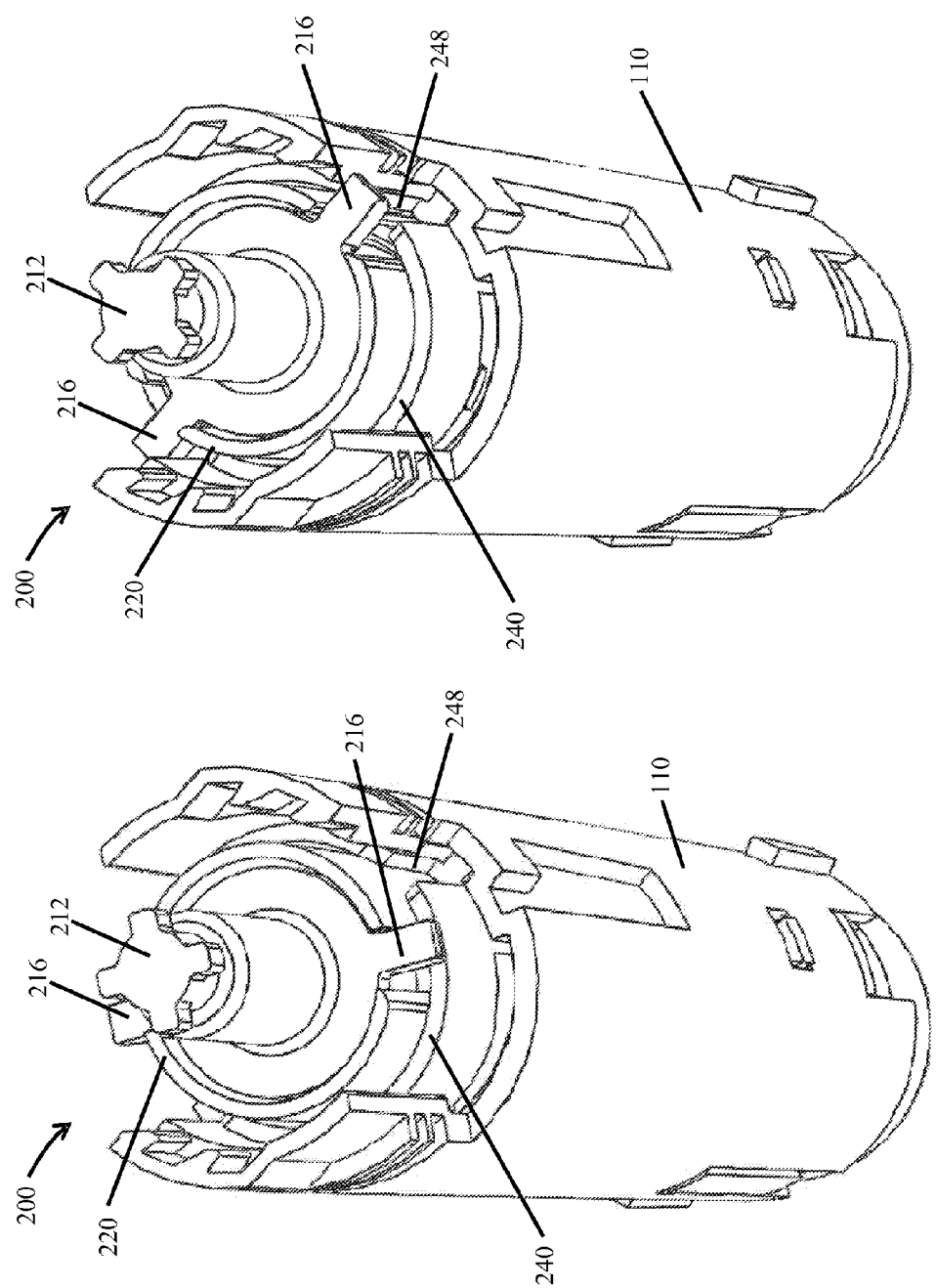

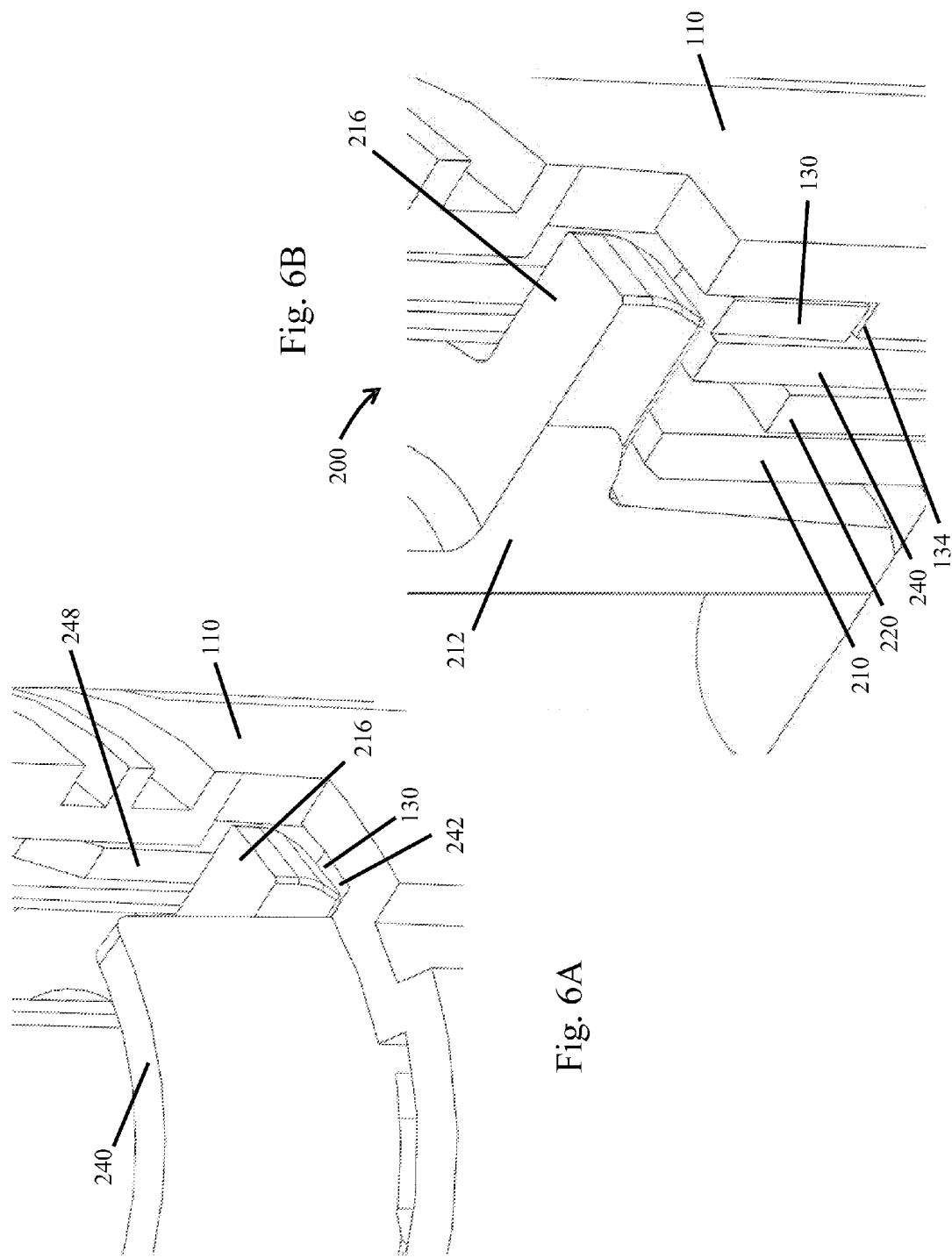

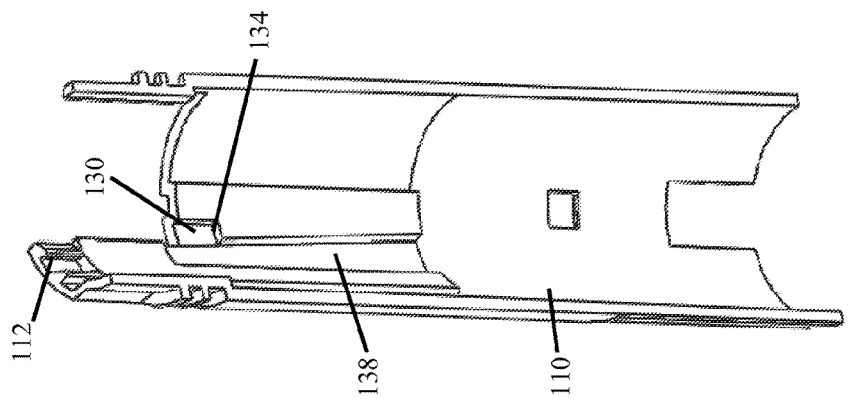
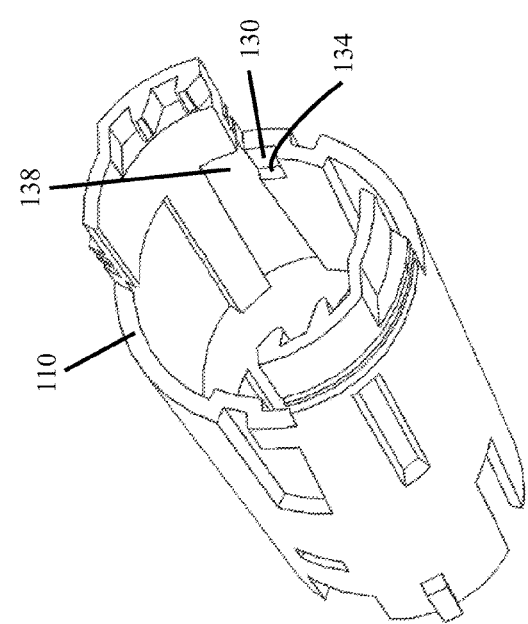
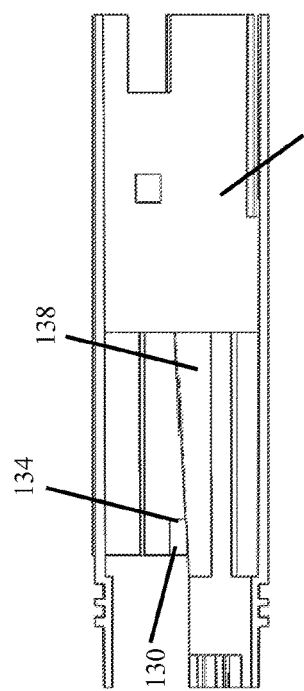
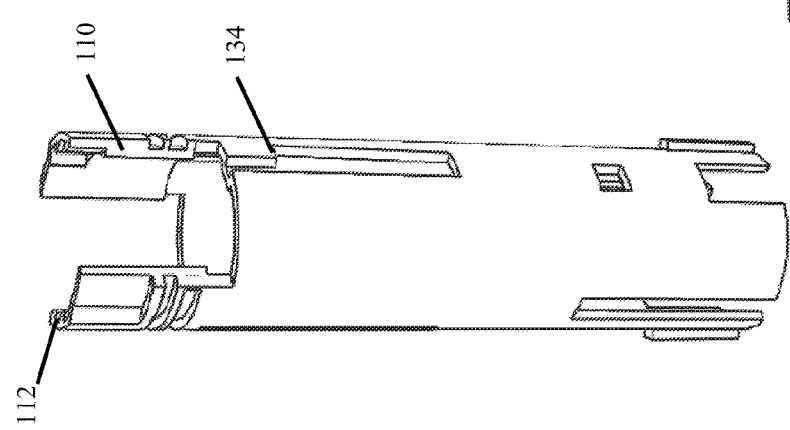

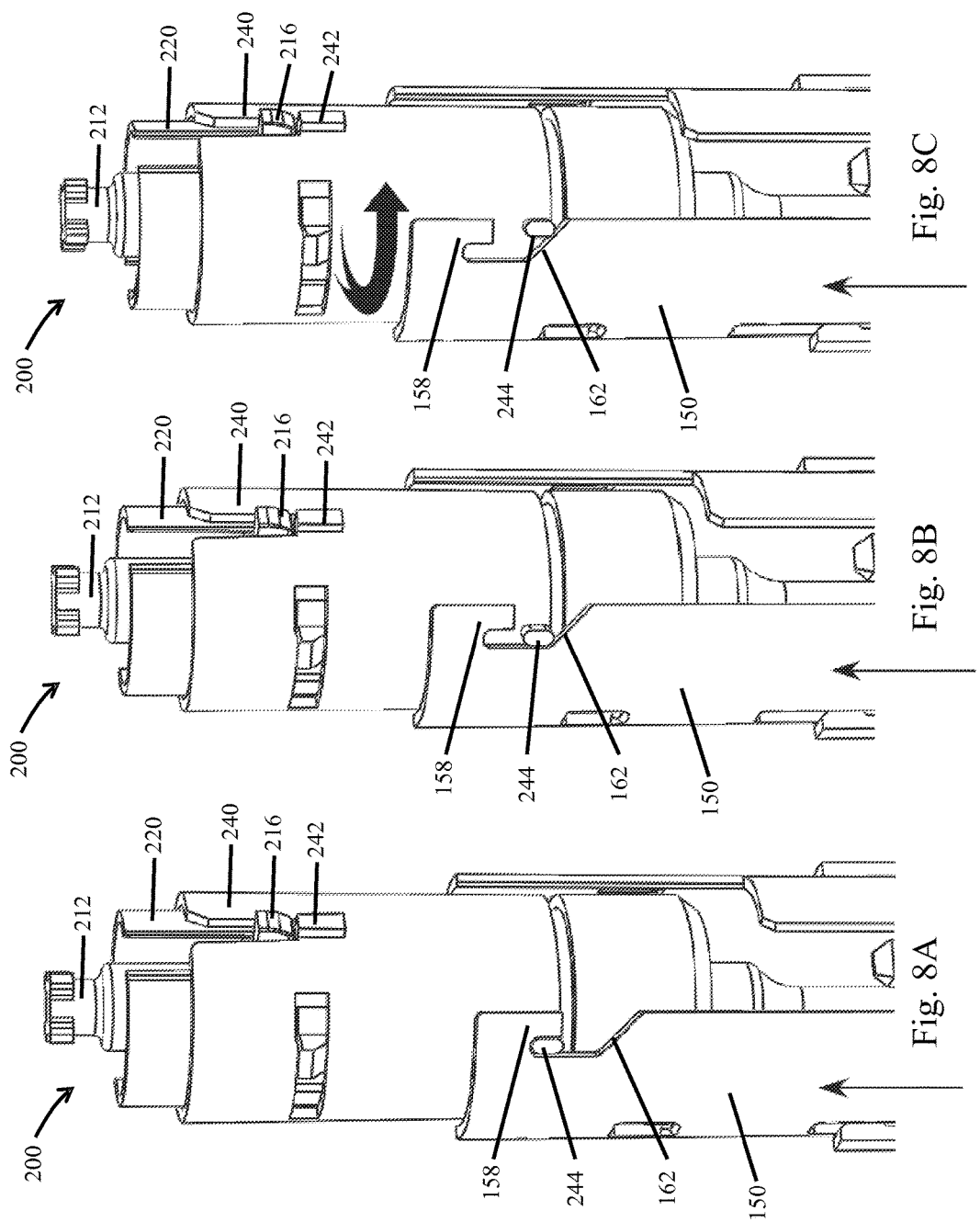

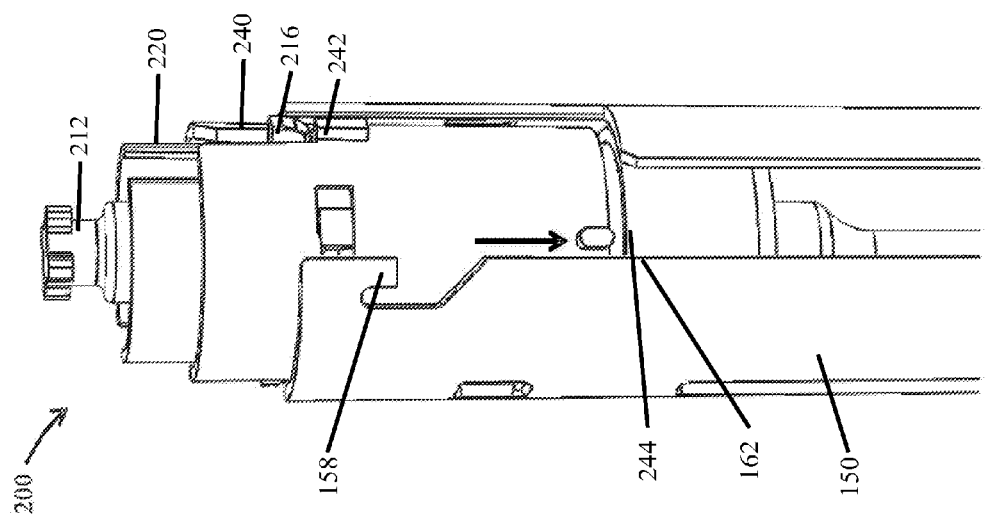
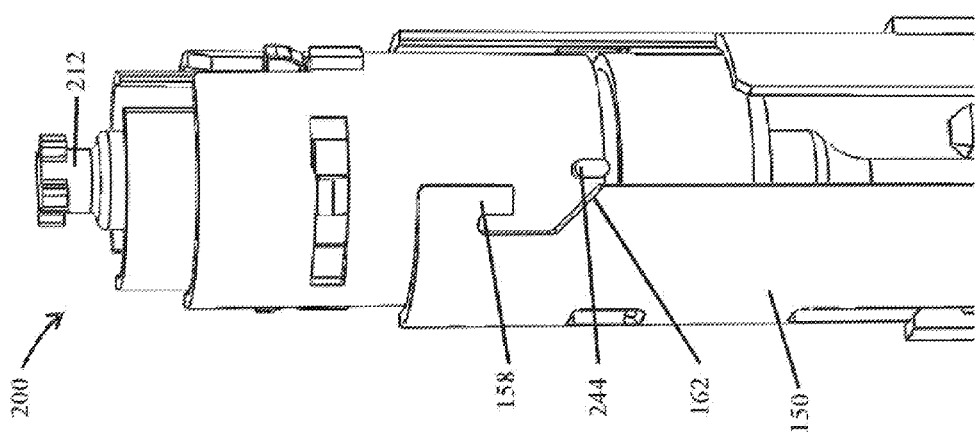

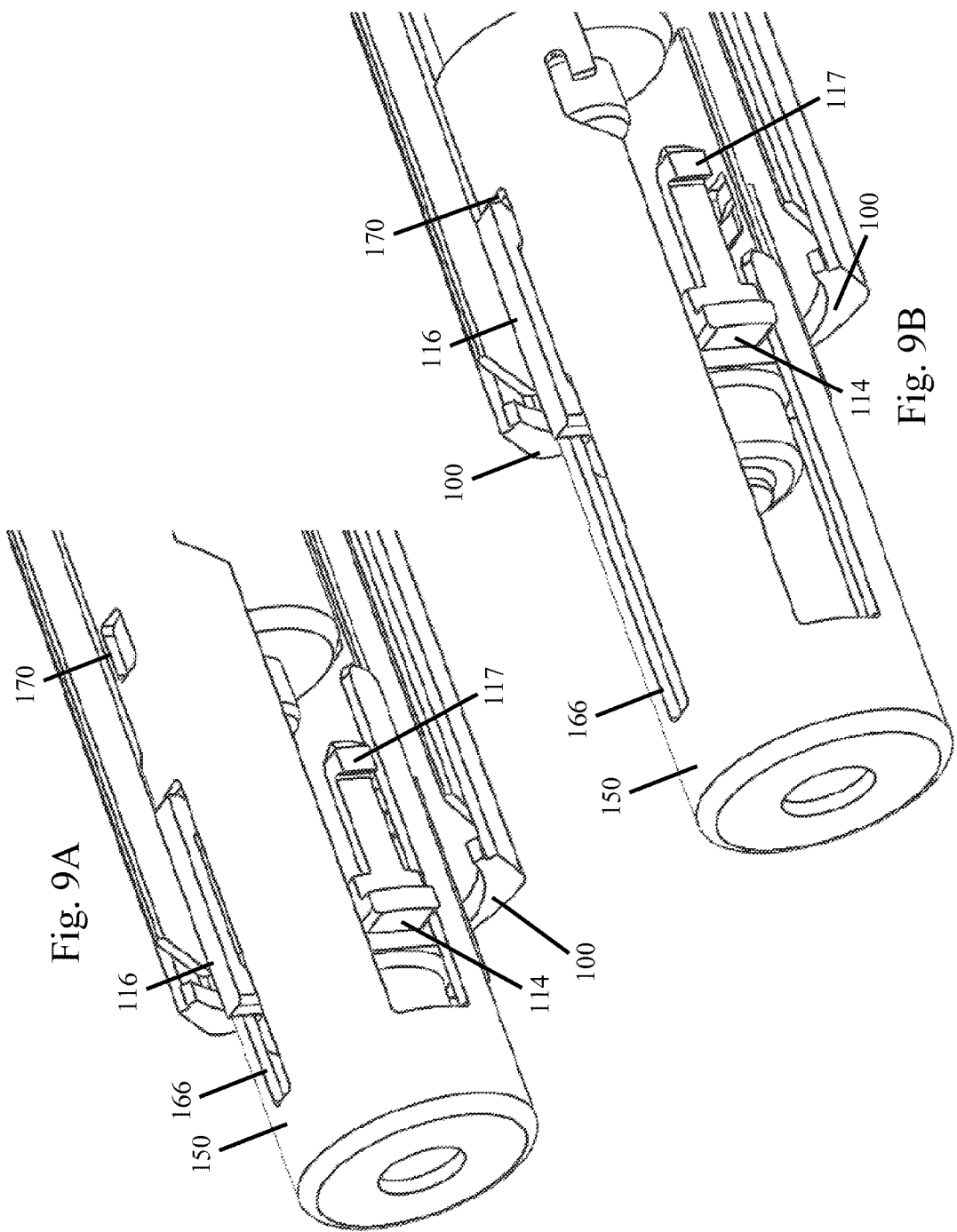

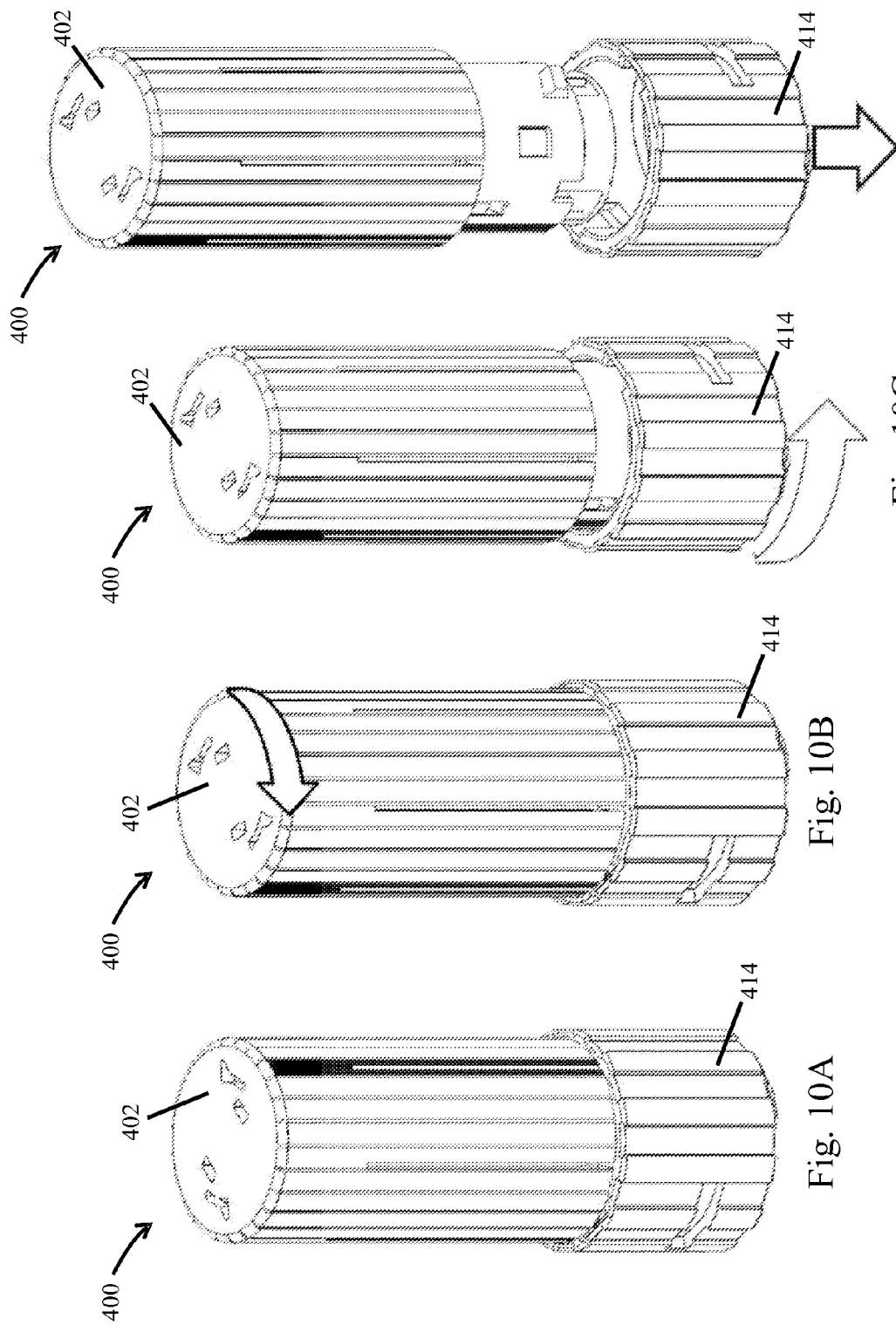

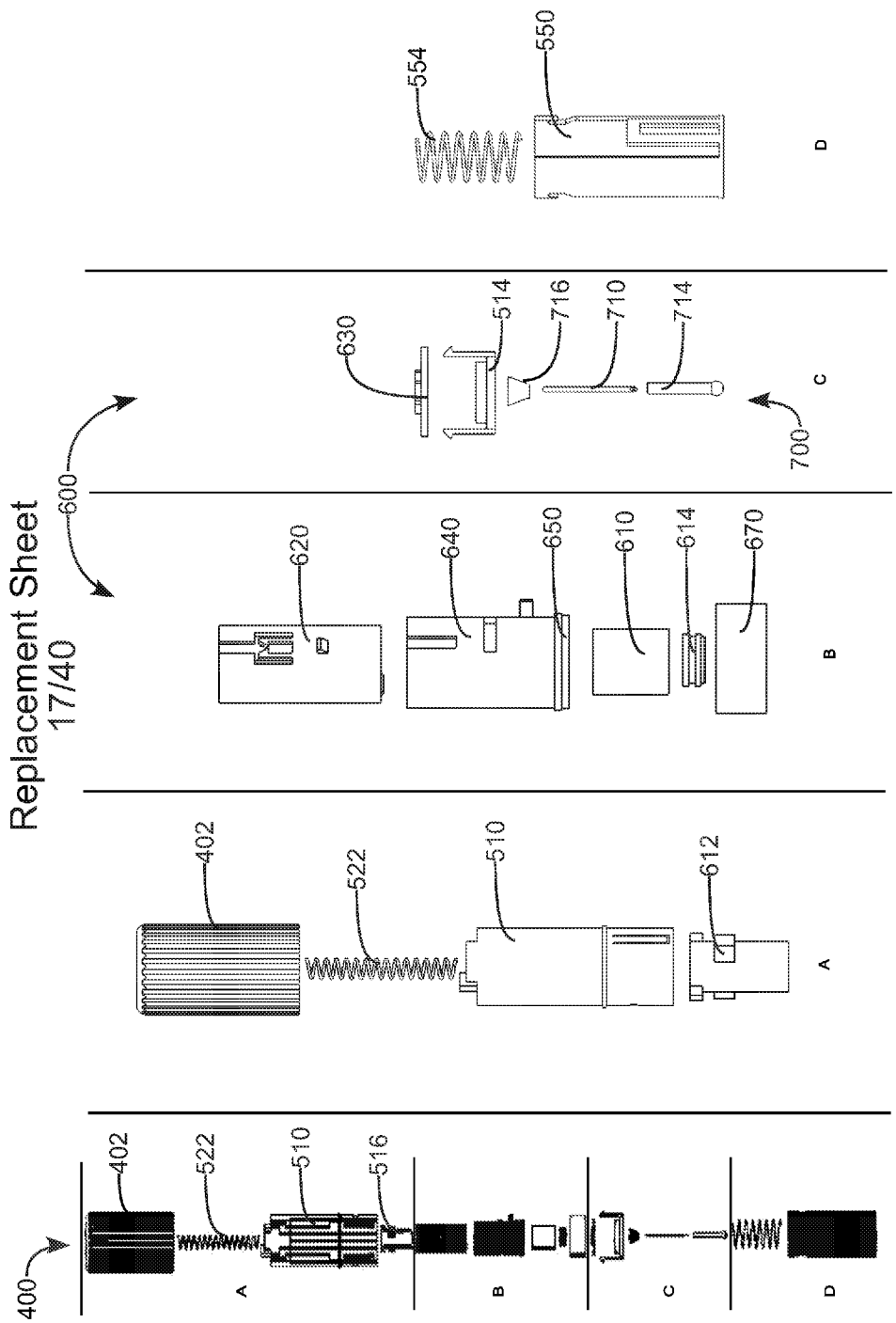

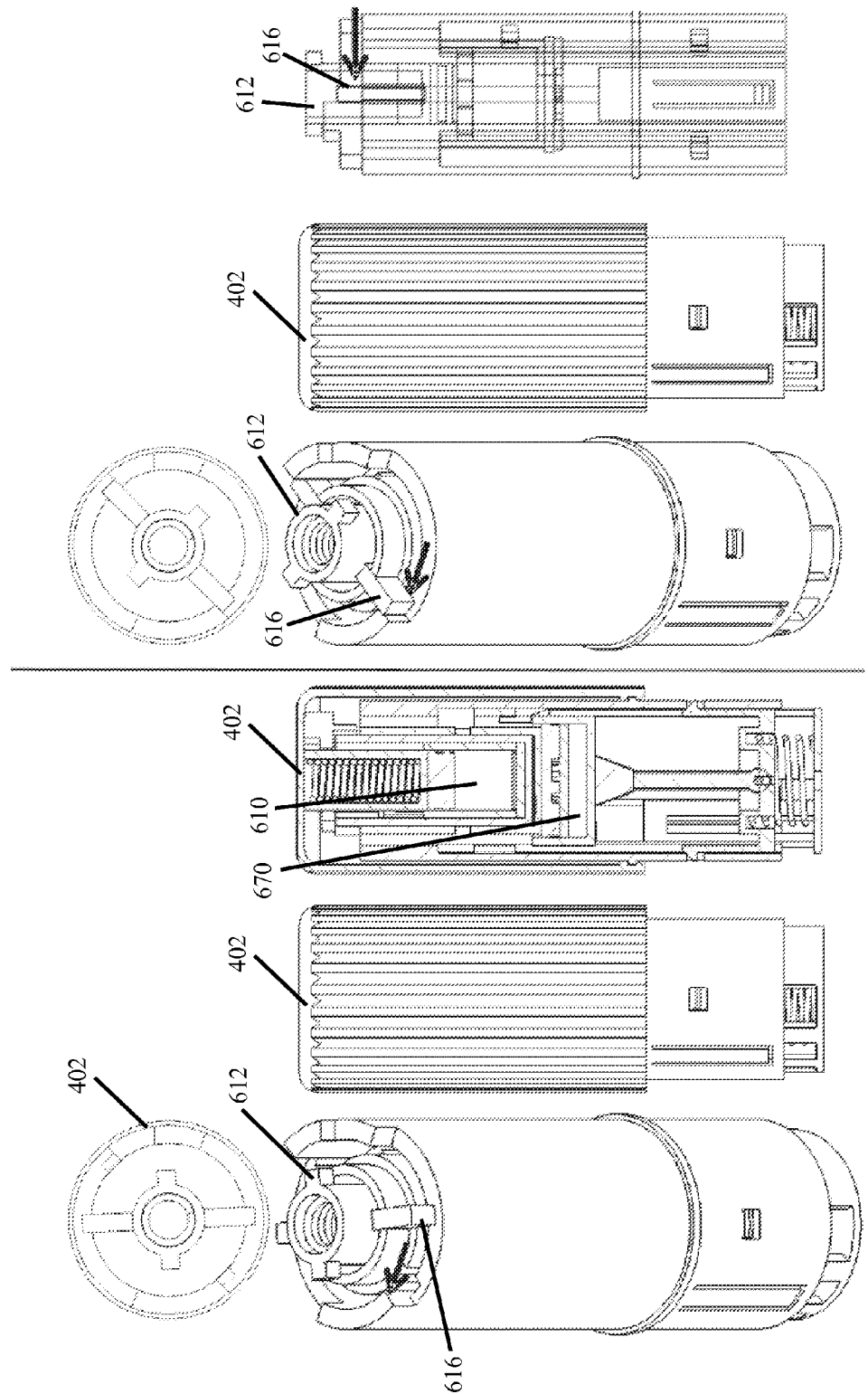

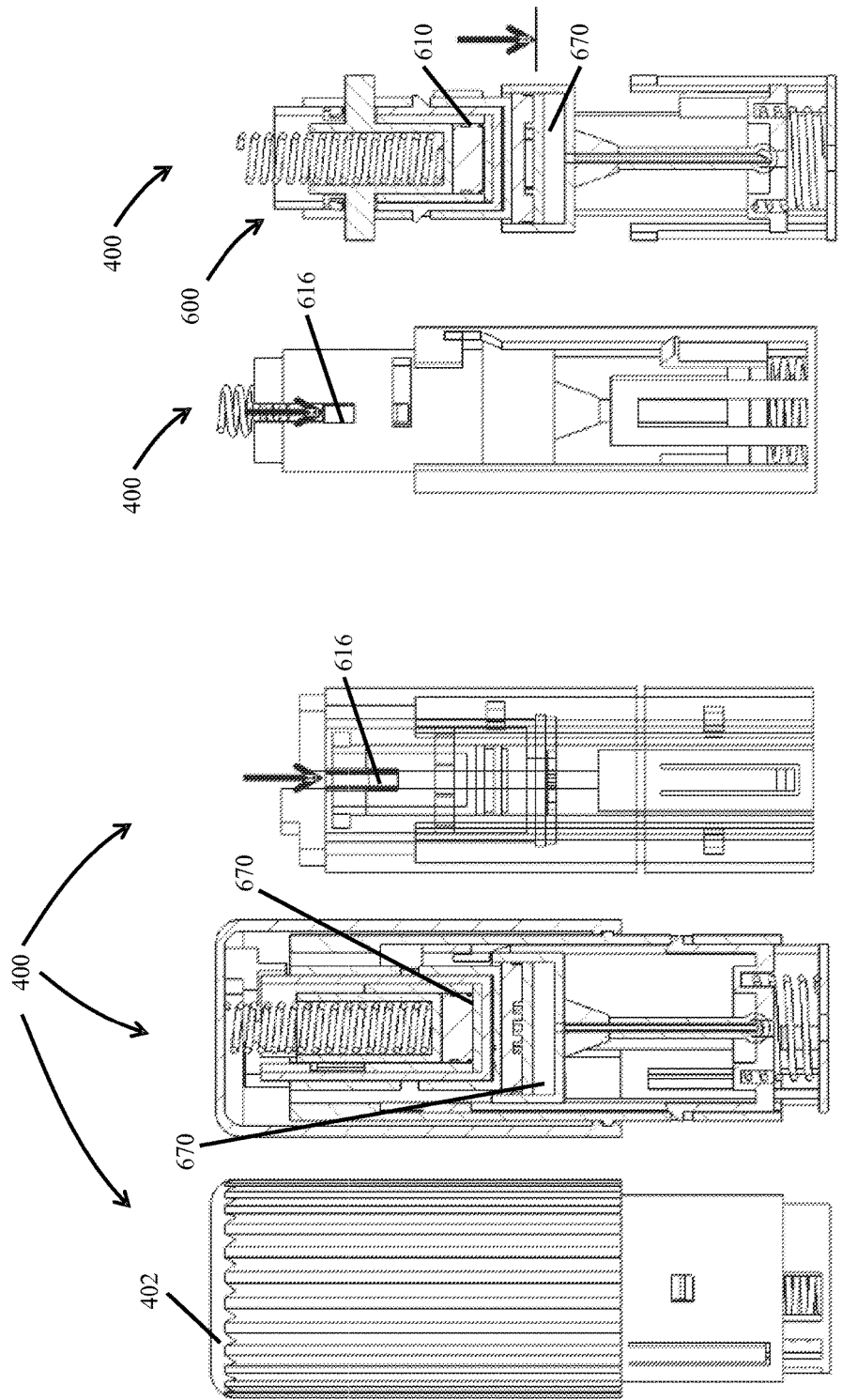

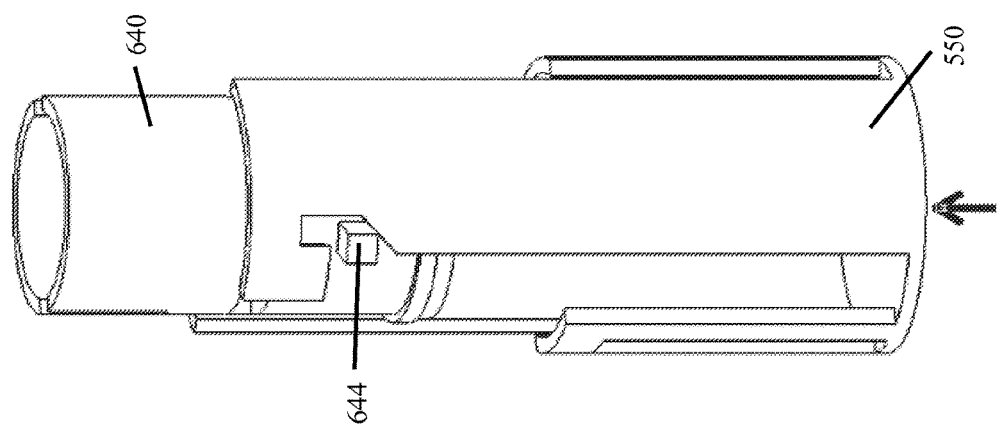
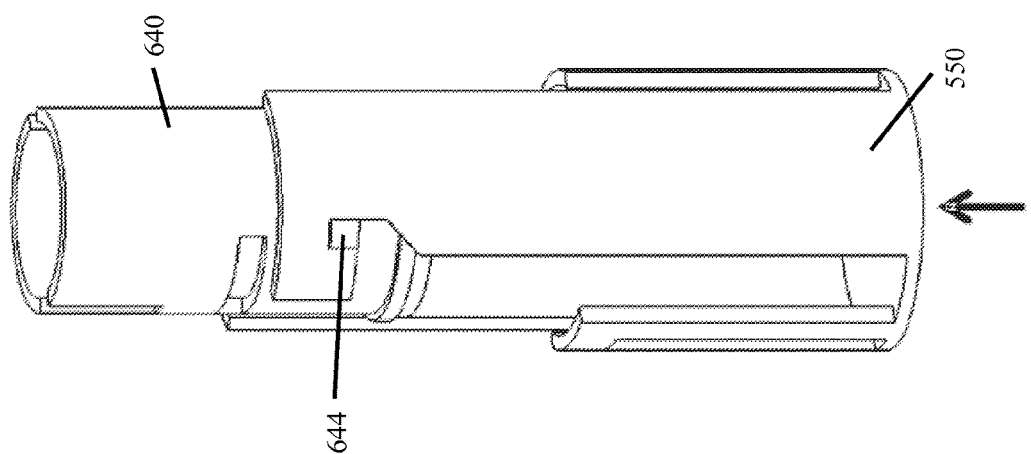

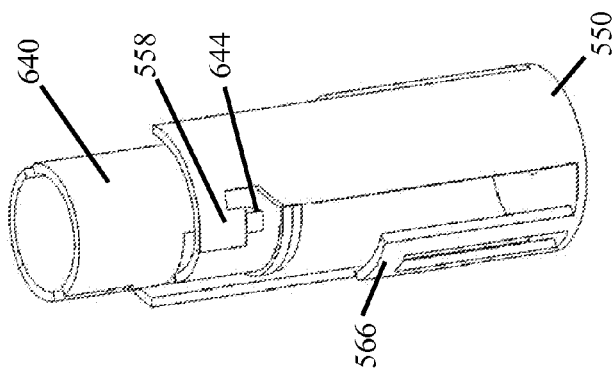
FIG. 20D
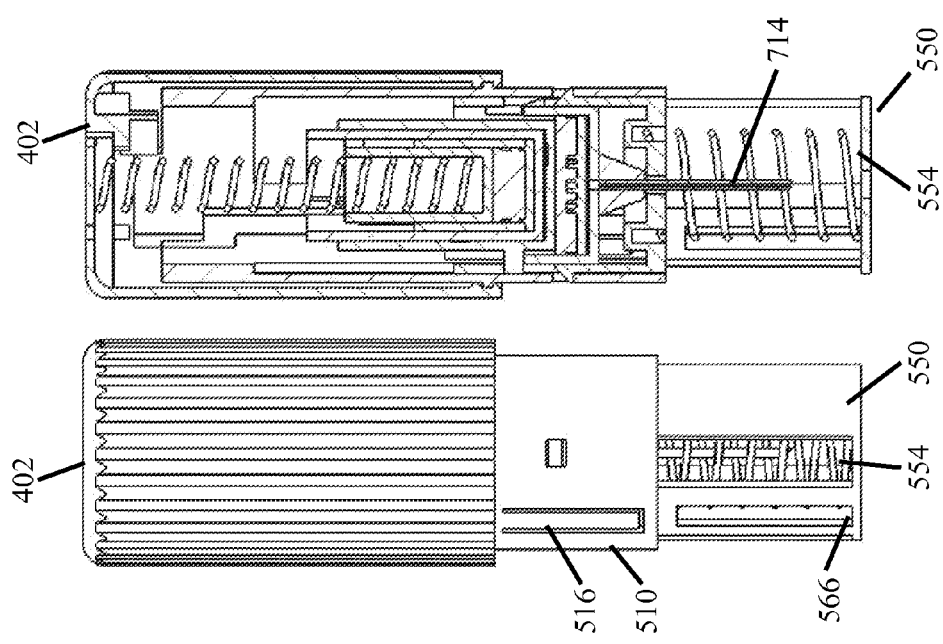
FIG. 20C
FIG. 20B
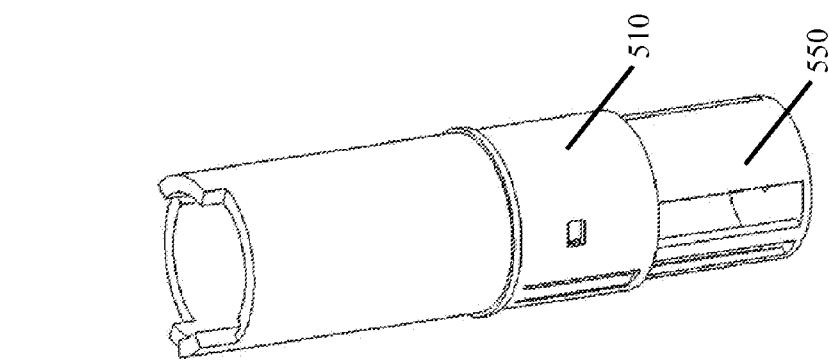
FIG. 20A

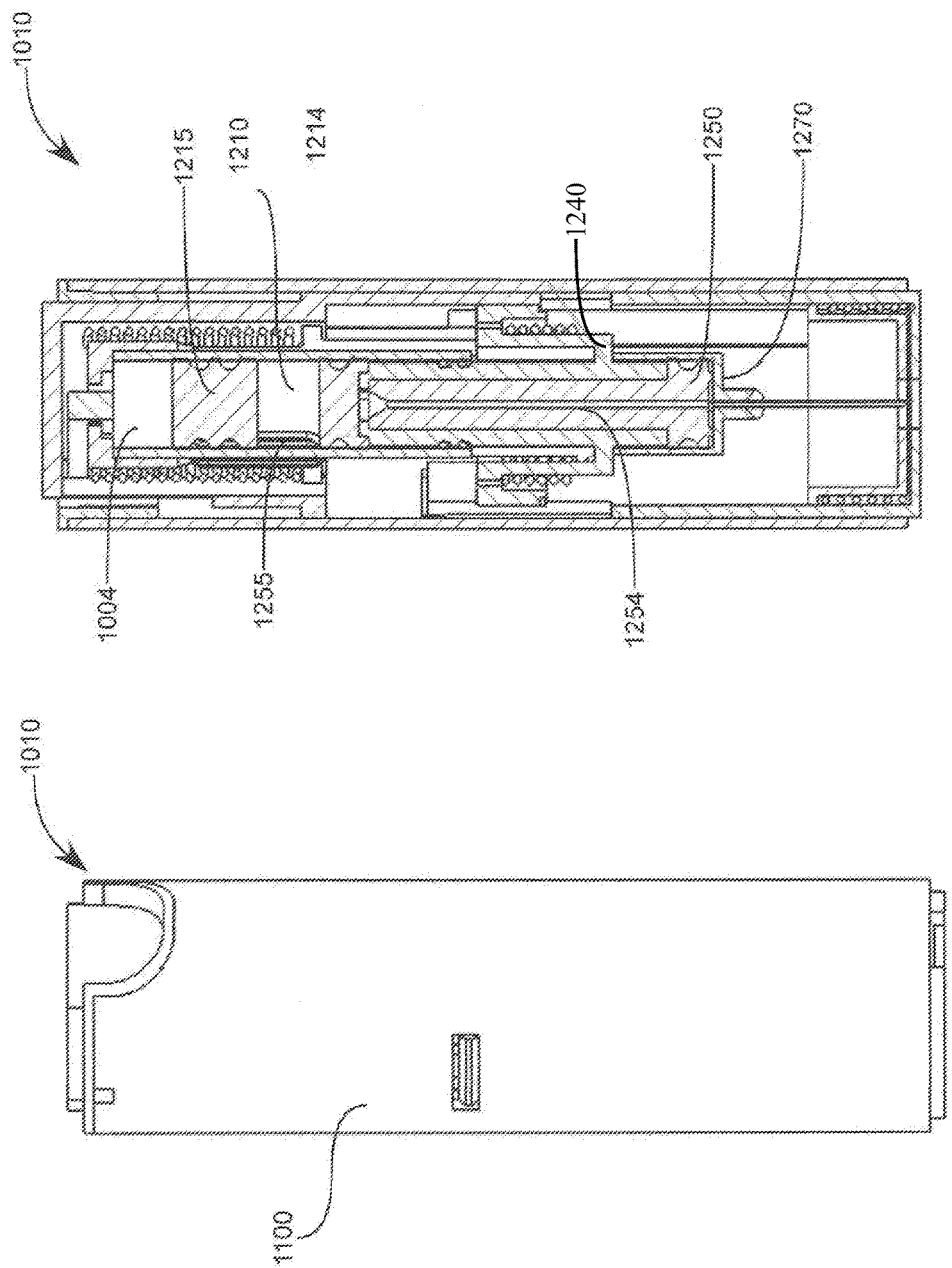

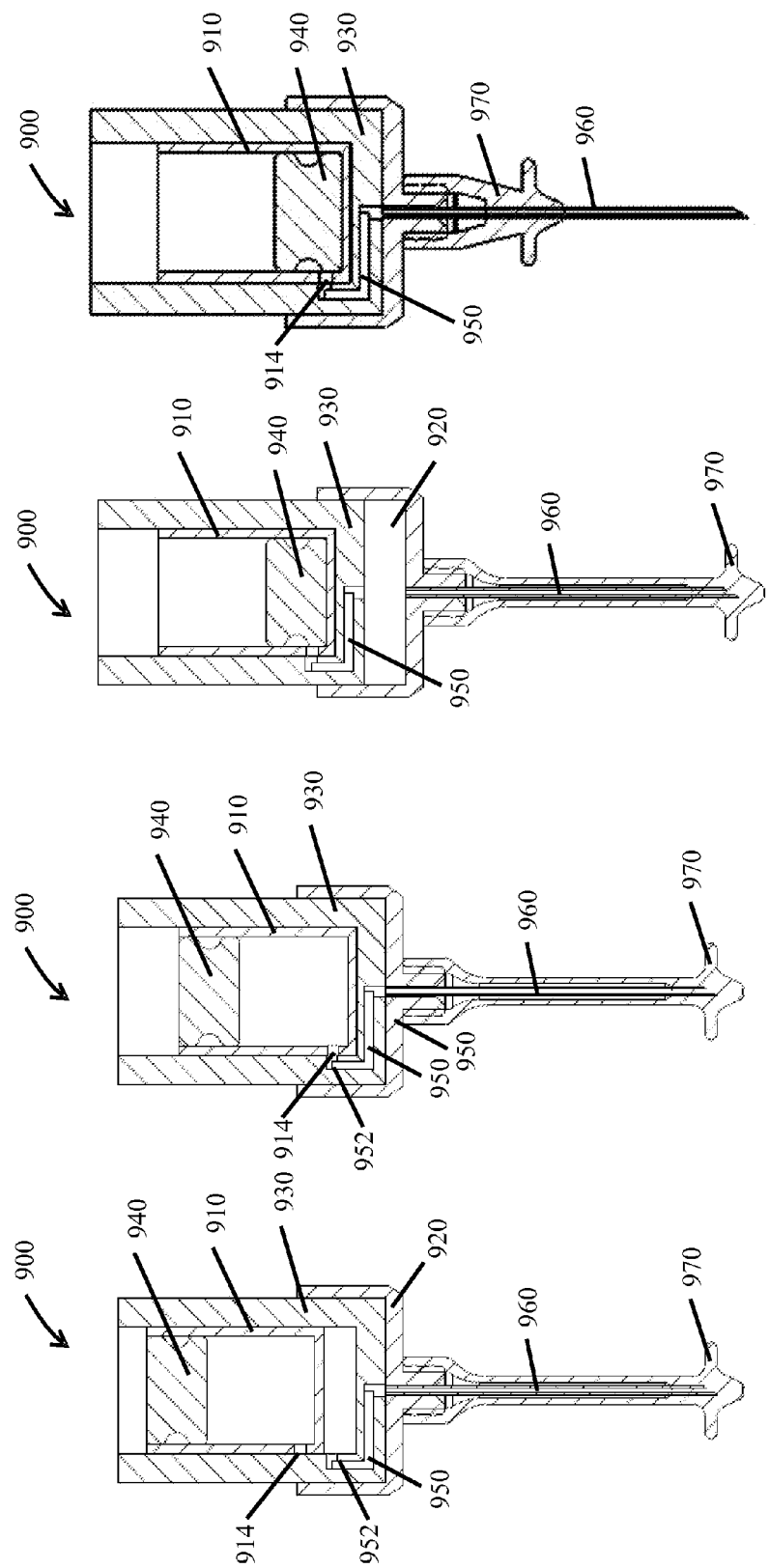

PORTABLE DRUG MIXING AND DELIVERY DEVICE AND ASSOCIATED METHODS

CROSS-REFERENCE TO RELATED APPLICATIONS

This application claims the benefit of U.S. Patent Application No. 62/038,386 filed on Aug. 18, 2014; U.S. Patent Application No. 62/126,011 filed on Feb. 27, 2015; U.S. Patent Application No. 62/204,940 filed on Aug. 13, 2015; U.S. Patent Application No. 62/061,664 filed on Oct. 8, 2014; U.S. Patent Application No. 62/120,792 filed on Feb. 25, 2015 which are herein incorporated by reference in their entirety.

FIELD OF THE INVENTION

The present invention relates generally to auto-injectors and prefilled syringes and more particularly to auto-injectors that store in a compact state and allow for formation or reconstitution of a therapeutic agent for injection.

BACKGROUND OF THE INVENTION

Individuals who suffer from certain medical conditions are often required to keep an auto-injector or prefilled syringe nearby in order to address a medical need. A few examples of this are insulin pens for people with diabetes, epinephrine for those with food and insect stings allergies, and antidotes for soldiers at risk of exposure to chemical and/or biological toxins in the field. For example, an allergic reaction may occur in a location which is physically distant from the nearest hospital or medical facility. For example, bee stings, are more likely to occur outside than indoors. Food containing peanuts are more likely to be supplied to the individual away from a controlled home environment like at a baseball park. Having a portable epinephrine auto-injector nearby enables emergency intervention after an exposure to an allergen.

Size is an issue when it comes to auto-injectors. Many owners of the devices are hesitant to carry their injector with them if it represents a burden, by providing injectors in more compact sizes it will make it more likely that they will.

Shelf-life is also a large issue with respect to auto-injectors, which can be expensive and used fairly infrequently. For example a user who has intense allergic reactions to shellfish can go years between exposures and subsequent injections. In such a case it can be easy to forget to replace the auto-injector after expiration, whereupon in an emergency, the drugs contained therein have expired and are either ineffective or have a greatly reduced effectiveness due to decomposition of the drugs contained therein. As will be appreciated by those having skill in the art, the shelf life can be increased by storing the desired medication in an unmixed and dry state and dissolved just prior to injection. This ability to store the wet and dry components separately within the device can increase the shelf life and thus increase the likelihood that the user will have an injector with effective dosages when an emergency arises.

In such devices it is required that the mixing and reconstitution processes are consistent and complete prior to injection.

SUMMARY OF THE INVENTION

It has been recognized that if a drug can be kept out of the liquid phase and stored as a dry medication, the shelf-life can be substantially increased and temperature susceptibility can be decreased substantially, thus allowing the efficacy and potency of the drug to endure longer and through harsher environments.

It has been recognized that a smaller drug delivery device than a conventional epinephrine auto-injector, which could be attached to a key chain and/or easily fit in a person's pocket, would make the device easier to carry and more likely that the user will have it on their person when needed. Various structures are contemplated herein which address many of the problems discussed above through the use of mixing structures, and actuation devices which ensure proper storage integrity, and full mixing prior to injection.

Contemplated herein is a medication mixing and delivery device which includes a housing. The housing can then contain a first chamber the first chamber, which can be defined by an annular side wall and a bottom, the first chamber also having an outlet. The housing can also contain a second chamber, the second chamber having an inlet. A rotary valve can also be located within the housing, the rotary valve being selectively opened or closed by aligning or misaligning the outlet of the first chamber to cause or prevent fluid communication between the outlet of the first chamber and the inlet of the second chamber.

A pre-loaded energy source can be provided within the housing and also be configured to respond to an actuation device, the actuation device also being in mechanical communication with the rotary valve so as to move the rotary valve between a closed and open state. The pre-loaded energy source can further be coupled to a displacement mechanism, such as a plunger, which is configured to reduce the effective volume of the first chamber. The actuation device can be configured to be activated by means of an axial torsional force, wherein the axial torsional force causes the rotary valve to be placed into the open state and wherein the axial torsional force causes a first portion of energy stored within the pre-stored energy source to be released and cause the displacement mechanism to force a liquid stored in the first chamber to pass through the outlet and inlet to be received by the second chamber, wherein a dry medicament is stored within the housing and outside the first chamber, such as in the fluidic channel between the first and second chambers, or alternatively, within the second chamber itself The medication mixing and delivery device can also include a second actuation device, i.e. a second plunger, which is configured to release a second portion of energy from the pre-loaded energy source into a second displacement mechanism configured to reduce the effective volume of the second chamber, which, upon release forces the liquid, which is now located in the second liquid chamber, to be displaced out of the second chamber through the delivery assembly. A delivery assembly can then be connected to, and provided in fluid communication with, the second chamber can then be configured to provide appropriate delivery of the mixed drug and liquid component to a delivery site, for example, injected, nebulized, etc.

In particular, the delivery mechanism can include a needle assembly which is partially disposed within a septum, wherein the septum is disposed between the needle assembly and the second chamber. In such a case the second actuation device can be configured to cause the needle assembly to pierce the septum and allow the needle assembly to be in fluid communication with the second chamber. Alternatively, the delivery mechanism can include a blocking mechanism disposed between the second chamber and the delivery mechanism, and wherein the blocking mechanism prevents fluid communication prior to activating the second actuation device.

In some embodiments the first actuation device is formed in part by the housing and a rotatable cap, wherein the rotatable cap is removably attached to the housing.

In yet other embodiments the first chamber can be rotatable with respect to the housing.

In yet additional embodiments the second chamber can be configured such that it becomes rotationally fixed with the first chamber upon releasing the first portion of stored energy. Or alternatively the second chamber can be configured such that it becomes rotationally fixed with the first chamber upon releasing the first portion of stored energy and wherein the first and second chamber rotate together upon activating the second actuation device.

In yet alternative embodiments the second chamber can be configured such that the second chamber is independently expandable and contractible with respect to the first chamber.

In certain alternative embodiments the pre-loaded energy source can be provided as a compressed spring or compressed gas.

In certain alternative embodiments the second chamber can also be provided with a removable ferrule disposed therein about the inlet.

In certain alternative embodiments a fluidic channel can be provided which is disposed between the outlet of the first chamber and the inlet of the second chamber, where the fluidic channel is comprised of a plurality of stacked disks, and wherein each disk forms part of the fluidic channel.

In yet additional embodiments the device can include a needle shield assembly, the needle shield assembly further comprising a needle shield and a secondary spring, the secondary spring biasing the needle shield in an extended position. In some of these embodiments the needle shield can be configured such that it forms a part of a second actuation assembly, the second actuation device being configured to release a second portion of energy from the pre-loaded energy source which upon release forces the liquid, which is now located in the second liquid chamber, to be displaced out of the second chamber through the delivery assembly, and whereupon depressing the needle shield toward the housing triggers the release of the second portion of energy stored within the pre-stored energy source, which release causes both an extension of the delivery assembly and the displacement of the liquid from the second chamber through the delivery assembly. In some of these embodiments the needle shield assembly can further include a locking mechanism, which is triggered after a first needle shield depression, and wherein the locking mechanism configured to lock in an extended position after being removed from an injection site.

In yet alternative embodiments contemplated herein, the medication delivery device can include a housing, a chamber containing a liquid, disposed within the housing, and a delivery assembly configured to be in fluid communication with the chamber. This alternative embodiment can further include a needle shield assembly which can be attached to the housing and disposed at least partially around the delivery assembly, the needle shield assembly further including a needle shield and secondary spring, the secondary spring biasing the needle shield in an extended position. The needle shield can form part of an actuation assembly, the actuation assembly being configured to release a portion of energy from a pre-loaded energy source, which upon release, forces the liquid to be displaced out of the chamber through the delivery assembly, and whereupon depressing the needle shield toward the housing triggers the release of the portion of energy stored within the pre-stored energy source, which release causes both an extension of the delivery assembly and the displacement of the liquid from the chamber through the delivery assembly. The needle shield assembly can further include a locking mechanism, which is triggered after the needle shield depression, and which is configured to lock in the extended position.

In some embodiments the mixing device can include one or more cam ramps provided in a sidewall of the needle shield, wherein the cam ramps are in mechanical communication with the actuation assembly.

In some of these embodiments an intermediate support can be provided which is in mechanical communication with the actuation assembly, and wherein the intermediate support engages with the cam ramp. In some of these embodiments the intermediate support can be further provided with a protrusion extending from a sidewall which engages the cam ramp.

Also contemplated herein is a method of mixing and delivering a medication, the method including various steps, such steps including: coupling a pre-stored energy source to a first actuation mechanism, wherein actuation releases a first portion of stored energy from the pre-stored energy source to activate a first displacement mechanism which forces a fluid stored in a first chamber to be displaced into a second chamber; coupling a rotary valve to the first actuation mechanism, whereupon actuation causes the rotary valve to change from a closed state to an open state by rotating an outlet of the first chamber such that it becomes aligned and in fluid communication with an inlet of the second chamber; applying an axial torsional force between a housing and a cap, which said housing and cap form part of the first actuation mechanism, and wherein said force causes the actuation that releases a first portion of stored energy; activating a second actuation mechanism, whereupon actuation releases a second portion of stored energy from the pre-stored energy source so as to activate a second displacement mechanism which forces the fluid from the second chamber through a delivery mechanism.

In some of the method embodiments, the method can further include: placing a dry medicament within the second chamber, wherein activating the first actuation mechanism causes a fluid to mix with the dry medicament; extending the delivery mechanism in response to activating the second actuation mechanism. In some of these embodiments the activation of the second actuation mechanism can be effectuated by depressing a needle guard. Additionally, after delivery of the fluid through the delivery mechanism, the needle guard extends and locks into an extended state which covers a needle of the delivery assembly.

These aspects of the invention are not meant to be exclusive and other features, aspects, and advantages of the present invention will be readily apparent to those of ordinary skill in the art when read in conjunction with the following description, appended claims, and accompanying drawings. Further, it will be appreciated that any of the various features, structures, steps, or other aspects discussed herein are for purposes of illustration only, any of which can be applied in any combination with any such features as discussed in alternative embodiments, as appropriate.

BRIEF DESCRIPTION OF THE DRAWINGS

The foregoing and other objects, features, and advantages of the invention will be apparent from the following description of particular embodiments of the invention, as illustrated in the accompanying drawings in which like reference characters refer to the same parts throughout the different views. The drawings are not necessarily to scale, emphasis instead being placed upon illustrating the principles of the invention, wherein:

FIGS. 2A-B illustrate perspective exploded views of the medication mixing and delivery device and a mixing subassembly in accordance with the embodiment of FIGS. 1A-C;

FIGS. 3A-D illustrate side cross sectional views of a medication mixing and delivery device through various actuation steps in accordance with the embodiment of FIGS. 1A-C;

FIGS. 4A-D illustrate side cross sectional views of the mixing subassembly through various actuation steps for use in conjunction within the embodiment of FIGS. 1A-C;

FIGS. 5A-E illustrate various exterior perspective views of the mixing subassembly through various actuation steps moving from a stowed state to a mixed state as would be effectuated using the embodiment of FIGS. 1A-C;

FIGS. 6A-E illustrate various exterior perspective views and cross sectional views of the enlarged area of the mixing subassembly as indicated by area A in FIG. 5E;

FIGS. 7A-D illustrate various perspective and cross sectional views of a frame being used within the medication mixing and delivery device of FIGS. 1A-C;

FIGS. 8A-E illustrate various exterior perspective views of the mixing subassembly and a secondary actuation mechanism through various actuation steps moving from the mixed state to an injected state as would be effectuated using the embodiment of FIGS. 1A-C;

FIGS. 9A-B illustrate various exterior perspective views of a needle guard and associated subassembly through various actuation steps to shield an exposed needle after injection using the embodiment of FIGS. 1A-C;

FIGS. 10A-D illustrate perspective exterior views of an alternative embodiment of a medication mixing and delivery device through various actuation steps;

FIGS. 12A-E illustrate side exterior exploded views of the medication mixing and delivery device, a housing assembly, a mixing assembly, a delivery assembly and a needle guard assembly, respectively;

FIGS. 14A-C illustrate various exterior perspective, side, and cross sectional views of the medication mixing and delivery device as embodied in FIGS. 10A-D illustrating a first actuation step so as to initiate mixing;

FIGS. 15A-C illustrate various exterior perspective, side, and cross sectional views of the medication mixing and delivery device as embodied in FIGS. 10A-D illustrating an actuated state;

FIGS. 16A-C illustrate various side, cross sectional, and partially transparent views of the medication mixing and delivery device as embodied in FIGS. 10A-D illustrating a mixed state;

FIGS. 17A-B illustrate side and cross sectional views of the medication mixing and delivery device as embodied in FIGS. 10A-D illustrating an injection ready state;

FIGS. 18A-D illustrate various perspective views of a second actuation mechanism of the medication mixing and delivery device as embodied in FIGS. 10A-D illustrating changing from the mixed state to an injected state;

FIGS. 20A-D illustrate various perspective, side and cross sectional views of the medication mixing and delivery device as embodied in FIGS. 10A-D illustrating a needle shield lockout mechanism;

FIGS. 21A-B illustrate a perspective and cross sectional view, respectively, of yet another alternative embodiment of a medication mixing and delivery device in a stowed state;

FIGS. 27A-D illustrate principles of a sliding valve adaptable for use in any of the embodiments discussed herein;

DETAILED DESCRIPTION OF THE INVENTION

It will be appreciated by those having skill in the area of fabrication and storage of drugs, that the lifespan and effectiveness of the drug can be increased substantially by keeping the medication in a dry state. Storage in a dry state also decreases the rate of degeneration as well as the degenerative effects of temperature, for example heat exposure. By keeping the drug in a dry state the breadth of environments where the device can be stored is increased while decreasing the frequency of required replacement.

The present invention illustrates various principles and devices which allow for the storage of a device having two or more components contained therein but which can quickly and reliably reconstitute, dissolve, fluidize, and/or put into a suspension, the components, i.e. mix them, immediately prior to delivery.

As such a system and method for storing and/or mixing a dry medicament component with a wet component for delivery to a user is contemplated herein. The system can include an auto-injector having various chambers therein, wherein the components of the drug are stored separately within the various chambers in various states so as to increase longevity, i.e. a dry drug component in one chamber, and a liquid, such as a solvent, in another. When the auto-injector is needed, the system can be actuated so as to mix the components, thus reconstituting, dissolving, fluidizing, and/or suspending a deliverable mixed drug, wherein the mixed drug can then be properly delivered to a patient. Examples of delivery can include, but are not limited to nebulization for inhalation, injection through a needle or cannula, topical application, etc.

With reference to FIGS. 1-9, shown is an exemplary embodiment of an auto-injector 10 in accordance with a first embodiment. The auto-injector 10 illustrates various aspects of the present invention, each of which will be discussed in more detail below.

Figure 1C:
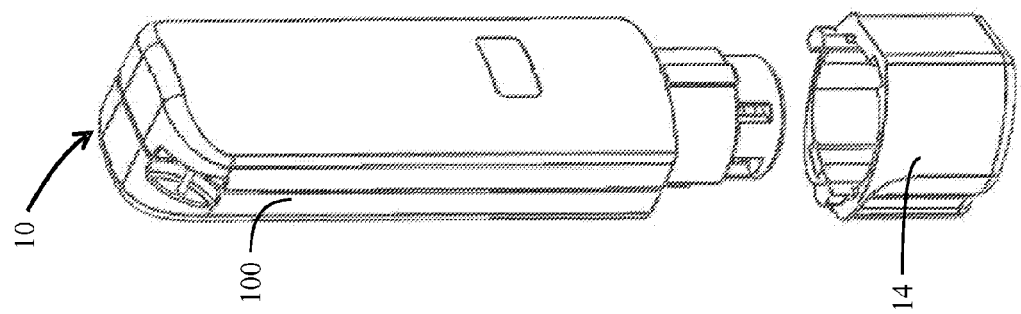
FIGS. 1A-C illustrate perspective exterior views of a medication mixing and delivery device through various actuation steps.
Figure 1B:
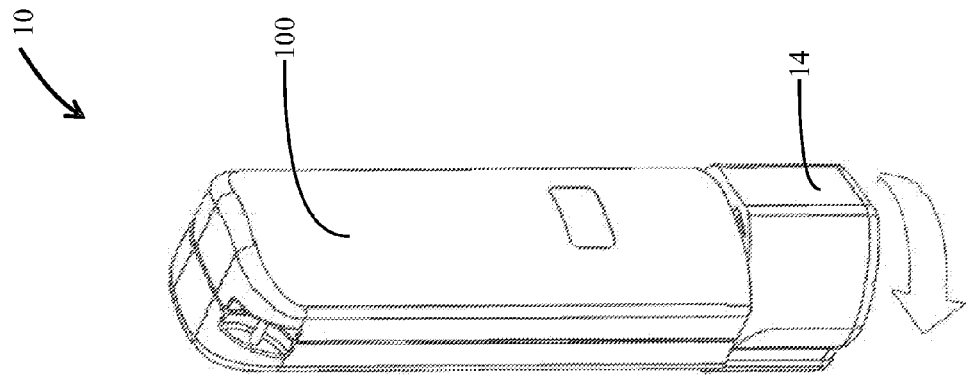
Figure 1A:
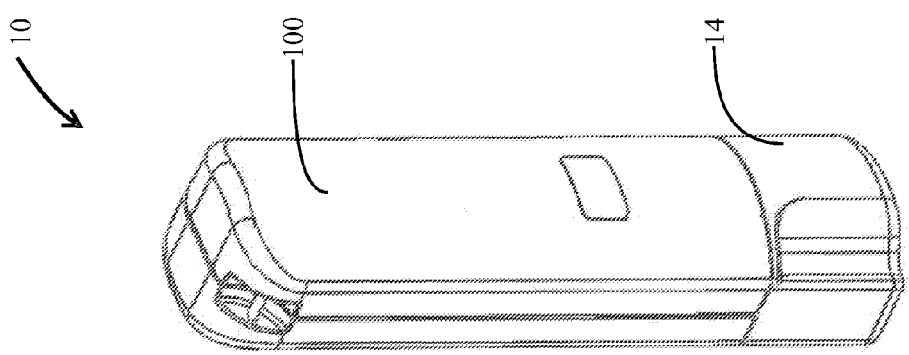

Referring to FIGS. 1A-C illustrate perspective views of an auto-injector which illustrates various aspects of the present invention. This embodiment illustrates an auto-injector 10 which has a housing 100 and a cap 14. The cap 14 can be in mechanical communication with a first actuation mechanism contained within the housing 100. By applying an axial torsional force between the cap 14 and the exterior housing, the actuator can cause certain components contained within the housing to initiate certain steps in the mixing process, for example open a valve between the various chambers, and move fluid contained in one chamber into the chamber containing the dry component of the medicament, which steps will be discussed in more detail below.

In certain embodiments, the cap 14 can be configured such that separation of the cap 14 from the housing 100 can be delayed until the device has moved completely from a stowed state to a completely mixed state. In this manner it can be ensured that the needle end of the auto-injector 10 is not exposed until the device is completely ready for delivery. Such mechanisms can include a threaded interface between the cap 14 and the housing 100, or the components can be keyed such that separation is not possible until a certain degree of rotation has been achieved, etc. Once the cap is removed, the injection end of the housing can then be exposed and a second actuation device triggered so as to inject or otherwise deliver the mixed medicament to a delivery or injection site, for example by depressing the housing up against the delivery site.

In other embodiments, the delivery of the mixed medicament to the injection site can be configured in such a way that the second actuation step cannot be activated until the device has moved completely from a stowed state to a completely mixed state. In this manner it can be ensured that the needle end of the auto-injector 10, while exposed after removal of cap 14, cannot be activated until the device is ready. Such embodiments are enabled by features internal to the device, which will be described below. Once mixing is complete, a second actuation device can be triggered so as to inject or otherwise deliver the mixed medicament to a delivery or injection site, for example by depressing the housing up against the delivery site.

FIGS. 2A-B illustrate an exploded view of an auto-injector 10 in accordance with one embodiment of the present invention. This exploded view illustrates the various internal components within the housing 100 and the cap 14. The housing can include a pre-loaded energy source 122 which is shown here as a spring, or which can be embodied as a compressed air chamber, which is not shown but could be adapted by those having skill in the art. The spring can be configured to provide a driving force and counter force between an inner plunger shaft 212, and transferred to various components of a mixing assembly 200 through various stages, as will be discussed below. The mixing assembly 200 can be contained within a frame 110 wherein individual components of the mixing assembly 200 can be configured to selectively rotate within the housing 100.

The mixing assembly 200 can be retained within the frame using a frame cap 114 which can be formed separately or unitarily with the frame 110. The frame cap 114 prevents the mixing assembly 200 from pushing through the frame 110 and exiting the housing 100 completely upon injection.

A needle shield 150 and needle shield spring 154 can be provide between the frame 110 and the housing 100 at an injection end of the housing 100. The needle shield spring 154 can be configured to bias the needle shield 150 axially downward so as to continuously restrict inappropriate exposure of the needle 310 prior to, during, and after injection.

The frame 110 and portions of the mixing assembly 200 can be configured to rotate together within the housing when an axially torsional force is applied between the cap 14 and the housing 100. The cap 14 can thus be coupled in a radially fixed manner to the frame 110 which is in turn coupled to certain components of the mixing assembly 200, and a driver interface 118 can also be provided which is rigidly coupled to the housing 100 as well as coupled in a radially fixed manner to alternative portions of the mixing assembly 200 such as to the inner plunger shaft 212. In this manner the axially torsional force and counter force applied between the cap and the housing can be transferred into and caused to actuate certain components of the mixing assembly 200.

The mixing assembly can include an inner plunger shaft 212 and an inner plunger 214 which together form a first displacement mechanism. The first displacement mechanism can be configured to reduce the effective volume of the first chamber, which will initially contain the wet solvent or other liquid component of the medicament.

The plunger is configured to interface with an inner vial 210 which forms the first chamber. The inner vial can be housed within a vial sleeve 220, or alternatively the vial sleeve 220 and the inner vial 210 can be formed unitarily of a single material.

The vial sleeve 220 can then interface with a rotational valve seal 230 which sits within an intermediate support 240. The intermediate support 240 can have a second displacement mechanism 250, i.e. a second plunger, which is coupled thereto, the second plunger being configured to reduce the effective volume of a second chamber located within a second vial 270.

The second vial 270 can then be provided with a delivery assembly 300 affixed thereto which can include a needle 310 or cannula as well as a needle guard 314 or other barrier configured to maintain sterility of the delivery assembly prior to use.

FIGS. 3A-D and 4A-D illustrate cross sectional views of the auto-injector 10 and the mixing assembly 200 through various stages of mixing and delivery from a stowed state to a delivered state.

FIGS. 3A and 4A specifically illustrate a stowed configuration of the auto-injector 10 and the mixing assembly 200 contained therein. In this state the inner plunger shaft 212 is configured to rest on an upper edge of the inner frame 110 wherein the upper edge of the frame 110 is configured to prevent the pre-loaded energy source from releasing the energy stored therein and causing the plunger shaft 212 to depress and force the inner plunger 214 to move downward and reduce the effective volume of the interior of the inner vial, i.e. first chamber. luid communication between the first chamber and the second chamber, which is contained within the second vial 270, has not yet been established because an outlet of the inner or first vial (not shown here) is not aligned with the fluidic channel 254.

Dry medication can be kept in a recess 258 formed about an inlet of the second chamber within the second vial 270, such that fluid passing through the fluidic channel passes through or at least in close proximity to the dry medicament stored therein. It will be appreciated that the dry medication can also be stored in the fluidic channel connecting the first and second chambers, or merely kept in any portion of the second chamber wherein a specific recess is not provided.

In this stowed state the second chamber has its effective volume initially reduced to near zero by the second displacement device or plunger 250 so as to further decrease the space occupied by the auto-injector device 10, which decreased space occupation aides in allowing the device to be incrementally smaller, and thus easier to carry.

In this state the needle 310 and assembly, or other deliver mechanism, is retracted so as to prevent premature injection. The needle 310 is also still within the needle guard 314 so as to preserve sterility until the auto-injector is ready for injection.

It will be appreciated that the cap is not shown in these views for purposes of simplicity, however, the cap can, and will usually be, on for the stowed state.

FIGS. 3B and 4B illustrate a second intermediate state wherein the rotary valve is open and fluid communication is established between the first and second chambers just prior to depressing the plunger shaft 212 and the plunger 214. In this state a rotational force has been applied between the outer housing 100 which retains the driver interface 118 plunger shaft 212, vial sleeve 220, inner vial 210 and the valve seal 230 stationary with respect to the housing, then the counter force which is applied to the cap 14 can then be applied so as to twist the frame 110, and the intermediate support 240 which carries the fluidic channel. This opposing respective rotation between the plunger shaft 212, inner vial 210, and the rotational valve seal 230 causes two things to occur simultaneously: First, an outlet of the inner vial is caused to align with an inlet to the fluidic channel thus establishing fluidic communication between the inner vial 210 and the second chamber 270; second, a set of protrusions of the plunger shaft are brought into an axially aligned channel provided in the frame 110 which allows the plunger shaft to be partially driven downward and cause displacement of the fluid contained in the inner vial through the fluidic channel and into the second vial or chamber 270.

In this embodiment, the respective rotation causes the outlet 224 of the first chamber or inner vial 210 which outlet is formed in the rotational valve seal 230 rotate about a central axis until it is aligned with the inlet fluidic channel 254. In some embodiments the rotational valve seal 230 can be configured to form the bottom wall of the inner vial 210, or the inner vial 210 and rotational valve seal 230 can be formed separately and distinctly.

As seen in FIG. 2, the rotational valve seal 230 of this embodiment is keyed having protrusions and channels or apertures corresponding to protrusions and apertures in the vial sleeve such that it remains stationary with respect to the vial sleeve and does not rotate as the cap and intermediate support 240 are rotated so as to allow selective alignment and misalignment between the outlet 224 and the fluidic channel 254. Alternatively, in embodiments being devoid a specific fluidic channel, alignment between the outlet 224 and an inlet of the second chamber so as to selectively allow or prohibit fluid communication therebetween.

In this state the second chamber still has its effective volume near zero by the second displacement device or plunger 250. Additionally, in this state the needle 310 or other deliver mechanism and assembly is still retracted so as to prevent premature injection as mixing has not yet occurred. The needle 310 is also still within the needle guard 314 so as to preserve sterility until the auto-injector is ready for injection and the needle shield 150 is still extended to prevent premature injection.

FIGS. 3C and 4C illustrate a mixed state wherein the intermediate support 240 and frame 110 have been rotated with respect to the mixing assembly 200 such that plunger protrusions 216 of the plunger shaft 212 have been aligned with an axially aligned channel of the of the vial sleeve 220 as well as through a channel in a sidewall of the intermediate support 240.

The axial alignment between the plunger shaft protrusions allows axial translation of the plunger shaft 212 into the inner vial 210. Once this alignment has been achieved, the plunger shaft 212 is allowed to translate axially downward thus depressing the inner plunger 214 into the inner vial 210 which acts to displace the fluid contained therein through the outlet 224 through the fluidic channel 254 and into the second chamber contained within the second vial 270. The second vial 270 is permitted to expand its effective volume by being free to translate downward slightly within the frame and housing. As the second chamber expands to receive the fluid being displaced from the first chamber, the fluid passes through or into the recess 258, which contains the dry medicament, the fluid dissolves the dry component and mixes with the fluid as it enters the second chamber. In another embodiment, the fluid passes into the second chamber 270, without a recess 258, and with the powder being located elsewhere in the second chamber 270. The expanding volume of the second chamber still allows for sufficient mixing with the dry medicament to achieve appropriate mixing.

In the embodiment shown the intermediate support 240 includes similar protrusions resting on an intermediate stop of the frame, and the plunger protrusions of the plunger shaft come to rest on the bottom of the intermediate support channel which indicates full depression of the first plunger into the inner vial, which also signifies that mixing is complete and that the device is ready for the injection step.

In this state the needle 310 or other deliver mechanism and assembly is still retracted so as to prevent premature injection as mixing has not yet occurred. The needle 310 is also still within the needle guard 314 so as to preserve sterility until the auto-injector is ready for injection and the needle shield 150 is still extended to prevent premature injection. However, the needle shield 150, which forms part of a second trigger, is ready to be depressed and thus trigger injection. The functionality of the needle shield 150 will be discussed in greater detail below.

FIGS. 3D and 4D illustrate an injected state wherein the mixing assembly 200 has been rotated another small increment within the housing 100 of the auto-injector 10 such that that protrusions of the plunger shaft 212 as well as additional protrusions, lower intermediate support protrusions 244 as seen in FIGS. 8A-E which will be discussed in more detail below, which are provided on the intermediate support 240 have been rotated around sufficiently so as to align with a second axially aligned channel, 138 as seen in FIGS. 7B-D, of the frame 110.

Once this alignment has been achieved, a second portion of energy stored within the pre-stored energy source which causes the entire mixing assembly to be pushed downward such that the needle guard 314 comes into contact with the frame cap 114 to stop the needle guard 314 such that the needle 310 punctures needle guard 314 and is extended through the needle guard 314. The needle 310 then extends further past the needle shield 150, and the needle 310 is thus extended into or about a delivery site, further as the second vial or chamber 270 hits the bottom portion of the frame cap 114, the second plunger 250 is depressed into the second vial or chamber 270 reducing its effective volume and causes the fluid to be ejected through the delivery assembly and into the patient or onto the delivery site.

FIGS. 5A-E illustrate perspective views of the mixing assembly 200 within the frame 110 which illustrate various stages of actuation through the mixing and injection process.

In particular, FIG. 5A illustrates the relative position of the mixing assembly 200 with respect to the frame 110 in a stowed state. In this state the plunger shaft 212 is provided with a plurality of plunger protrusions 216 which extend radially outward and rest on an upper lip of the intermediate support 240. It will be appreciated that the vial sleeve 220 is also provided with a channel through which the plunger protrusions 216 extend and allow for axial translation in later steps of actuation. In this manner the plunger shaft is maintained in a non-depressed or stowed state wherein rotation of the plunger protrusions 216 into the middle support channel 248 must be effectuated before the plunger shaft 212 can translate axially and depress into the vial (not shown) contained within the vial sleeve 220.

Figure 5C:
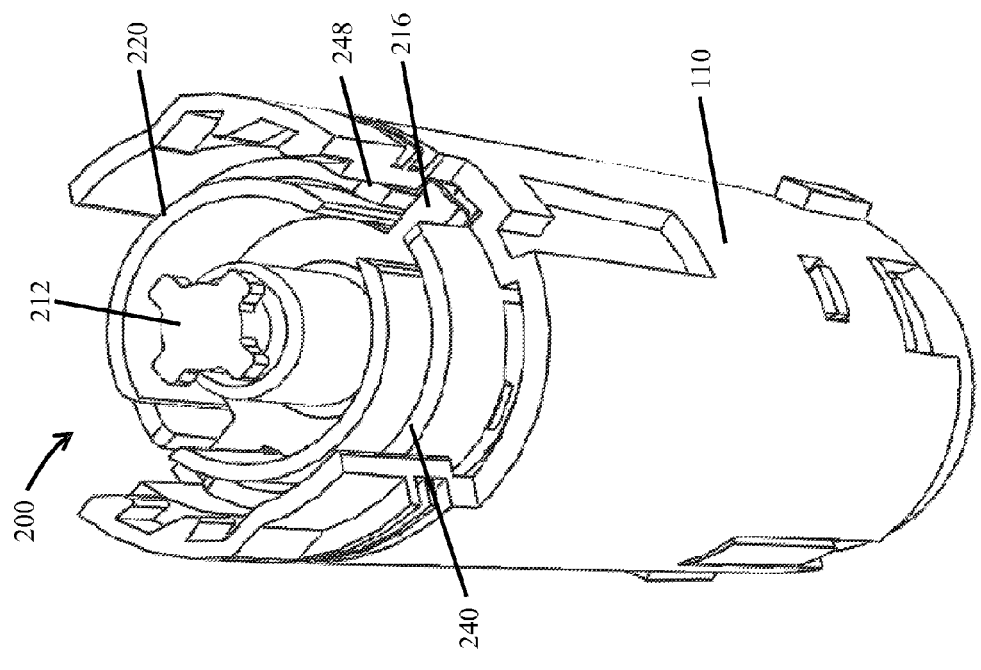
Figure 5D:
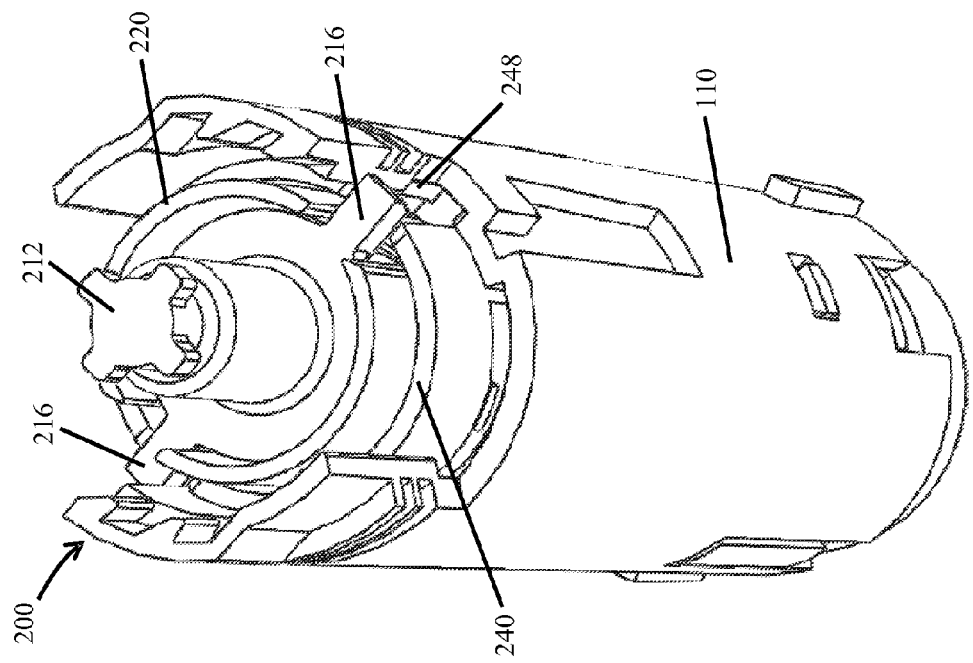

FIGS. 5B-D illustrate the travel of the rotated state of the plunger shaft 212 with respect to the vial sleeve 220 and intermediate support 240. The plunger protrusions 216 are aligned with the channel 248 and are thus ready for release of a portion of energy contained in the pre-loaded energy source to depress the plunger shaft 212 into the vial sleeve 220 and the vial contained therein (not shown) so as to displace the fluid contained therein. In this embodiment, the rotation of the plunger shaft also causes rotation of the vial sleeve 220, which rotation causes the outlet of the first chamber to align with the inlet of the fluidic channel leading to the second chamber. In this manner the alignment and thus opening of the fluidic channel occurs simultaneously with the alignment of the protrusions 216 with the intermediate support channel and allows the pre-loaded energy source to depress the plunger shaft 212.

FIG. 5C illustrates an intermediate partially depressed state and FIG. 5D illustrates a mixed configuration wherein the plunger shaft and plunger have been fully depressed into the first chamber displacing all of the liquid into the second chamber.

Figure 5E:
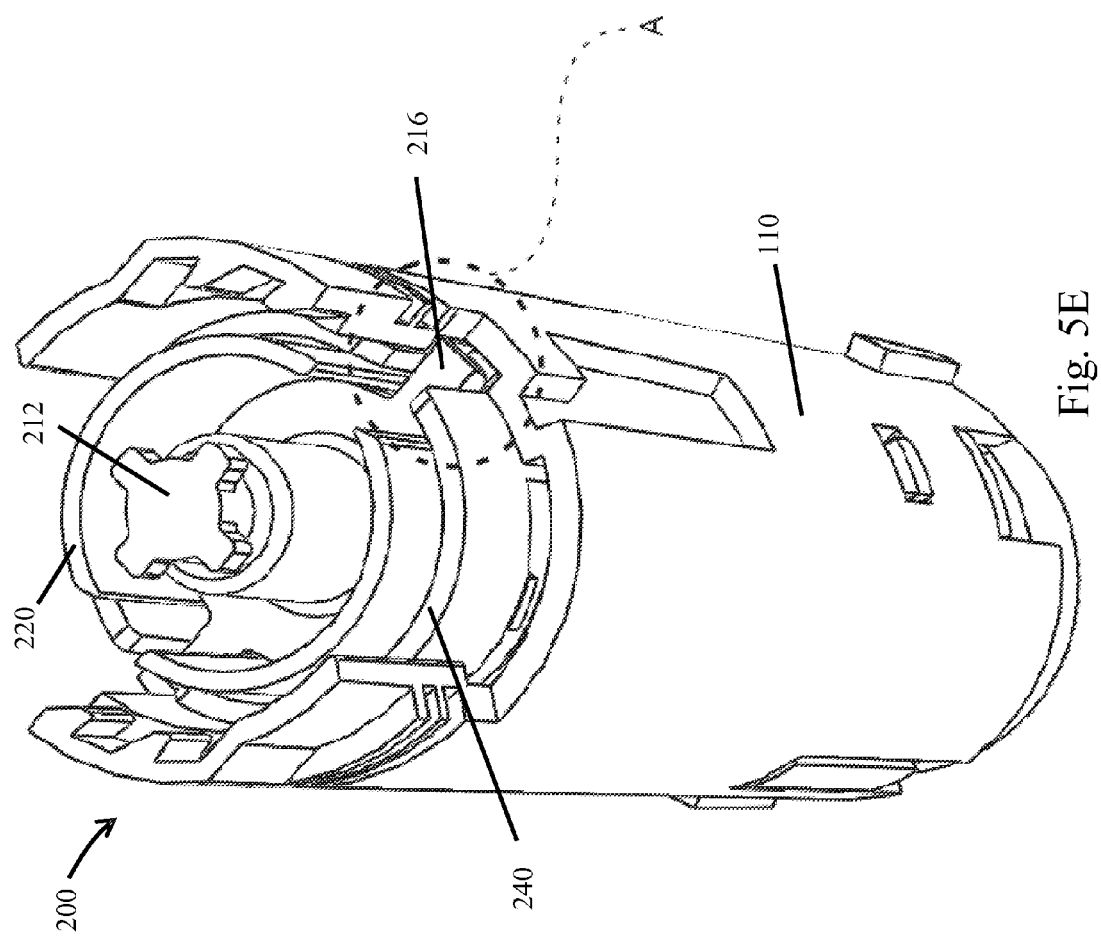

FIG. 5E illustrates a fully mixed state wherein the auto-injector is fully ready for injection. The area A as illustrated in FIG. 5E will be discussed in further detail wherein the mixing assembly 200, which includes the intermediate support 240 together with the vial sleeve 220 and plunger shaft 212 all need to rotate a small distance into the frame 110 so as to initiate the injection step.

FIGS. 6A-E illustrate various perspective detailed and cross sectional views of the area A as defined in FIG. 5E. As discussed above the frame is provided with a plurality of channels. The first frame channel 130 and the intermediate stop 134 have a pair of upper support protrusions 242 of the intermediate support supported therein. After the mixing stage is complete the protrusions 216 of the plunger shaft 212 are resting on the intermediate support 240 on top of the upper support protrusions 242.

In order to translate axially downward to eject the fluid through the delivery assembly the intermediate support 240, vial sleeve 230 and the inner plunger must rotate together so as to be aligned with a second frame channel so as to allow for a second portion of energy to be released from the pre-loaded energy source thus driving the mixing assembly downward, with the delivery assembly affixed to the bottom end thus effectuation injection or delivery. To move from the mixed state and begin injection the upper support protrusions 242 along with the plunger shaft protrusions 216 are rotated radially into a second frame channel 138 as seen best between the positions illustrated in FIG. 6D to FIG. 6E.

In particular, FIGS. 6A-B illustrate perspective exterior and cross sectional views of the interface shown by area A of FIG. 5E wherein the auto injector and mixing assembly is in a mixed state with the plunger protrusions 216 being depressed against the intermediate support 240 and associated upper support protrusions 242. All of which rests on the intermediate stop 134 within the first frame channel 130.

Figure 6D:
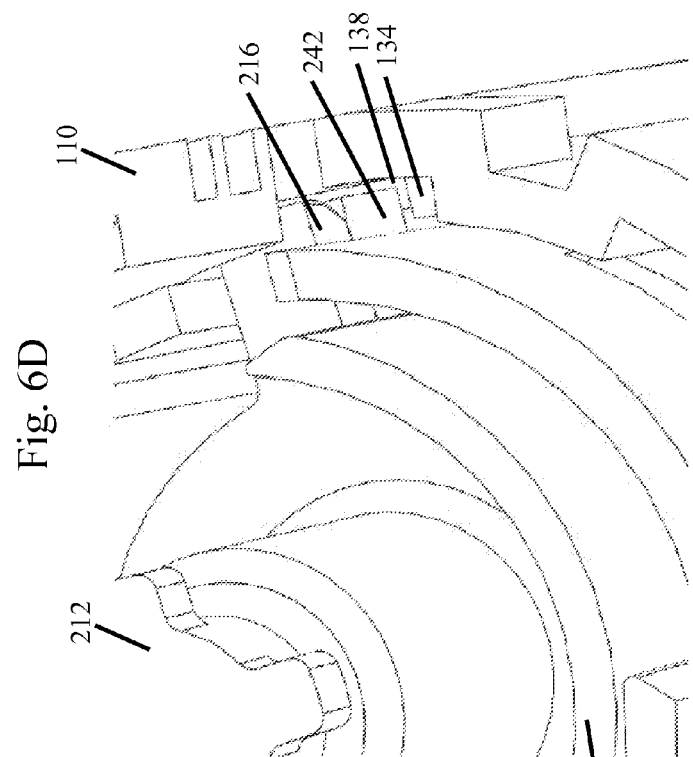
Figure 6C:
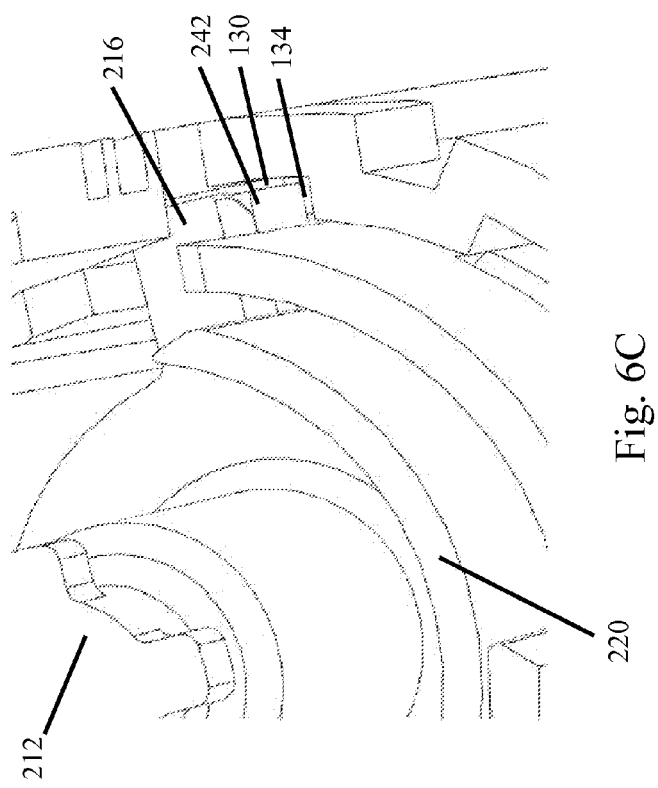

FIGS. 6C-D illustrate perspective exterior views of the interface shown by area A of FIG. 5E wherein the auto injector and mixing assembly is in a mixed state but more importantly illustrating an intermediate rotation of the plunger and upper support protrusions 216 and 242 respectively with respect to the frame 110 into an aligned configuration with the second frame channel 138 just prior to injection.

Figure 6E:
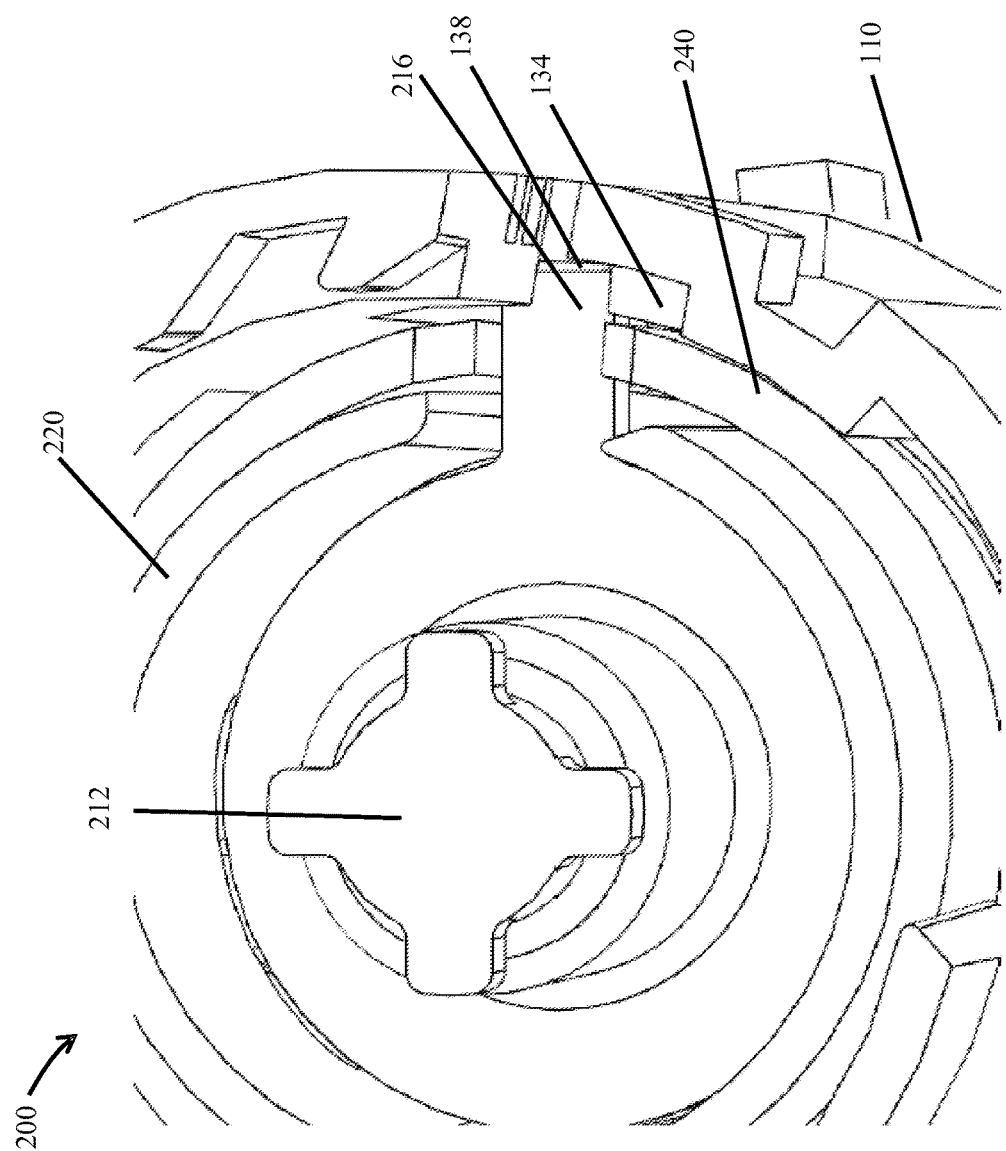

FIG. 6E illustrates the mixing assembly 200 as it is being further depressed into the frame 110 wherein the plunger shaft 212 and protrusions 216 along with the intermediate support 240 are depressed downward thus driving the delivery assembly (not shown) downward to inject the needle, until the second vial engages the lower end of the frame, stops, and the intermediate support (not shown) then drives the second plunger (not shown) into the second vial displacing the mixed drug out of the delivery assembly and into the delivery site. It is this reason, as described above, that the second actuation, which results in the translation of the mixing assembly downward, can not occur until mixing is complete. The plunger protrusions 216 can not rotate with the upper support protrusions 242 until they are able to rotate together, clear the frame and access the second frame channel 138. If the user attempts to actuate the second actuation mechanism prior to plunger protrusions 216 coming into contact with upper support protrusions 242, the mixing assembly will get stopped from entering the second frame channel 138 by the frame 110. This mechanism is helpful in preventing the second actuation step from occurring until all of the fluid from the first chamber has been transferred into the second chamber.

FIGS. 7A-D illustrate various perspective exterior and cross sectional views of the frame 110. These views illustrate the interior fist frame channel 130 and second frame channel 138 with more clarity. These views also illustrate the intermediate stop 134 upon which the upper support protrusions of the intermediate support rests (not shown). In some embodiments the second frame channel 138 can have a tapered channel when effectively increases the width of the second frame channel 138 as the various protrusions travel downward within the second frame channel 138. This tapering ensures that the various protrusions do not bind up during the injections step, and allow the protrusions to travel freely downward until the second vial hits the stops, signaling full needle extension and driving of the second plunger into the vial thus fully ejecting the mixed fluid and medication compound.

FIGS. 7A-D also illustrate a safety mechanism in the form of cap rotation locks 112 which interface with an upper portion of the plunger shaft as well as the driver interface such that once the cap is rotated a certain degree, a corresponding protrusion enters into and meshes with the teeth of the cap rotation lock 112 of the frame and prevents the cap from being twisted back. In this manner, if the cap is inadvertently twisted, and a risk of premature mixing is presented by such rotation, a user cannot simply twist the cap back and place the auto-injector back into storage believing that no mixing has occurred. It will be appreciated that, once mixed, even partially, the dry drug will typically begin to degrade at an increased rate. The purpose of the lock is to prevent accidental mixing, or at least signal to the user that the drugs inside might have been previously mixed, wherein instructions on whether or not to use in the case of premature mixing can be provided.

FIGS. 8A-E illustrate how the needle shield 150 can be configured in one embodiment to act as a bump switch and trigger the injection step by providing the slight rotation of the protrusions 216 and 242 off of the intermediate stop (not shown here) and into the second frame channel discussed above, (not shown). It will be appreciated that this view of the mixing assembly 200 and needle shield 150 are shown herein without the frame so as to better illustrate the interaction of the needle shield 150 with the mixing assembly 200. However, it will be appreciated that the slight rotation shown here provides the rotation as illustrated in FIGS. 6C-E.

In the embodiment shown in FIGS. 8A-E an upward force is applied to the needle shield 150 by depressing the injection end of the auto-injector against the delivery site. In response to this depression force, the needle shield 150 translates upward within the housing and frame such that a lower support protrusion 244 is released from a needle shield hook 158. The needle shield hook prevents premature rotation of the intermediate support off of the intermediate stop during the changing of states from the stowed state to the mixed state by rotation of the vial sleeve and inner plunger as discussed above, preventing the intermediate support from rotating with those components during mixing and thus preventing premature injection. Additionally, the shield hook can be configured so as to transfer the axially rotational force to be applied to the cap, through the frame, and into the intermediate support, which allows for relative rotation between the rotational valve seal, as discussed above, and the fluidic channel disposed within the intermediate support so as to allow initial opening of the rotary valve.

As the needle shield 150 translates upward, the lower support protrusions 244 of the intermediate support interface with a needle shield cam ramp 162. As the needle shield 150 continues to travel upward relative to the intermediate support, the lower support protrusions 244 slide on the needle shield cam ramps 162 and a rotation of the entire mixing assembly 200 is induced as shown in FIG. 8C. In this embodiment the width of the needle shield cam ramps 162 corresponds with a radial distance required to move the upper support protrusions 242 and the plunger protrusions 216 off of the intermediate stop and into the second frame channel which corresponds to the released configuration as illustrated in FIG. 8D. Whereupon, as shown by FIG. 8E the entire mixing assembly 200 can travel downward by force applied from the pre-stored energy source and result in injection or other delivery.

FIGS. 9A-B illustrate an extension and locking function of the needle shield 150. It will be understood that it is of general interest to reduce the potential for inadvertent contamination or sticks of other people prior to injection, during injection, and after injection. As such the needle shield 150 of the present embodiment serves both as a bump switch as well as a protective barrier between the user, and other people from inadvertent sticks, jabs, or cuts from an exposed needle. As such, after the bump switch is activated, the needle shield hook, as discussed above, is released and a needle shield spring 154, as shown in FIG. 2, or other biasing mechanism, is released so as to push the needle shield outward, or axially downward after activation. The delivery assembly and needle are not ejected until the bump switch is first activated, then after injection, as the user pulls the auto-injector away from the delivery site, the needle shield is simultaneously extended until it clears past the tip of the needle, essentially eliminating the risk of secondary pricks and cross contamination of bodily fluids to other people post injection.

In the embodiment shown the frame cap 114 can be provided with a plurality of protrusions, both lock protrusions 116 for interfacing with one or more needle shield guide channels 166 and needle shield extension lock tabs 170 which interface with the interior of the frame or housing. The guide channels can have space for allowing initial depression whereupon the extension lock protrusions can slide up and then interferingly engage with the lock tabs in a fully extended state after injection. The tabs can prevent pulling the needle shield 150 completely free from the housing as well as prevent a secondary depression of the needle shield 150 which would expose the extended needle.

With reference to FIGS. 10-20, shown is an alternative exemplary embodiment of an auto-injector 400 in accordance with a second embodiment. The auto-injector 20 illustrates additional aspects of the present invention, each of which will be discussed in more detail below.

Referring to FIGS. 10A-C illustrate perspective views of an auto-injector 400 which illustrates various aspects of the present invention. This embodiment illustrates an auto-injector 400 which has an exterior housing 402 and a cap 414. The cap 414 can be in mechanical communication with a first actuation mechanism contained within the exterior housing 402. Similar to the embodiment discussed previously, by applying an axial torsional force between the cap 414 and the exterior housing 402, the actuator can cause certain components contained within the housing to initiate certain steps in the mixing process, for example open a valve between the various chambers, and move fluid contained in one chamber into the chamber containing the dry component of the medicament, which steps will be discussed in more detail below. The relative motion of the various components can be provided through the use of various protrusions which engage with or otherwise interact with cams or channels within the housing.

In certain embodiments, the cap 414 can be configured such that separation of the cap 14 from the housing 402 can be delayed until the device has moved completely from a stowed state to a completely mixed state. In other embodiments the cap can act merely as a contaminant barrier and actuation is effectuated after removing the cap. The embodiment shown illustrates the first, wherein removal of the cap effectuates initiation of, and completion of, the mixing step. In this manner it can be ensured that the needle end of the auto-injector 400 is not exposed until the device is completely ready for delivery.

Figure 11C:
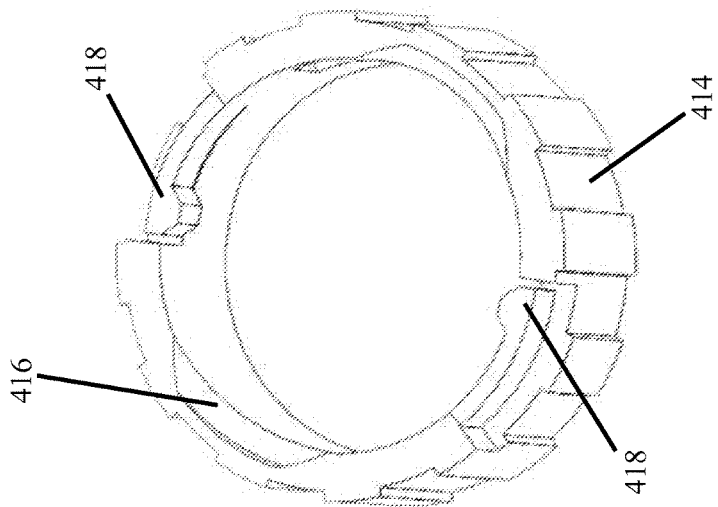
FIGS. 11A-C illustrate various perspective and cross sectional views of a cap for use in the medication mixing and delivery device of FIGS. 10A-D.
Figure 11B:
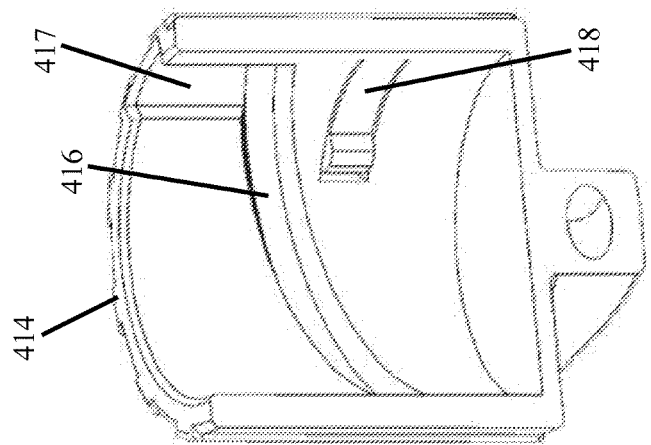
Figure 11A:
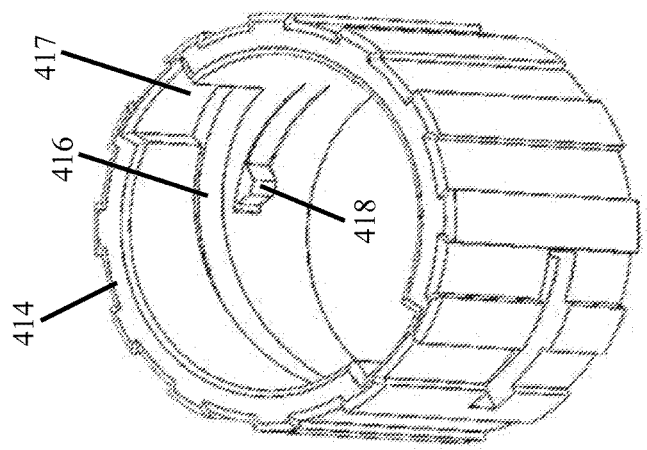
Figure 13D:
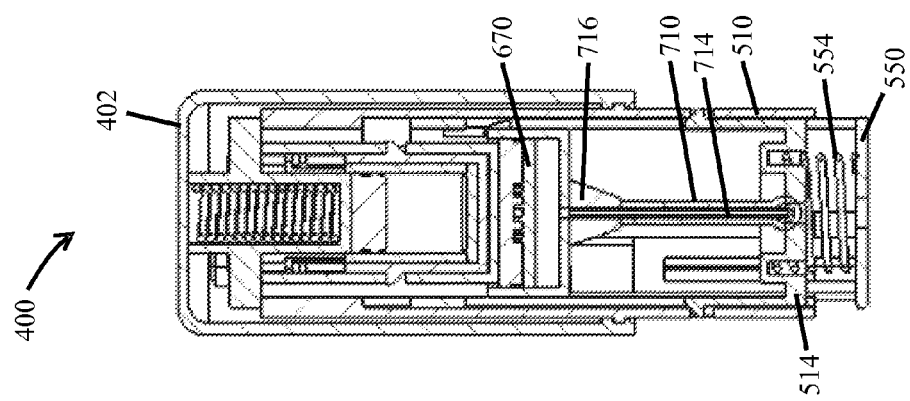
FIGS. 13A-D illustrate various exterior perspective, side, and cross sectional views of the medication mixing and delivery device as illustrated in FIGS. 10A-D in a stowed state.
Figure 13C:
Figure 13B:
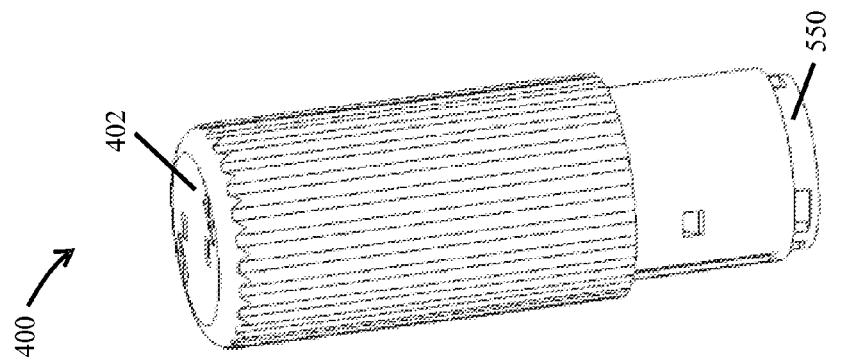
Figure 13A:
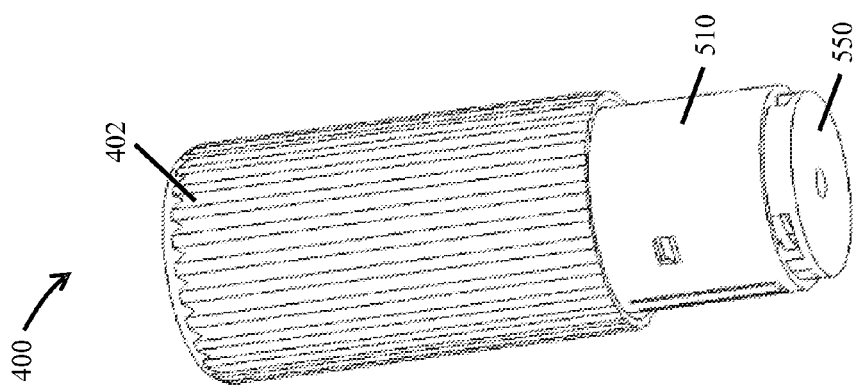
Figure 18D:
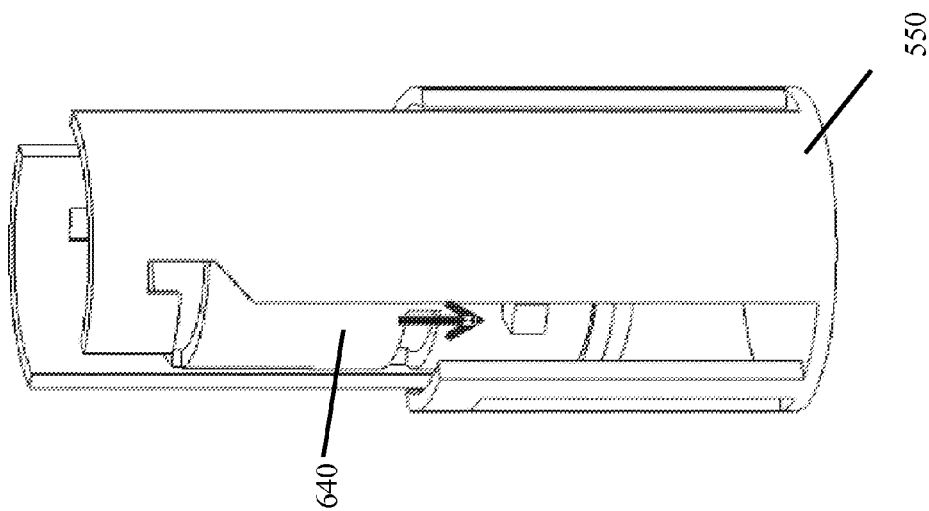
Figure 18C:
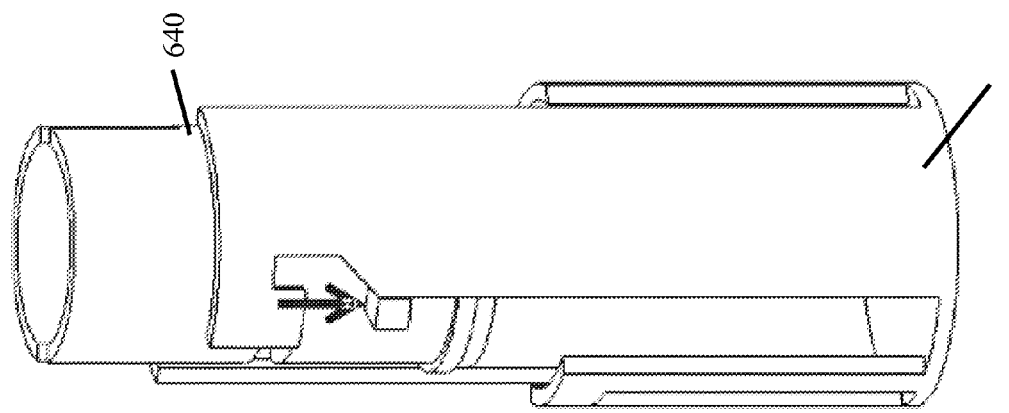

With regard to the cap 414 and in reference to FIGS. 11A-C, the Cap 414 can include cam protrusions on an internal portion of the housing or frame which interact with associated cam ramps 416, wherein the cam ramps 416 allow for release through the keyway 417 after a certain degree of rotation has been achieved. In alternative embodiments, threaded interfaces can be provided between the cap 414 and the housing 400 wherein the axial relative translation of the cap and the housing can effectuate an initiation of the mixing step is also contemplated. However, in each of these embodiments once the cap is removed, the injection end of the housing can then be exposed and a second actuation device triggered so as to inject or otherwise deliver the mixed medicament to a delivery or injection site, for example by depressing the housing up against the delivery site, which acts as a bump switch which in turn initiates injection.

The cap 414 can also include a pair of retaining clips 418 which can interface with a pair of indents on the frame of housing so as to prevent premature rotation of the cap and associated activation of the auto injector.

FIGS. 12A-E illustrate various exploded views of various internal assemblies within the auto-injector 400 in accordance with one embodiment of the present invention. These exploded views illustrate the various internal components within the housing 402 and the cap 14. The housing 402 can include a pre-loaded energy source 522 which is shown here as a spring, or which can be embodied as a compressed air chamber, which is not shown but could be adapted by those having skill in the art. The spring can be configured to provide a driving force and counter force between an inner plunger shaft 612, the driving force being transferred to various components of a mixing assembly 600 through various stages, as will be discussed below. The mixing assembly 600 can be contained within a frame 510 which is can be configured to rotate within the housing 402.

A needle shield 550 and needle shield spring 554 can be provide between the frame 510 and the housing 402 at an injection end of the housing. The needle shield spring 554 can be configured to bias the needle shield axially downward so as to continuously restrict open and inappropriate exposure of the needle prior to, during, and after injection.

The frame 510 and portions of the mixing assembly 600 can be configured to rotate together within the housing when an axially torsional force is applied between the cap 414 and the housing 402. The cap 414 can thus be coupled in a radially fixed manner to the frame 510 which is in turn coupled to certain components of the mixing assembly 600. In this manner the axially torsional force applied between the cap 414 and the housing 510 can be transferred into and caused to actuate certain components of the mixing assembly 600 using actuation means which will be discussed in more detail below.

The mixing assembly 600 can include an inner plunger shaft 612 and an inner plunger 614 which together form a first displacement mechanism which can be configured to reduce the effective volume of the first chamber, which will initially contain the wet solvent or component of the end injectable medicament.

The plunger 614 is configured to interface with an inner vial 610 which forms the first chamber. The inner vial can be housed within a vial sleeve 620, or alternatively, the vial sleeve 620 and the inner vial 610 can be formed unitarily of a single material.

The intermediate support 640 can have a second displacement mechanism 650, i.e. a second plunger, which is coupled thereto, the second plunger being configured to reduce the effective volume of a second chamber located within a second vial 670.

The second vial 670 can have a delivery assembly 700 affixed thereto which can include a needle 710 or cannula as well as a needle guard 714 or other barrier configured to maintain sterility of the delivery assembly prior to use. The needle 710 can be affixed to the second vial 670 using a bonding interface 716, which can be provided as a crimp, adhesive, curing epoxy, or any other number of suitable interfaces.

FIGS. 13A-D illustrate various perspective, side and cross sectional views of the auto-injector 400, with the cap removed, wherein the mixing assembly is maintained in a stowed state prior to initiation.

FIGS. 14A-C illustrate various perspective, side and cross sectional views of a various states of assembly of the auto-injector 400, with the cap or housing removed which illustrates actuation of the first mixing step, wherein rotational motion of the upper portion of the mixing assembly is illustrated prior to the valve being open and energy from the pre-loaded energy source is released. In this state the inner plunger shaft 612 is resting on an upper edge of the inner frame 510 wherein the upper edge of the frame 510 is preventing the pre-loaded energy source from releasing the energy stored therein and causing the plunger shaft from depressing and forcing the inner plunger from moving downward and reducing the effective volume of the interior of the inner vial, i.e. first chamber. Fluid communication between the first chamber and the second chamber within the second vial 670 has not yet been established because an outlet (not shown here) is not aligned with the fluidic channel (not shown).

Dry medication can be kept within the fluidic channel between the two chambers, or alternatively the dry medication can be stored within the second chamber within the second vial 470.

In this state the needle 710 or other deliver mechanism and assembly is retracted so as to prevent premature injection. The needle 710 is also still within the needle guard 714 so as to preserve sterility until the auto-injector is ready for injection.

It will be appreciated that the cap is not shown in these views for purposes of simplicity, however, the cap can and will usually be on for the stowed state.

FIGS. 15A-C specifically illustrate a mixing initiated step wherein a fluidic pathway has been established between the first and second chambers just prior to release of energy from the pre-loaded energy source to drive the fluid from the first chamber into the second chamber. In this state the rotary valve is open and fluid communication is established between the first and second chambers just prior to depressing the plunger shaft 612 and the plunger, 614 in FIG. 12C. In this state a rotational force has been applied to the outer housing 402 and the cap 414 wherein the force is applied to twist the plunger 614 and plunger shaft 612 inner vial 610 vial sleeve 620 with respect to the housing 100, the frame 510 and intermediate support 640.

This respective rotation causes an alignment of an outlet of the first chamber 610 with a fluidic channel extending into the second chamber 670.

In this state the needle 710 or other deliver mechanism and assembly is still retracted so as to prevent premature injection as mixing has not yet occurred. The needle 710 is also still within the needle guard 714 so as to preserve sterility until the auto-injector is ready for injection and the needle shield 550 is still extended to prevent premature injection.

FIGS. 16A-C and 17A-B illustrate a mixed state wherein the mixing assembly 600 has been rotated sufficiently within the housing such that protrusions, 616 from FIGS. 14A and 15A, of the plunger shaft 612 have been rotated around sufficiently so as to align with an axially aligned channel of the of the vial sleeve 620 as well as through the intermediate support 640, and has translated axially so as to rest on an intermediate stop of the frame. This axial alignment allows axial translation of the plunger shaft 612 into the inner vial 610, which acts to displace the fluid contained therein through the outlet, through the fluidic channel, and into the second chamber contained within the second vial 670 to mix with the dry medicament in the fluidic path.

In this state the needle 710 or other deliver mechanism and assembly is still retracted so as to prevent premature injection as mixing has not yet occurred. The needle 710 is also still within the needle guard 714 so as to preserve sterility until the auto-injector is ready for injection and the needle shield 550 is still extended to prevent premature injection.

However, the needle shield 550, which forms part of a second trigger, is ready to be depressed and thus trigger injection. The functionality of the needle shield 550 will be discussed in greater detail below.

FIGS. 18A-D illustrate various perspective views of a second actuation mechanism of the medication mixing and delivery device as embodied in FIGS. 10A-D illustrating changing from the mixed state to an injected state. This actuator functions similarly to the embodiment discussed above wherein the intermediate support 640 is provided with a protrusion 644 which is rotated incrementally by depressing the needle shield 550. The incremental rotation of the intermediate support 640 causes the plunger protrusions, not shown here, to rotate with the intermediate support 640 and align with a second channel of the housing or frame, and allow for injection to be initiated.

FIGS. 18A-D illustrate a bump switch which operates similarly in function to the embodiments discussed above, however the protrusions of the intermediate support are located in a slightly different configuration, as seen. In particular, the intermediate support does not have an upper protrusion and instead has channels through which the protrusions of the inner plunger can travel through and interface with the intermediate stop, thus allowing the auto-injector to stop in a mixed but non-injected state.

It will be understood that this embodiment also works using a rotational style valve which utilizes selective alignment of an outlet 624 of the first chamber 610 with the inlet of the fluidic channel, wherein the selective alignment corresponds with an open configuration when aligned and a closed configuration when misaligned.

Figure 19B:
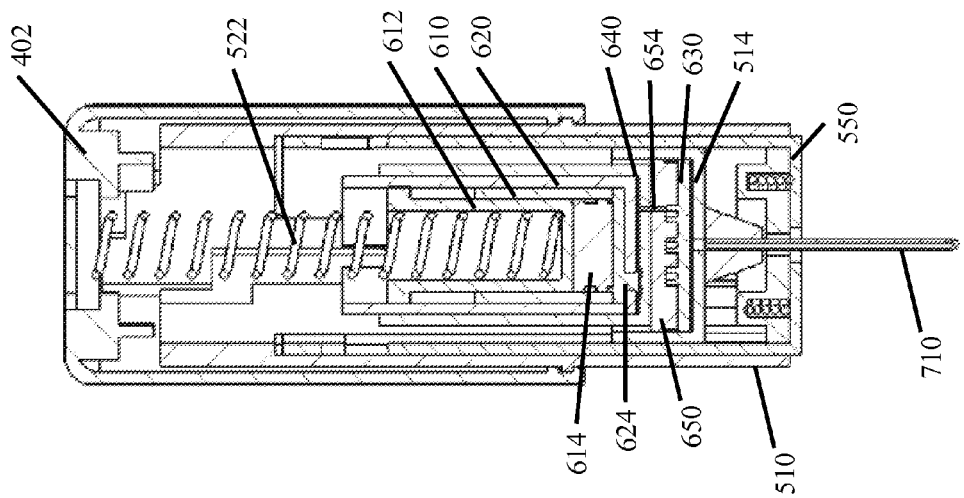
FIGS. 19A-B illustrate side and cross sectional views of the medication mixing and delivery device as embodied in FIGS. 10A-D illustrating an injection complete state.
Figure 19A:
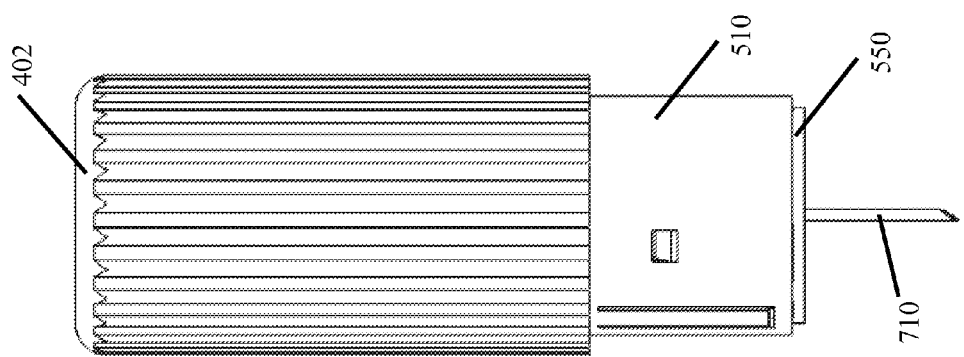

FIGS. 19A-B illustrate an injected state wherein the mixing assembly 600 has been rotated another small increment within the housing 402 of the auto-injector 400 such that that protrusions of the plunger shaft 612 have been rotated around sufficiently so as to align with a second axially aligned channel of the frame 510, the second channel is not shown herein, but is similar in arrangement to the embodiment previously discussed in particular with reference to FIG. 7A-D. Once this alignment has been achieved, a second portion of energy stored within the pre-stored energy source which causes the entire mixing assembly to be pushed downward wherein the second vial 670 hits a bottom portion of the frame 510 and frame cap 414 wherein the needle 710 is extended through the needle guard 714 past the needle shield 550 and extended into or about a delivery site, further as the second vial 670 hits the bottom portion of the frame 510 the second plunger 650 is depressed into the second vial 670 reducing its effective volume and causes the fluid to be ejected through the delivery assembly and into the patient or onto the delivery site.

In this state the needle 710 or other deliver mechanism and assembly are extended such that the needle 710 penetrates the needle guard 714 and is extended past the needle shield 750.

In order to translate axially downward to eject the fluid through the delivery assembly the intermediate support 640, vial sleeve 630 and the inner plunger 612 must rotate together so as to be aligned with a second frame channel so as to allow for a second portion of energy to be released from the pre-loaded energy source thus driving the mixing assembly downward, with the delivery assembly affixed to the bottom end thus effectuation injection or delivery. To move from the mixed state and begin injection, and as discussed above with reference to FIGS. 18A-D, the intermediate support can be provided with one or more protrusions 644, which can be caused to rotate similar to the previously discussed embodiment using cam ramps associated with a bump switch, which the needle shield 550 forms part.

FIGS. 20A-D illustrate an extension and locking function of the needle shield 550. It will be understood that it is of general interest to reduce the potential for inadvertent contamination or sticks of other people prior to injection, during injection, and after injection. As such the needle shield 550 of the present embodiment serves both as a bump switch as well as a protective barrier between the user, and other people from inadvertent sticks, jabs, or cuts from an exposed needle. As such, after the bump switch is activated, the needle shield hooks as discussed above are released and a needle shield spring 554 or other biasing mechanism which is configured to push the needle shield outward, or axially downward. The delivery assembly and needle are not ejected until the bump switch is first activated, then after injection, as the user pulls the auto-injector away from the delivery site, the needle shield is simultaneously extended until the needle clears past the tip of the needle, essentially eliminating the risk of secondary pricks and cross contamination of bodily fluids to other people post injection.

In the embodiment shown the housing 402 can be provided with a plurality of protrusions 516 for interfacing with an upper locking edge 566 of the needle shield. Once the needle shield 550 has been extended a certain degree the protrusions 516 engage with the upper locking edge 566 and prevent subsequent depression of the needle shield. The needle shield hook 558 which previously prevented the premature rotation of the intermediate support can now act as an extension prevention mechanism and can interface with the protrusion 644 of the intermediate support 640 so as to prevent complete removal of the needle shield 550 and thus expose the contaminated needle.

FIGS. 21-24 illustrate various aspects of yet another auto-injector 1010 in accordance with yet another embodiment of the present invention. The auto-injector 1010 can include a housing 1100 which houses a plurality of chambers. The chambers can include a first wet chamber 1210 which can initially contain a wet component for reconstituting, dissolving, and/or suspending a dry medicament. The dry medicament can be contained within a second chamber 1270 or within a fluidic channel 1254 which connects the two chambers, or within a recess formed at an opening or outlet thereof. The orientation of this embodiment includes an intermediate support 1240 which pushes a first plunger 1214 upwards into the first chamber 1210.

It will be appreciated that, with respect to gasses, most fluids are considered incompressible. In order to facilitate upward motion of the first plunger 1214 and the fluid contained within the first chamber 1210, a third plunger 1215 and a squeeze chamber 1004 can be provided wherein a compressible gas is provided within the squeeze chamber 1004 or the gas contained therein is permitted to exit the squeeze chamber 1004. The upward translation of the first plunger 1214 allows it to travel into a portion of the first chamber 1210 which is provided with a fluidic bypass 1255 in the sidewall. In this bypass portion, the fluidic bypass 1255 allows the first chamber 1210 to be compressed and the fluid to travel around the first plunger 1214 through the fluidic bypass 1255 and into and through a fluidic channel 1254 so as to enter into the second chamber 1270 so as to mix with the dry medicament provided within the fluidic channel 1254 or within the second chamber 1270. In the embodiment shown, the plunger 1214 can be provided with a radially disposed slot on its bottom surface so as to allow fluid to travel from the bypass channel 1255 which is located about the perimeter of the chamber, to the inlet of the fluidic channel 1254 which is located about a central portion.

In this embodiment the intermediate support 1240 can support the second plunger 1250 such that the upward translation of the first plunger 1214 also causes the second chamber 1270 to push away from the second plunger 1250 simultaneously as the first chamber 1210 is compressed so as to expand and accordingly receive the fluid as it travels through the bypass 1255, through a channel formed in the bottom of the first plunger 1214, through the fluidic channel 1254, and into the second chamber 1270.

FIGS. 21B, 22A-E, and 23A-D illustrate the various stages of the auto injector 1010 and the mixing assembly 1200 from a stowed through the various mixing stages and finally to an injected state.

Figure 22C:
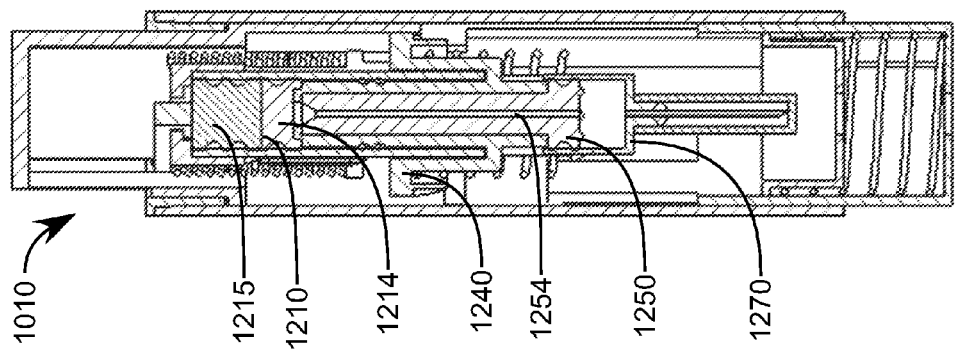
FIGS. 22A-E illustrate various cross sectional views of the medication mixing and delivery device of FIGS. 21A-B through various actuation steps.
Figure 22B:
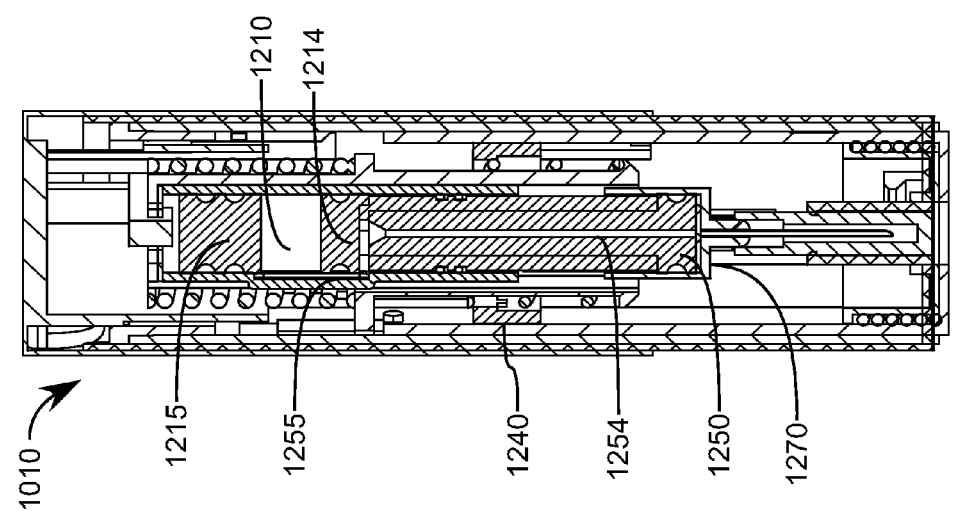
Figure 22A:
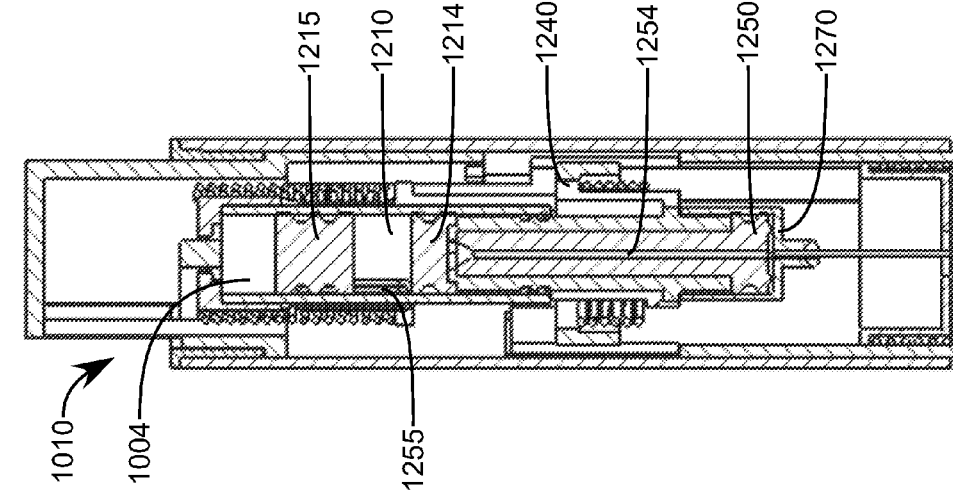
Figures 23A, 23B, 23C, 23D:
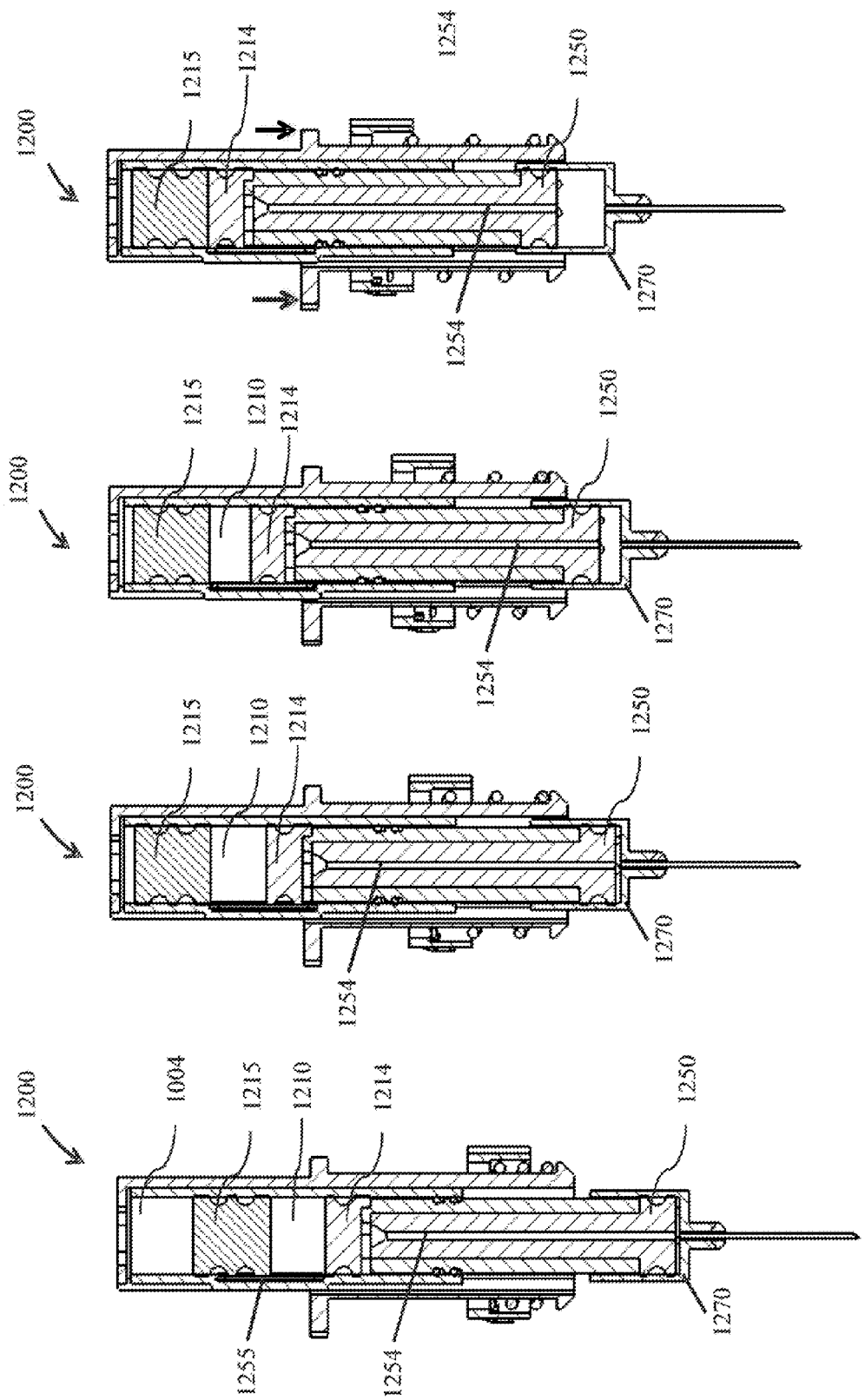
FIGS. 23A-D illustrate various cross sectional detailed views of a mixing assembly for use with the medication mixing and delivery device of FIGS. 21A-B through various actuation steps.

FIG. 22A and FIG. 23A illustrate the auto-injector and mixing subassembly in a stowed state wherein the fluid is in the first chamber 1210, the first plunger 1214, intermediate support 1240 and the third plunger 1215 have not been translated upward.

FIG. 22B and FIG. 23B illustrate the auto-injector and mixing subassembly in an intermediate state wherein the intermediate support 1240 is beginning to move the first plunger 1214 and the third plunger 1215 upward so as to move the first plunger 1214 into the fluidic bypass portion along the length of the bypass fluidic channel 1255 and wherein the third plunger 1215 is beginning to compress the squeeze chamber 1004. This position allows the fluid contained in the first chamber 1210 to bypass around the first plunger 1214 through the bypass channel 1255 and through 1214 into the fluidic channel 1254 and into the second chamber 1270 which expands in effective volume as the intermediate support 1240 moves upwards.

Figure 22E:
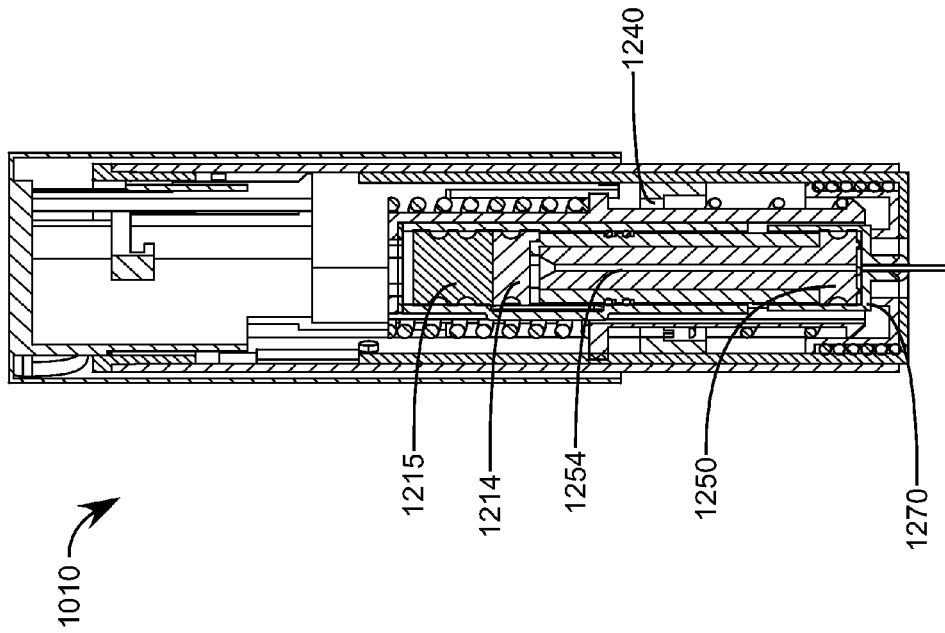
Figure 22D:
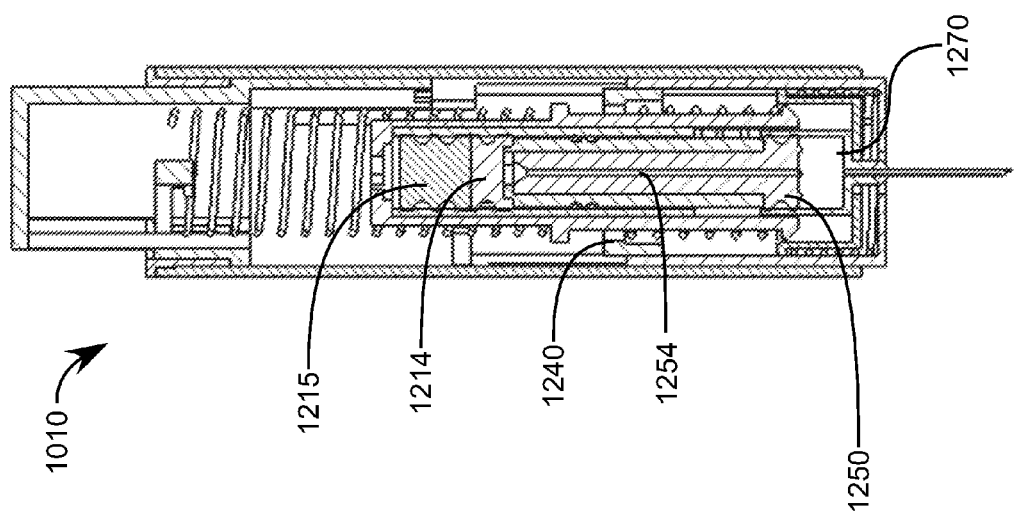

FIGS. 22C-D and FIG. 23C illustrate the auto-injector and mixing subassembly in a mixed state wherein the intermediate support 1240 is fully depressed upwards having moved the first plunger 1214 and the third plunger 1215 completely upward so as to fully displace all of the fluid out of the first chamber 1210. In this position the fluid is completely contained in the second chamber 1270 and ready for injection. In this fully injected state the needle is extended through the housing 1100 and into or about a delivery site.

FIG. 22E illustrates the auto-injector and mixing subassembly in a fully injected state wherein the entire mixing assembly is depressed downward and into the second chamber thus displacing the mixed medication and fluid out through the delivery assembly, i.e. the needle.

FIG. 25A-D illustrates yet another embodiment of an auto-injector 1300 which has a first chamber 1410 containing a fluid component therein and a second chamber 1470 containing a dry medicament component. The auto-injector 1300 can have a movable body 1450 which has a fluidic channel 1454 provided therethrough. In one embodiment the fluidic channel can contain the dry medicament component. In another embodiment the dry medicament component can be placed just upstream from the fluidic channel In order to displace the fluid within the first chamber 1410 into the second chamber 1470.

In one embodiment an initial tensile force can be applied at two ends of the housing so as to be pulled or telescoped axially apart thus causing a first telescoping effect which causes the movable body 1450 to be displace upwards into the first chamber 1410 and force the fluid from the first chamber 1410, through the fluidic channel 1454 and into the second chamber 1470. This motion of the movable body upwards causes the second chamber 1470 to simultaneously expand so as to facilitate in the receipt of the fluid being displaced and thus facilitate mixing of the fluid with a dry medicament stored either within the fluidic channel 1454 or within the second chamber 1470. Once the fluid and the dry medicament are fully mixed the device can be pulled or telescoped axially apart further, which telescoping causes a pin 1314 disposed within the housing 1310 to pull away from a lock mechanism 1304, wherein a trigger device causes protrusions of the locking mechanism to translate radially inward and release through a hole, wherein translation was previously restricted by the pin 1314, wherein the trigger also allows a pre-loaded energy source 1322, i.e. a spring to be released, and push the entire mixing assembly 1350 in an axial direction toward the needle assembly. This trigger device can also be provided as a bump switch or needle guard depression switch similar to those disclosed with reference to the embodiments disclosed above. Once the needle is extended from the housing a bottom portion of the second chamber 1470 will engage the housing 1310 and cause the movable body 1450 to displace the fluid in the second chamber 1470 out through the needle 1490 and into the delivery site.

Figure 24:
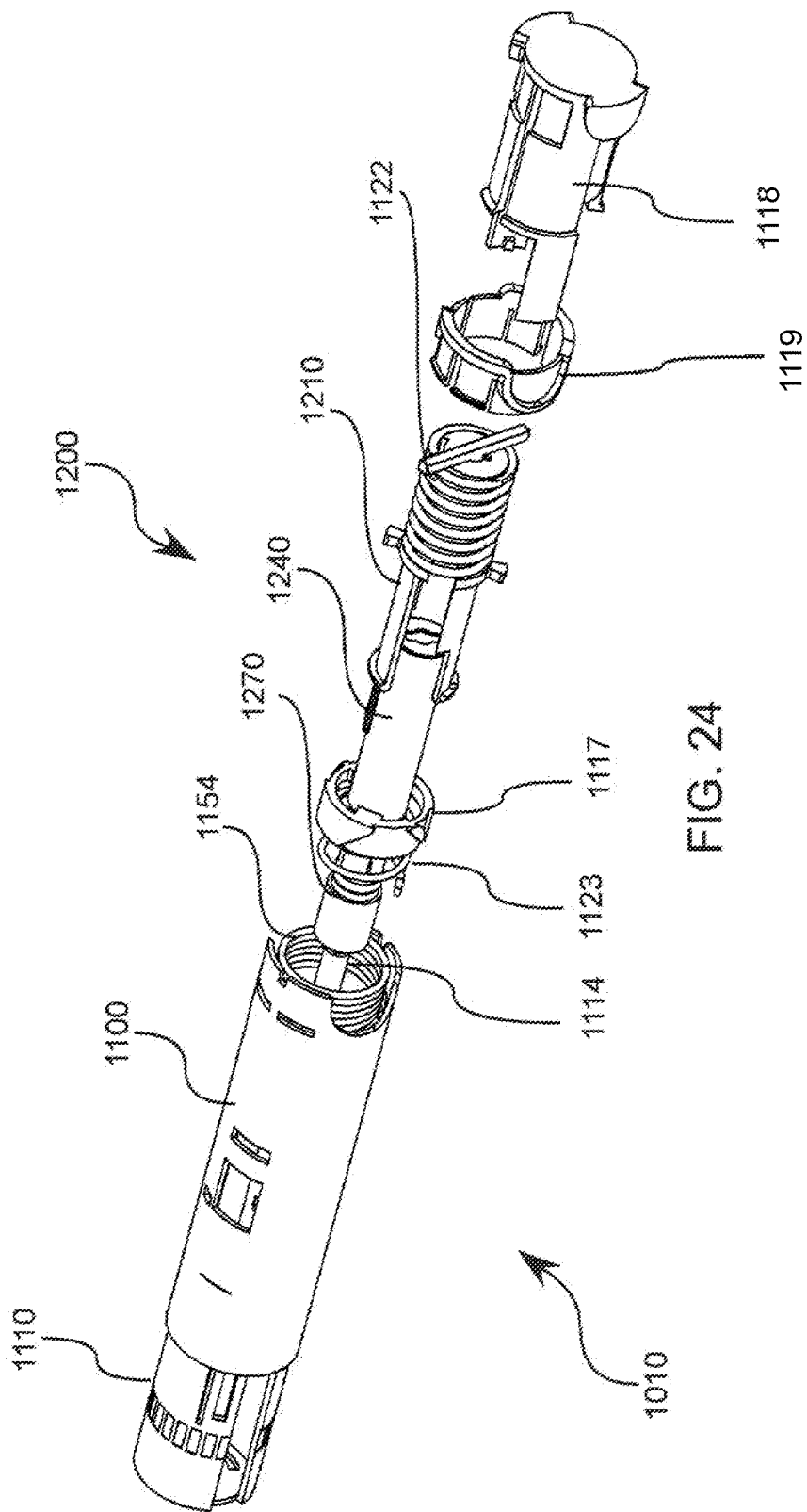
FIG. 24 illustrates a perspective exploded view of a mixing assembly for use with the medication mixing and delivery device of FIGS. 21A-B through various actuation steps.
Figure 25A:
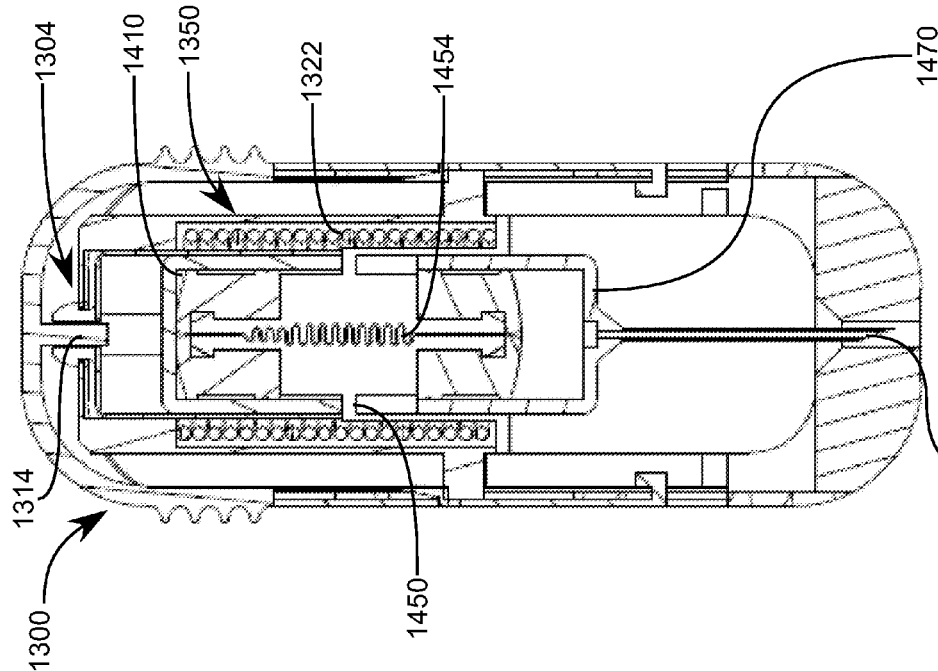
FIGS. 25A-D illustrate various cross sectional views of yet another alternative embodiment of a medication mixing and delivery device in various actuated states.
Figure 25B:
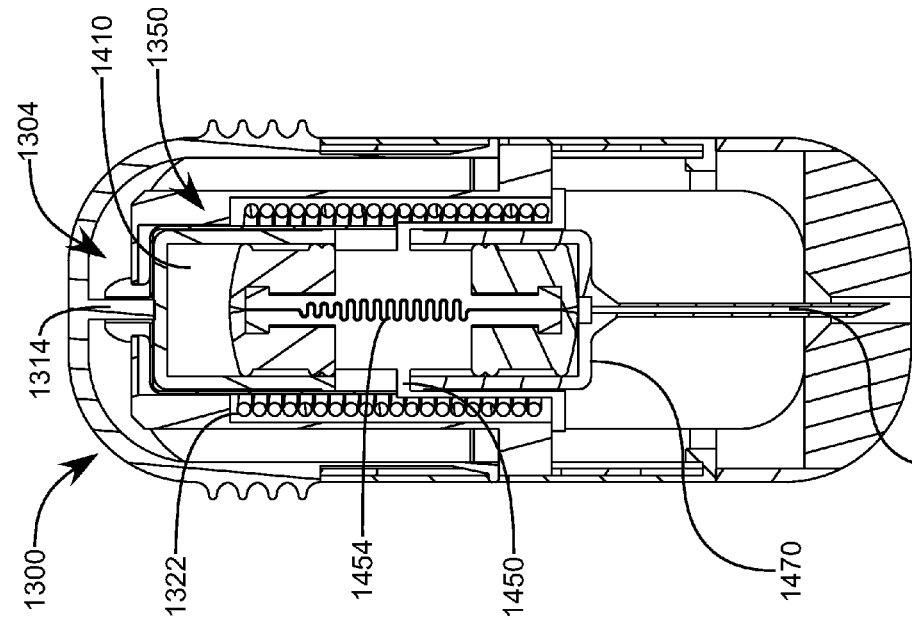
Figure 25C:
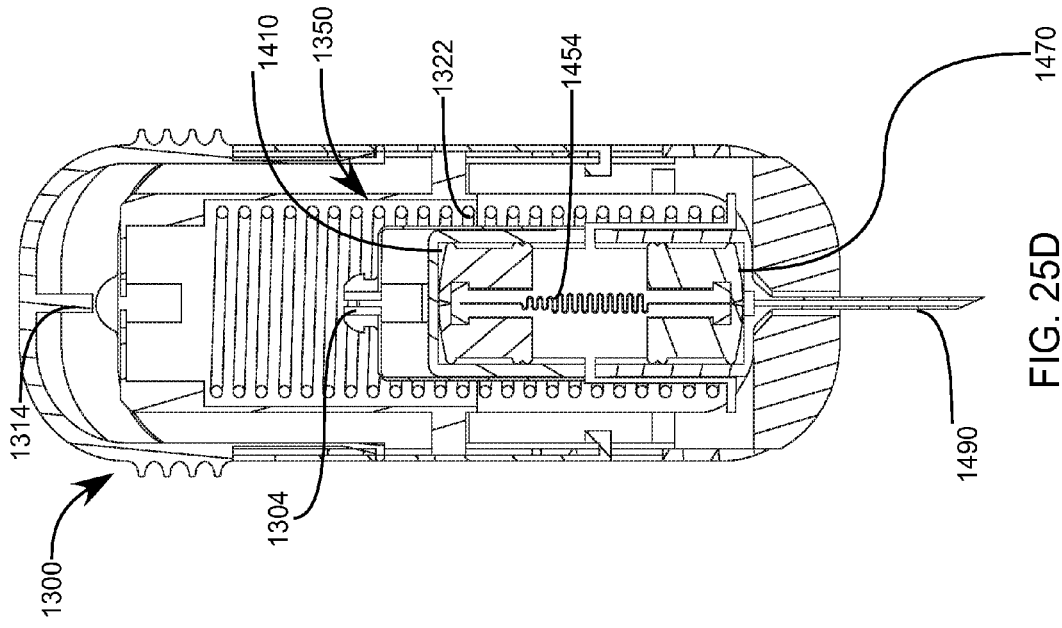
Figure 25D:
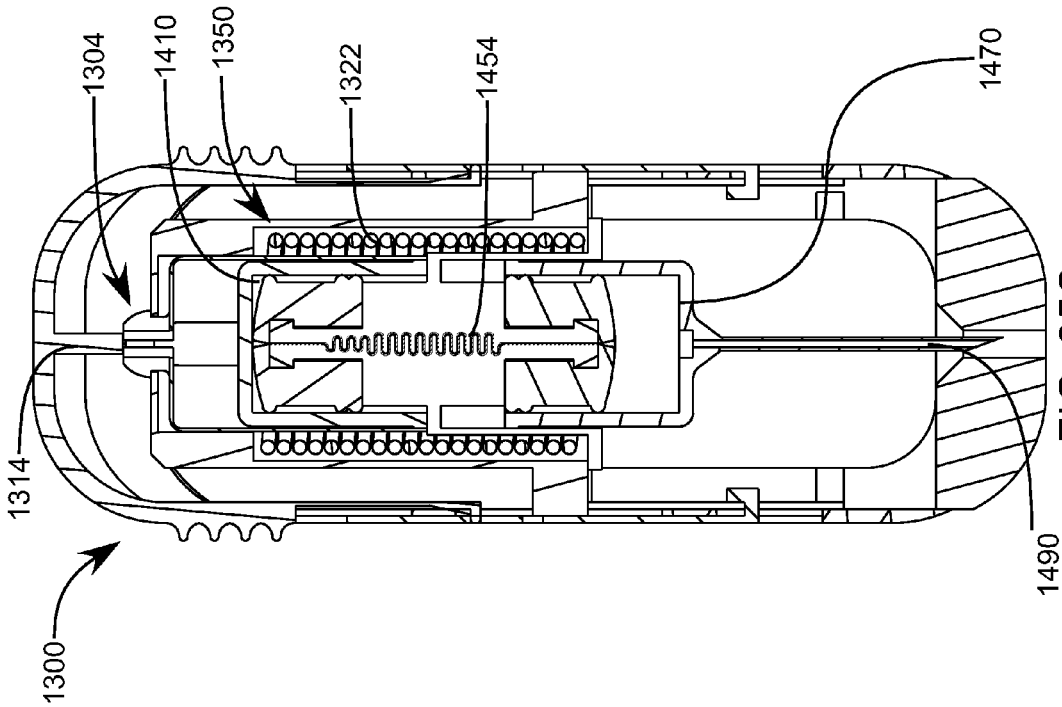

FIG. 24 illustrates a perspective exploded view of the embodiment of the auto-injector 1010 of FIGS. 21-23, which better illustrate the assembly and how many of the individual components interact with one another. A housing 1100 can contain the mixing assembly 1200, wherein the mixing assembly 1200 can be retained within the frame 1100 by the needle guard 1110 on an injection end and by a retention clip 1119 and pull trigger 1118 on an opposing distal end. The mixing assembly 1200 can include up inner vial 1210 and an intermediate support 1240 wherein the extension of the pull trigger 1118 causes the cam ring 1117 to rotate and allow the mixing spring 1123 to discharge a torsional and axial force stored therein so as to rotate the middle stopper 1117. Rotation of the cam ring 1117 is configured to cause the intermediate support 1240 to translate upward into the inner vial 1210, open fluidic communication, and displace the fluid contained therein into the second vial 1270. It will be appreciated that cam ring 1117 and intermediate support 1240 can be separate components for purposes of assembly, or alternatively they can be unitarily formed. Then upon depressing the needle guard 1110 into the housing 1100 the main spring 1122 is discharged and the entire mixing assembly 1200 is forced downward extending a needle (not shown) through the housing. The fluid, which is now contained in vial 1270, is then displaced through the needle contained in sterility barrier 1114. It will be appreciated that sterility barrier 1114 can be configured to be removed prior to use, or penetrated during injection just prior to delivery of the mixed fluid. Once injection is completed the needle guard spring 1154 can bias the needle guard 1110 outward into an extended and locked position so as to protect inadvertent sticks by the now extended needle.

Figure 26B:
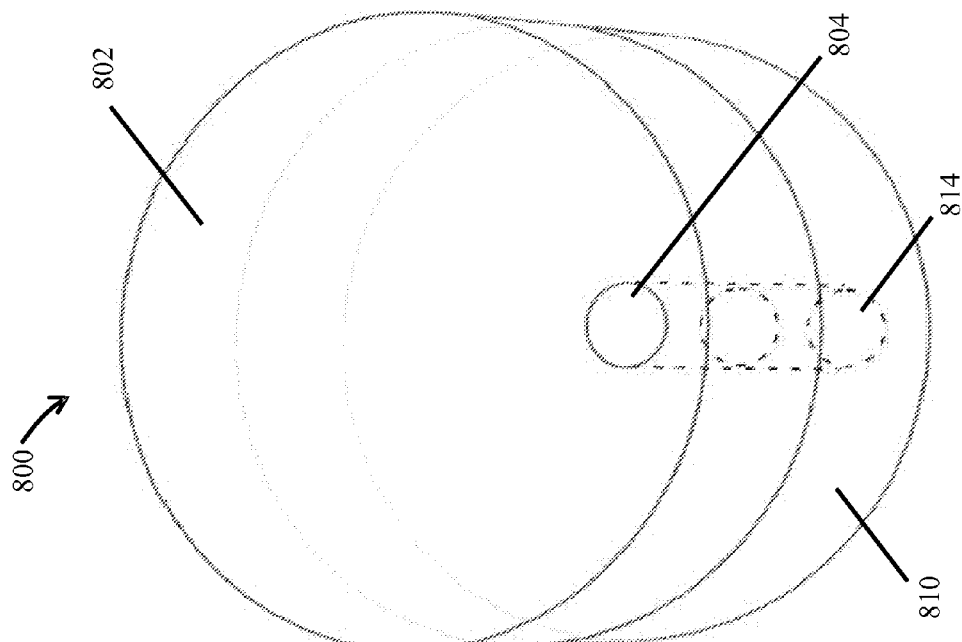
FIGS. 26A-B illustrate principles of a rotary valve adaptable for use in any of the embodiments discussed herein.
Figure 26A:
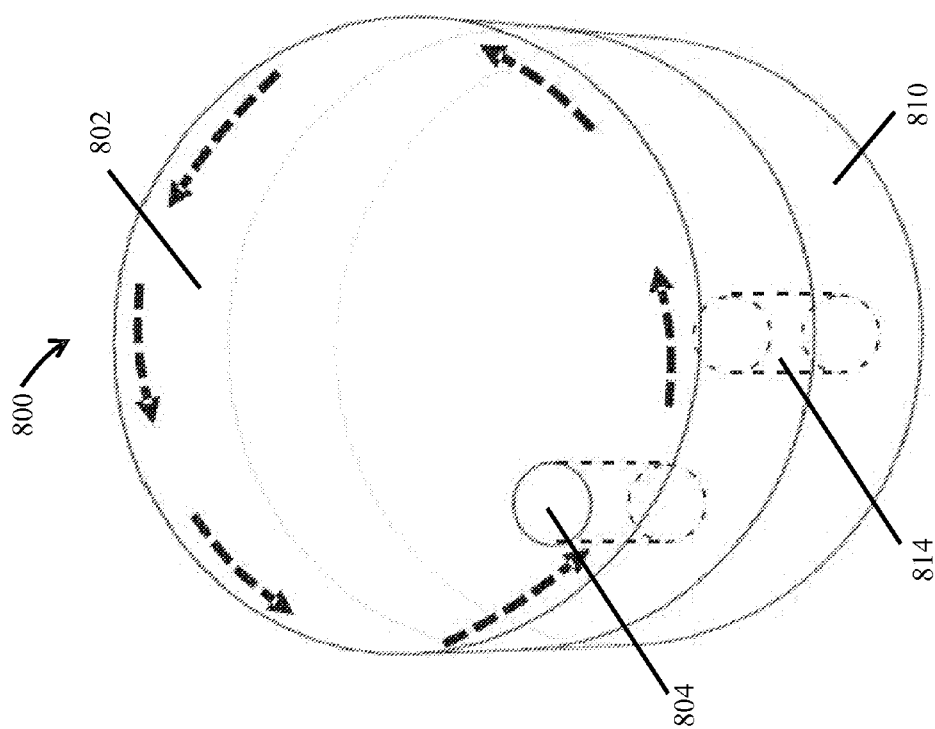

FIGS. 26A-B illustrate the principles of operation of a rotary valve 800 for use in the embodiments discussed above. A rotary valve can be formed wherein a fluidic pathway is established by rotating one aperture with another. In this exemplary illustration the aperture 804 can be provided in a bottom portion of a vial which forms a top interfacing portion 802 forming a chamber and the secondary aperture 814 provided through a bottom interfacing portion of the seal 810, which can be the inlet to the remaining portion of a fluidic channel leading to another chamber. FIG. 26A illustrates a closed configuration wherein the two apertures are misaligned and fluid communication does not exist. FIG. 26B illustrates an open configuration wherein the two apertures are aligned and fluid communication is established. It will be appreciated that in order to form a better seal, one or both of the components can be formed of a material having elastic properties such as rubber or silicone. In another embodiment, one of the components is rubber and another is hard plastic. In another embodiment each of the sealing surfaces are made up of a combination of hard plastic and elastomeric materials in one interface.

FIGS. 27A-D illustrate an alternative valve mixing assembly 900 which is effectuated by means of sliding two components axially with respect to one another so as to effectuate establishment of fluidic communication, rather than through rotation.

FIG. 27A illustrates a stowed state wherein fluid is contained in a first vial 910 by a first plunger 940, wherein the first vial 910 has an outlet 914 which is misaligned with the fluidic channel inlet 952 of the fluidic channel 950 in an axial direction, wherein the fluidic channel 950 provides fluidic communication with the second vial 920. The fluidic channel 950 is disposed in an intermediate body 930 which can double as a second plunger for the second vial. Mixing can be initiated through various cams or axially forces applied to the mixing system which cause a relative axial translation between the first vial 910 and the intermediate support 930 so as to align the outlet 914 with the fluidic channel inlet 952. The intermediate support can then be caused to translate axially with respect to the intermediate support simultaneously as the first plunger 940 is depressed into the first vial 910 until all of the fluid has been received in the second chamber 920 and completely displaced from the first chamber 910. Then both the first plunger and the intermediate support can be simultaneously depressed so as to displace the fluid out of the needle 960 which simultaneous depression can cause the needle to penetrate the needle guard 970. It will be appreciated that axial translation can be achieved by translating rotational motion using ramped cam systems and corresponding protrusions, various spring mechanisms in different configurations all of which will be within the scope of the present invention and will also be within the understanding of one of ordinary skill in the art having possession of this disclosure.

For purposes of the sliding valve of FIGS. 27A-D it will be appreciated that various effectuation means can be effectuated by various protrusions such as on the vial sleeve which can translate within channels provided in adjacent components so as to effectuate the axial translation of the first chamber, and its associated outlet, with the inlet of the fluidic channel.

Figure 28C:
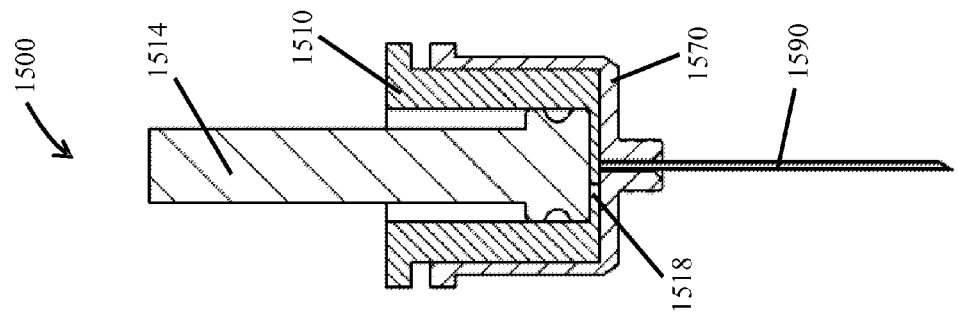
FIGS. 28A-C illustrate various cross sectional views of yet another alternative embodiment of a medication mixing and delivery device in various actuated states which utilize chambers which are independently movable within a housing.
Figure 28B:
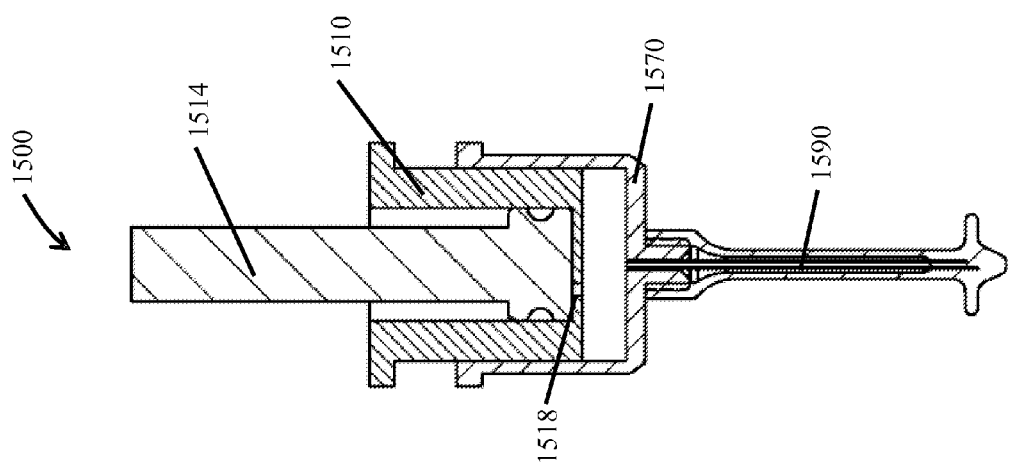
Figure 28A:
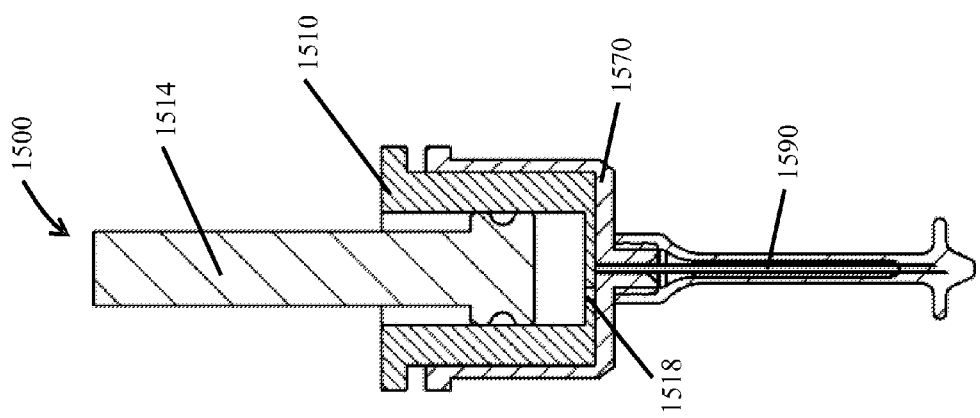

FIGS. 28A-C illustrate yet another mixing assembly 1500 adaptable for use in one or more of the auto-injectors above. This alternative valve mixing assembly 1500 is effectuated by displacing a first chamber 1510 with respect to an initially stationary plunger 1514, the outer surface of the first chamber 1510 can be provided with a seal and function as a plunger for a second chamber 1570. By displacing the first chamber 1510 upward, a fluid contained therein can travel through an aperture or valve 1518 so as to be displaced into the second chamber 1570, which can contain the dry medicament therein, or the dry medicament can be stored in the fluidic channel, wherein the upward motion of the first chamber automatically expands in response to the upward motion of the first vial 1510. The second vial 1570 can be held stationary, or be provided with independent protrusions which cause it to not be drawn upward at all, or at least not be drawn upward at the same rate as the first vial 1510 so as to facilitate proper expansion in response to the volume of fluid moving from the first chamber into the second chamber. Once mixing is complete the plunger 1514 as well as the rest of the assembly can be forced downward so as to facilitate injection. For purposes of illustration, a spring could be configured to act on the plunger after mixing is complete and provide a compressive force of the mixing assembly 1500 between the spring and an outer housing in which the mixing assembly resides so as to displace the fluid from the second chamber and out of the needle 1590.which is effectuated by means of sliding two components axially with respect to one another so as to effectuate establishment of fluidic communication, rather than through rotation.

Figure 29:
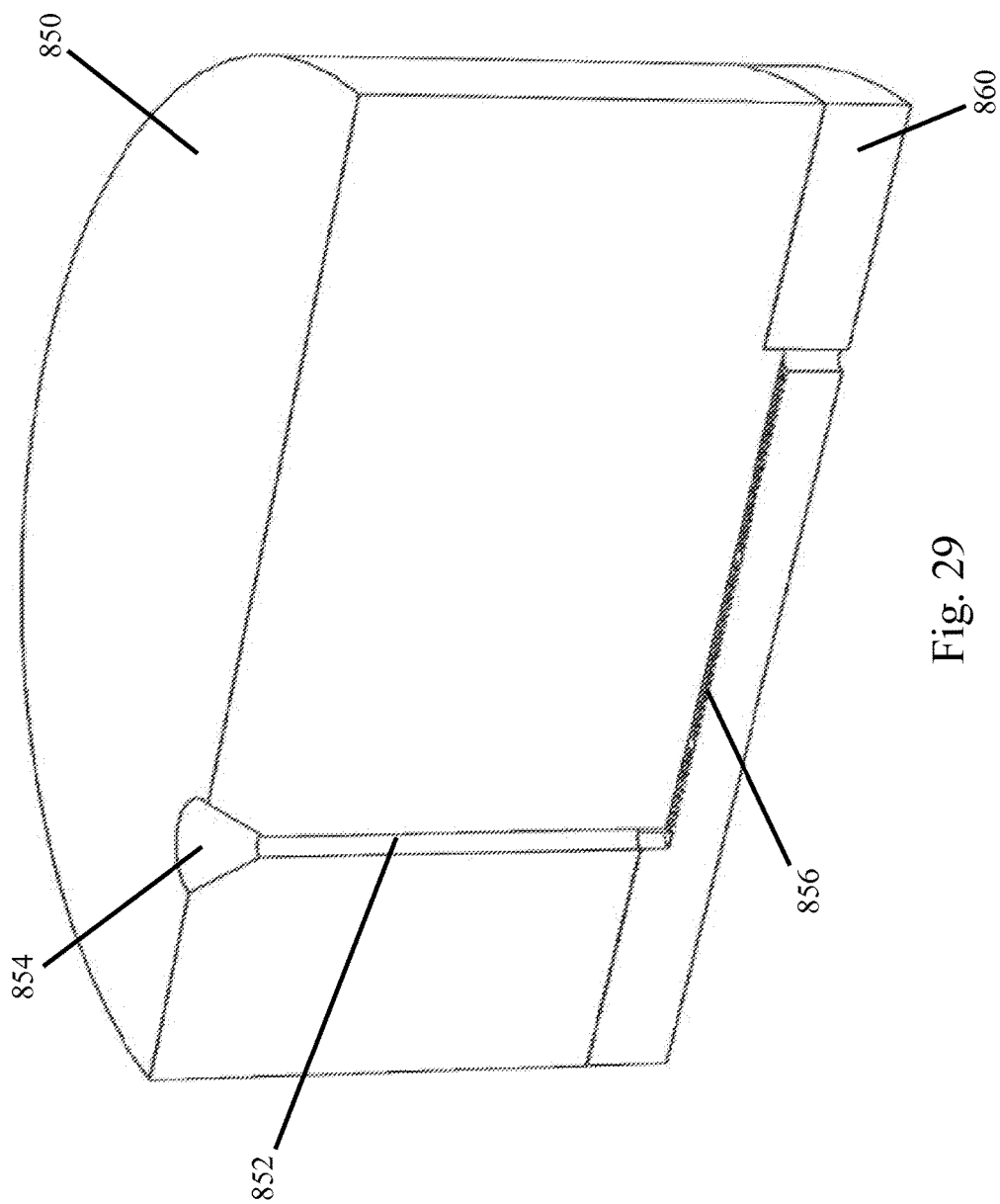
FIG. 29 illustrates an exemplary fluidic channel arrangement adaptable for use in any of the embodiments discussed herein.
Figure 30:
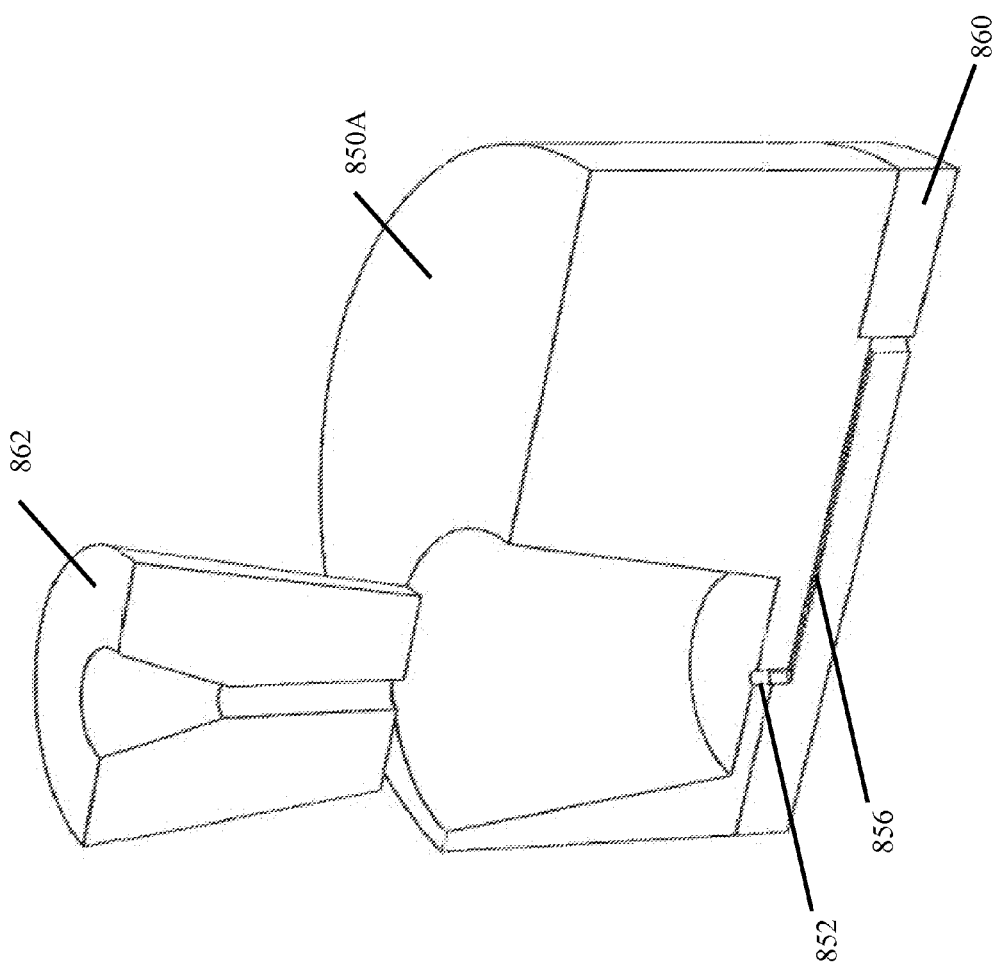
FIG. 30 illustrates an exemplary fluidic channel and removable ferrule arrangement adaptable for use in any of the embodiments discussed herein.

FIGS. 29-30 illustrate various intermediate bodies 850 and 850A having fluidic channels 852 disposed therein. The fluidic channel 852 can have an inlet 854 for receiving a fluid and allowing the fluid to pass therethrough. In some embodiments a secondary fluidic body 860 having a secondary fluidic channel 856 can be provided which receives the fluid, the secondary fluidic body can introduce additional flow features so as to affect flow therethrough. In the embodiment shown the secondary body can be provided with a plurality of turbulence features which induce turbulent flow and increase flow speed, pressure differential, and can increase the effectiveness of mixing between the fluid and a dry medicament which can be stored therein. In another embodiment the dry medicament can be stored in 854.

FIG. 30 illustrates an alternative intermediate body 850A with a recess configured to receive a customizable ferrule 862. The ferrule can have an enlarged interior portion configured to receive an amount of dry medicament wherein a selection of ferrules can be provided having greater or smaller interior portions for adjusting the dosage of medicament for a particular end user. It will be appreciated that the intermediate bodies of these respective embodiments can be oriented in any fashion such that the inlets or outlets are switched or such that the ferrule is at either an inlet or outlet of its respective intermediate body.

Figure 31A:
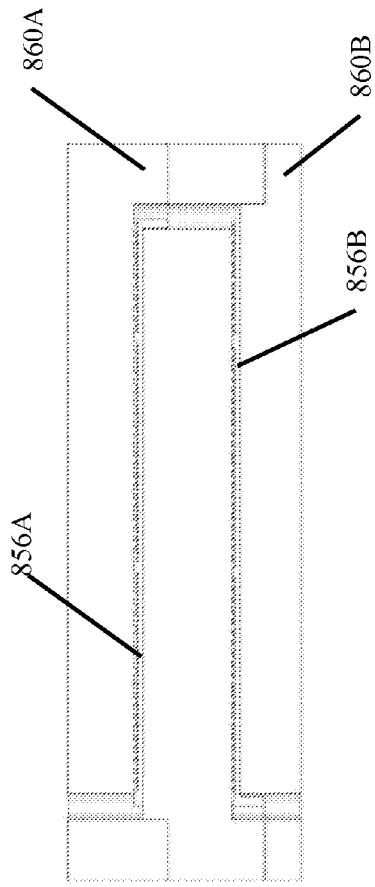
FIGS. 31A-B illustrate various features and embodiments of fluidic channel arrangements adaptable for use in any of the embodiments discussed herein.

FIG. 31A illustrates additional embodiments of secondary fluidic bodies 860A and 860B which can introduce additional bends and passes to the various fluidic pathways 856A-B.

Figure 31B:
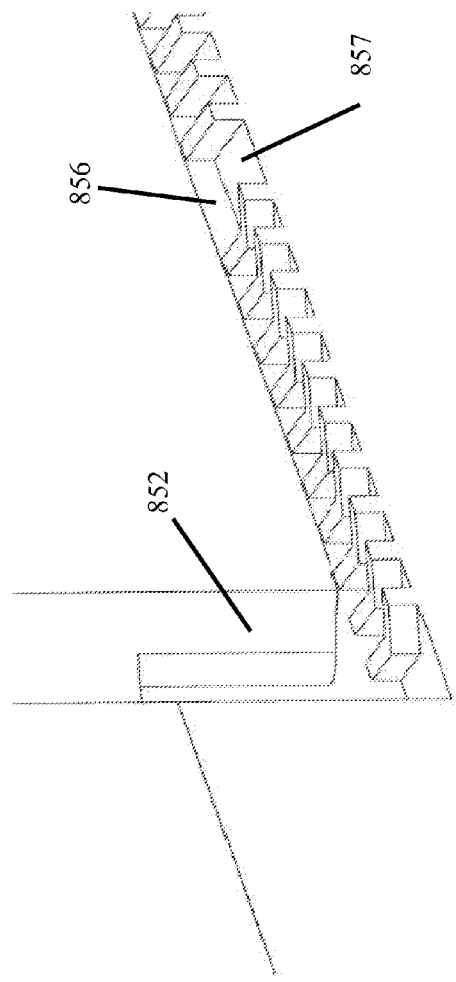

FIG. 31B illustrates a detailed perspective cross sectional view of a fluidic channel 856 and respective turbulence inducing features 857.

Figures 32A, 32B, 32C:
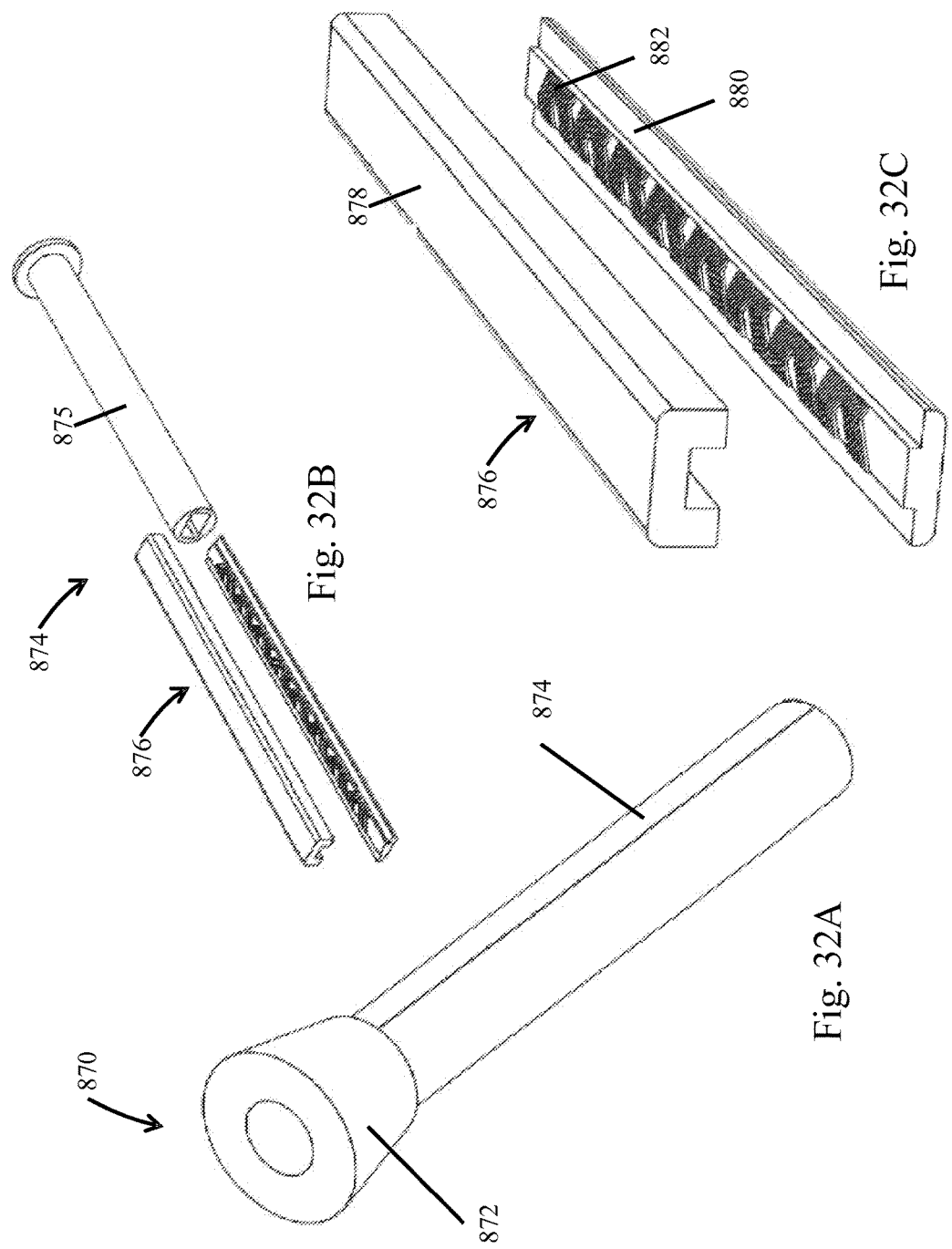
FIGS. 32A-C illustrate various additional features of yet another alternative embodiments of a fluidic channel arrangement adaptable for use in any of the embodiments discussed herein.

FIGS. 32A-C illustrates a fluidic channel assembly 870 which can be adapted for use with any of the embodiments discussed above. The fluidic channel assembly 870 can include a dosage ferrule 872, which in one embodiment contains dry powder medicament, a channel sleeve 875 and a fluidic channel 876. A fluidic channel insert 874 for use in the fluidic channel assembly 870 can be formed by coupling two separate plates 878 and 880 which are machined to form a gap when pressed together thus forming the fluidic channel 876. By forming the fluidic channel between two separate plates, more complex internal features 882 can be formed prior to assembly. It will be appreciated that the two plates can be bonded in any suitable manner such as welding, adhesive, etc. The channel sleeve can then be provided so as to ensure a seal and reduce leakage. This fluidic channel insert 870 can be adapted for use with any of the embodiments discussed above.

Figure 33B:
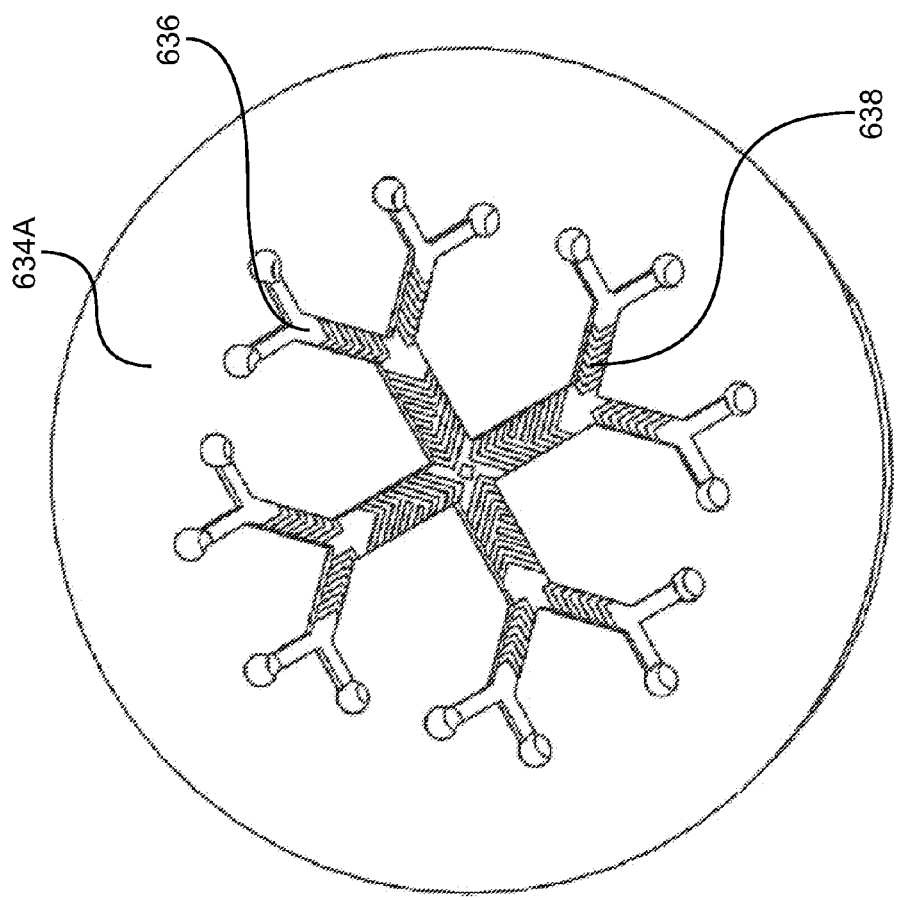
FIGS. 33A-B illustrates various additional features of yet another alternative embodiment of a fluidic channel arrangement adaptable for use in various embodiments discussed herein.
Figure 33A:
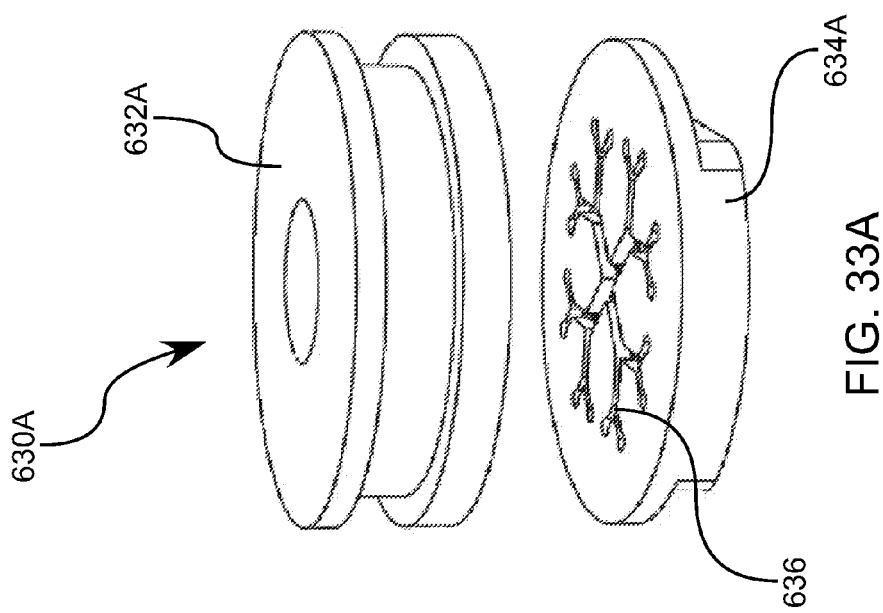

FIGS. 33A-B illustrate yet another embodiment of a proposed fluidic channel assembly 630A. This fluidic channel assembly 630A can be formed of a seal component 632A which directs fluid received from an upper portion into a desired entry point on a fluidic channel component 634A. In one embodiment, a dry powder medicament can be stored in the pocket recess in 632A. In another embodiment, a dry powder medicament can be stored in the fluidic channels 636 and 638. Various fluidic channel designs 636 and features 638 can be formed into an upper surface of the fluidic channel component 634A in virtually any suitable configuration through various machining means, laser, acid etching, injection molding, or embossing or any other suitable process so as to form a desired channel configuration 636 or features 638. The channels can ensure proper fluid dispersion, induce turbulence, or provide any other number of desired flow characteristics of the fluid passing therethrough.

It will be further understood by those in possession of this disclosure that the chambers and respective plungers can be movable with respect to one another. As such, in some cases, and as shown here, translating the plunger into the vial which forms the respective chamber can be one method of reducing the effective volume and displacing fluid contained therein. In other embodiments the vials themselves cay be displaced onto, or with respect to, a stationary plunger so as to provide the displacement force. In yet other embodiments a combination of the two can be utilized so as to provide the displacement effect.

Figure 34B:
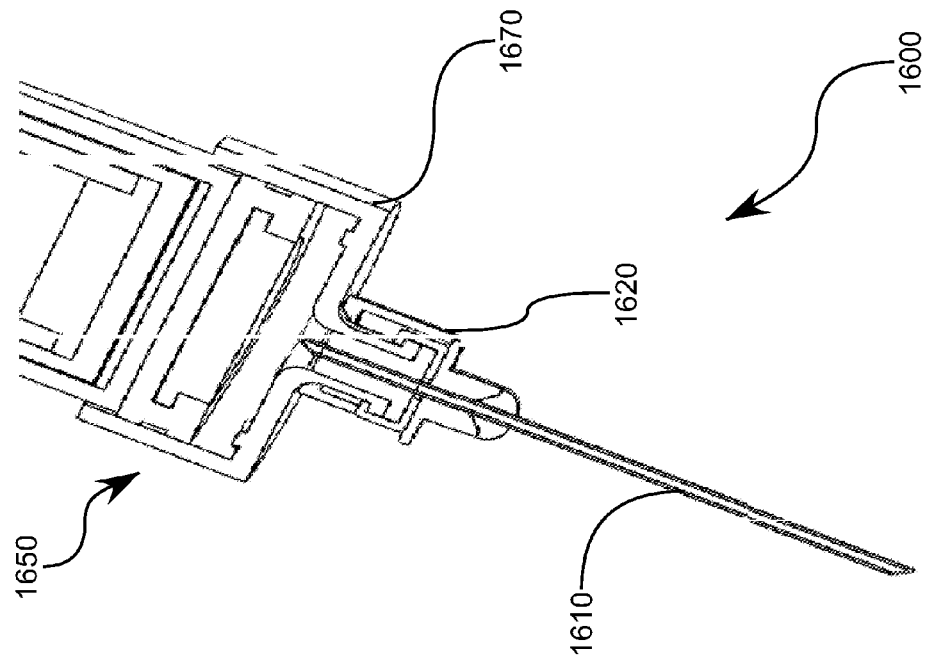
FIGS. 34A-B illustrate extended and retracted states of a delivery or injection assembly adaptable for use in any of the aforementioned embodiments.
Figure 34A:
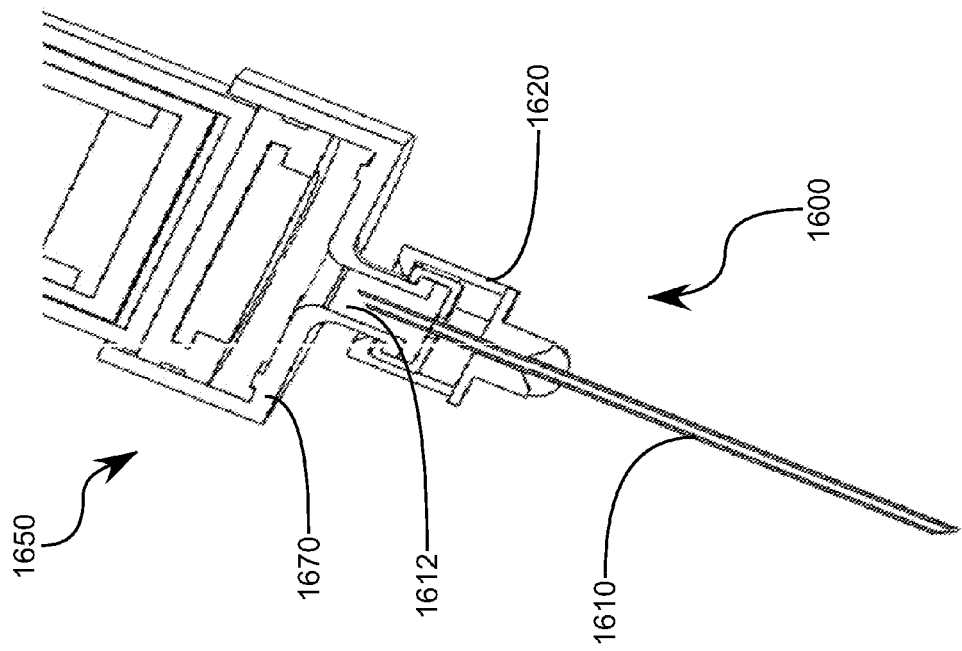

FIGS. 34A-B illustrate an injection or delivery assembly 1600 adaptable for use with any of the auto-injectors discussed above. FIG. 34A illustrates an exemplary mixing assembly 1650, similar to any of the mixing assemblies disclosed herein, the mixing assembly 1650 having an expanded second chamber 1670 containing the mixed drug and liquid component just prior to injection. A septum 1612 is provided between the inlet end of the needle 1610 and separates the interior channel or cannula of the needle from introducing contaminants therethrough into the second chamber 1670 prior to injection. Additionally septum separates the needle from the interior of the second chamber so as to prevent premature leaking and full mixing of the various components prior to actuation and injection.

It will be appreciated that the needle has both a distal or injection end and a proximal end. The distal end can be configured to enter into a patient at an injection site and the proximal or inlet end being configured to pierce and ultimately penetrate the septum. It will be further appreciated that in FIG. 34A the needle 1610 has still not yet penetrated the septum 1612.

As shown in FIG. 34A, the needle 1610 can be partially embedded into, but not fully penetrated through, the septum 1612 in a stowed state wherein the needle 1610 can penetrate the septum 1612 and open fluid communication out the injection end just prior to injection.

In order to provide penetration of the septum 1612 by the needle 1610, the needle can be carried by a translating needle carrier 1620. The needle carrier 1620 can have a translating body which is allowed to translate axially along the needle axis with respect to the second chamber 1670 and the septum 1612. The degree of translation can be limited or controlled by providing abutting shoulders which interfere with one another at certain points along the relative travel distance between the carrier and the second chamber. In one instance the shoulders can engage to prevent the needle from being released from the system and sliding out of the auto injector entirely, and in another instance the shoulders can engage to provide the axial translation and puncture force of the needle through the septum when pushed down just prior to injection. In the cross sectional view of FIGS. 34A the needle carrier is extended to its maximum distance away from the second chamber.

FIG. 34B illustrates the injection motion of pressing the auto injector up to an injection site. The downward force drives the needle 1610 downward with respect to the needle shield to expose the needle from the interior of the auto injector body. A shoulder or stop can be provided on the interior of the needle shield which engages with the needle carrier and pushes the proximal end of the needle through to fully penetrate through the septum. At this point a fluid pathway is established and fluid communication is provided from the second chamber into the patient's body or other injection site. At this point a second plunger can be pushed into the second chamber thus forcing the mixed drug into the injection site.

While the principles of the invention have been described herein, it is to be understood by those skilled in the art that this description is made only by way of example and not as a limitation as to the scope of the invention. Other embodiments are contemplated within the scope of the present invention in addition to the exemplary embodiments shown and described herein. Modifications and substitutions by one of ordinary skill in the art are considered to be within the scope of the present invention.

What is claimed:

1. A medication mixing and delivery device comprising:
   a housing;
   a first chamber located within the housing, the first chamber having an outlet;
   a second chamber located within the housing, the second chamber having an inlet;
   a rotary valve located within the housing, the rotary valve being selectively opened or closed by aligning or misaligning the outlet of the first chamber to cause or prevent fluid communication between the outlet of the first chamber and the inlet of the second chamber;

an actuation device having a pre-stored energy source, the actuation device also being in mechanical communication with the rotary valve and is configured to allow the rotatory valve to alternate between a closed and open state;
a displacement mechanism configured to reduce an effective volume of the first chamber;
a delivery assembly configured to be in fluid communication with the second chamber;
wherein the actuation device is activated by an axial torsional force, which axial torsional force causes the rotary valve to be placed into the open state and wherein the axial torsional force causes a first portion of energy stored within the pre-stored energy source to be released and cause the displacement mechanism to force a liquid stored in the first chamber to pass through the outlet and the inlet to be received by the second chamber,
wherein a dry medicament is stored within the housing and outside the first chamber, and
wherein the second chamber becomes rotationally fixed with the first chamber upon releasing the first portion of stored energy; and
a second actuation device that is configured to release a second portion of energy from the pre-stored energy source, which upon release forces the liquid, which is now located in the second chamber, to be displaced out of the second chamber through the delivery assembly.

* * * * *